United States Patent
Ramsdell

(10) Patent No.: US 10,895,574 B2
(45) Date of Patent: Jan. 19, 2021

(54) LEFT-RIGHT GENE EXPRESSION SIGNATURE FOR TRIPLE NEGATIVE BREAST CANCER

(71) Applicant: University of South Carolina, Columbia, SC (US)

(72) Inventor: Ann F. Ramsdell, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/887,578

(22) Filed: Feb. 2, 2018

(65) Prior Publication Data

US 2018/0246108 A1    Aug. 30, 2018

Related U.S. Application Data

(60) Provisional application No. 62/461,262, filed on Feb. 21, 2017.

(51) Int. Cl.
| | | |
|---|---|---|
| *C12Q 1/68* | (2018.01) | |
| *C12P 19/34* | (2006.01) | |
| *G01N 33/574* | (2006.01) | |

(52) U.S. Cl.
CPC ... *G01N 33/57415* (2013.01); *G01N 2800/50* (2013.01); *G01N 2800/56* (2013.01); *G01N 2800/60* (2013.01); *G01N 2800/7028* (2013.01)

(58) Field of Classification Search
CPC ........... G01N 2800/50; G01N 2800/56; G01N 2800/60; G01N 2800/7028; G01N 33/57415
See application file for complete search history.

(56) References Cited

U.S. PATENT DOCUMENTS

2001/0053519 A1*  12/2001  Fodor ................... B82Y 30/00
435/6.11

OTHER PUBLICATIONS

Data Sheet: GeneChip® Mouse Genome Arrays. Part No. 701525 Rev. 4. Available online, 4 pages printed from www.affymetrix.com/support/technical/datasheets/mogarrays_datasheet.pdf (Year: 2004).*
Expression Probeset Details for MOUSE430_2:1448962 AT (mouse gene: myh11), available online, 4 pages printed from https://www.affymetrix.com/analysis/netaffx/fullrecord.affx?pk=MOUSE430_2:1448962_AT on Apr. 20, 2020. (Year: 2020).*
Frazier, K.S. et al. "Expression of Connective Tissue Growth Factor mRNA in the Fibrous Stroma of Mammary Tumors" Int. J. Biocehm. Cell Biol. vol. 29. No. 1. pp. 153-161. (Year: 1997).*
Robichaux, J. P., Hallett, R. M., Fuseler, J. W., Hassell, J. A. & Ramsdell, A. F. "Mammary Glands Exhibit Molecular Laterality and Undergo Left-Right Asymmetric Ductal Epithelial Growth in MMTV-cNeu Mice*." Oncogene 34, 2003-2010 (2015).
Perou, C. M. "Molecular Stratification of Triple-Negative Breast Cancers. Oncologist" 16 Suppl 1, 61-70, 2011-S1-61 (2011).
Norum, J. H., Andersen, K. & Sorlie, T. "Lessons learned from the intrinsic subtypes of breast cancer in the quest for precision therapy." The British journal of surgery 101, 925-938 (2014).
Pouladi, N., Cowper-Sallari, R. & Moore, J. H. "Combining functional genomics strategies identifies modular heterogeneity of breast cancer intrinsic subtypes." BioData mining 7, 27, (2014).
Tao, K., Fang, M., Alroy, J. & Sahagian, G. G. "Imagable 4T1 model for the study of late stage breast cancer." BMC cancer 8, 228 (2008).
Conklin, M. W. & Keely, P. J. "Why the stroma matters in breast cancer: insights into breast cancer patient outcomes through the examination of stromal biomarkers." Cell adhesion & migration 6, 249-260 (2012).
Dittmer, J. & Leyh, B. "The impact of tumor stroma on drug response in breast cancer." Seminars in cancer biology 31, 3-15 (2015).
Maffini, M. V., Soto. A. M., Calabro, J. M., Ucci, A. A. & Sonnenschein, C. "The stroma as a crucial target in rat mammary gland carcinogenesis." Journal of cell science 117, 1495-1502, (2004).
Unsworth, A., Anderson, R. & Britt, K. "Stromal fibroblasts and the immune microenvironment: partners in mammary gland biology and pathology?" J Mammary Gland Biol Neoplasia 19, 169-182 (2014).
Abstract of Pulaski, B. A. & Ostrand-Rosenberg, S. Mouse 4T1 breast tumor model. Current protocols in immunology / edited by John E. Coligan [et al.] Chapter 20, Unit 20 22, (2001).
Bonapace, L. et al. "Cessation of CCL2 inhibition accelerates breast cancer metastasis by promoting angiogenesis." Nature 515, 130-133 (2014).

* cited by examiner

*Primary Examiner* — Stephan T Kapushoc
(74) *Attorney, Agent, or Firm* — Dority & Manning, P.A.

(57) ABSTRACT

Methods and materials are described for use in clinical and research applications directed to cancers. Products include binding arrays e.g., hybridization or other specific binding arrays such as genomic or proteomic microarrays. The binding arrays include binding agents developed based upon the recognition of heterogeneity between left-arising and right-arising breast cancer tumors. The arrays can include as binding agents materials that bind transcripts or proteins that are over-expressed in only one of or in both of left-arising or right-arising breast cancer tumors.

7 Claims, 36 Drawing Sheets

FIG. 1

| Gene_id | Gene_name | log(FC) | Gene_id | Gene_name | log(FC) | Gene_id | Gene_name | log(FC) |
|---|---|---|---|---|---|---|---|---|
| ENSG00000240386.3 | LCE1F | 6.207008038 | ENSG00000258482.1 | TRAV15 | 1.85556314 | ENSG00000280254.1 | RNU6-536P | 1.43623813 |
| ENSG00000175329.11 | ISX | 4.963820166 | ENSG00000206855.1 | RNU6-571P | 1.85272657 | ENSG00000265352.1 | | 1.44398744 |
| ENSG00000250431.1 | | 4.537627442 | ENSG00000254095.1 | | 1.85141526 | ENSG00000278239.1 | | 1.43384747 |
| ENSG00000221265.1 | MIR1255A | 4.173073327 | ENSG00000262400.1 | | 1.85026129 | ENSG00000211701.2 | TRGV1 | 1.43218221 |
| ENSG00000250256.1 | | 4.141033928 | ENSG00000267463.1 | UBE2V2P2 | 1.8454678 | ENSG00000257837.1 | | 1.43061649 |
| ENSG00000254908.3 | LINC00051 | 4.118196175 | ENSG00000278804.1 | | 1.84180706 | ENSG00000236119.1 | | 1.43054671 |
| ENSG00000251380.3 | DCANP1 | 4.021398557 | ENSG00000253784.1 | | 1.83782478 | ENSG00000204099.10 | NEU4 | 1.42983149 |
| ENSG00000226484.2 | | 4.019348594 | ENSG00000212445.1 | | 1.83482563 | ENSG00000258312.1 | | 1.42250107 |
| ENSG00000213759.7 | UGT2B11 | 3.902530796 | ENSG00000260518.1 | BMS1P8 | 1.83463108 | ENSG00000109906.12 | | 1.41974001 |
| ENSG00000230696.1 | | 3.858304381 | ENSG00000230698.1 | | 1.8333041 | ENSG00000274704.1 | | 1.41810637 |
| ENSG00000259265.1 | | 3.781064515 | ENSG00000249446.2 | TRAJ60 | 1.82784094 | ENSG00000229160.1 | | 1.41671599 |
| ENSG00000274730.1 | | 3.748662308 | ENSG00000267022.2 | | 1.8259531 | ENSG00000223253.1 | | 1.41542144 |
| ENSG00000096006.10 | CRISP3 | 3.652909903 | ENSG00000241654.1 | RPL19P18 | 1.81806096 | ENSG00000140506.15 | LMAN1L | 1.41438323 |
| ENSG00000256081.2 | | 3.577384927 | ENSG00000229859.7 | PGA3 | 1.81653015 | ENSG00000205097.5 | PRG2 | 1.41300612 |
| ENSG00000231019.1 | | 3.534097835 | ENSG00000234573.1 | | 1.81437475 | ENSG00000104760.15 | FGL1 | 1.4129312 |
| ENSG00000271168.1 | | 3.527574919 | ENSG00000234673.1 | | 1.81433859 | ENSG00000224141.4 | | 1.41253526 |
| ENSG00000231467.2 | | 3.422958488 | ENSG00000270759.1 | | 1.81123078 | ENSG00000205669.2 | ACOT6 | 1.40969963 |
| ENSG00000175535.6 | PNLIP | 3.378976973 | ENSG00000248475.4 | RNU6-1046P | 1.80826843 | ENSG00000233217.1 | MROH3P | 1.40804569 |
| ENSG00000235492.1 | LINC01221 | 3.378151058 | ENSG00000273840.1 | | 1.80588212 | ENSG00000276147.1 | MIR548AY | 1.4074971 |
| ENSG00000249106.3 | | 3.353232904 | ENSG00000259925.1 | | 1.80510352 | ENSG00000258618.2 | RPL21P9 | 1.40696291 |
| ENSG00000232254.1 | CSF2RBP1 | 3.327513897 | ENSG00000255157.1 | | 1.80269656 | ENSG00000271977.1 | | 1.40602278 |
| ENSG00000206651.6 | RGPD4-AS1 | 3.296323838 | ENSG00000252347.1 | | 1.80142219 | ENSG00000250974.1 | | 1.4031658 |
| ENSG00000197437.3 | OR13G1 | 3.232037871 | ENSG00000249265.1 | | 1.79935656 | ENSG00000164729.7 | SLC35G3 | 1.40261817 |
| ENSG00000223433.1 | | 3.199681789 | ENSG00000256691.1 | | 1.79471122 | ENSG00000223970.1 | | 1.401141 |
| ENSG00000225066.1 | | 3.144876475 | ENSG00000221314.1 | | 1.79468181 | ENSG00000215343.6 | ZNF705D | 1.39916185 |
| ENSG00000240235.3 | RN7SL794P | 3.140981866 | ENSG00000224807.5 | DUX4L9 | 1.79240006 | ENSG00000250064.1 | | 1.39822118 |
| ENSG00000248810.3 | | 3.126036403 | ENSG00000273745.1 | MIR6870 | 1.79147689 | ENSG00000239571.1 | IGKV2D-30 | 1.39260993 |
| ENSG00000234308.2 | | 3.114702233 | ENSG00000274840.3 | | 1.78337996 | ENSG00000257389.1 | | 1.39199539 |
| ENSG00000276489.1 | MIR6829 | 3.086790389 | ENSG00000277066.1 | | 1.77546486 | ENSG00000166220.11 | TBATA | 1.39080198 |
| ENSG00000269055.3 | BNIP3P18 | 3.084446156 | ENSG00000274883.1 | | 1.7750018 | ENSG00000272164.1 | | 1.39042662 |
| ENSG00000230081.2 | HSPE1P28 | 3.075500859 | ENSG00000273244.1 | | 1.76761946 | ENSG00000232044.6 | LINC01105 | 1.3903214 |
| ENSG00000201210.1 | RNA5SP139 | 3.045225943 | ENSG00000105428.5 | ZNRF4 | 1.76517593 | ENSG00000225505.1 | | 1.38527587 |

FIG. 1 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000221385.1 | | 3.041501289 | ENSG00000265009.1 | | 1.76463556 | ENSG00000276569.1 | | 1.3837922 |
| ENSG00000146618.3 | FERD3L | 3.04048926 | ENSG00000240156.1 | COX6CP6 | 1.76424315 | ENSG00000223563.1 | | 1.38301925 |
| ENSG00000293315.5 | MCHR2-AS1 | 3.030804956 | ENSG00000152034.9 | MCHR2 | 1.76377328 | ENSG00000264151.4 | | 1.37629932 |
| ENSG00000273830.1 | MIR7843 | 3.029359592 | ENSG00000133454.14 | MYO18B | 1.75987747 | ENSG00000254138.1 | | 1.3757924 |
| ENSG00000131050.9 | BPIFA2 | 3.016223358 | ENSG00000198251.7 | | 1.75934382 | ENSG00000239227.1 | | 1.37576387 |
| ENSG00000250584.2 | LINC01511 | 3.015427126 | ENSG00000268756.1 | | 1.75783777 | ENSG00000214407.3 | | 1.37510567 |
| ENSG00000109181.10 | UGT2B10 | 3.013948409 | ENSG00000255171.4 | LINC01499 | 1.75760831 | ENSG00000240128.1 | KRT18P43 | 1.3744023 |
| ENSG00000203858.3 | HSD3BP2 | 2.985082123 | ENSG00000276989.1 | | 1.7573944 | ENSG00000244468.1 | | 1.37357919 |
| ENSG00000197408.7 | CYP2B6 | 2.956692562 | ENSG00000214064.3 | RPL6P5 | 1.75697802 | ENSG00000274057.3 | | 1.37035477 |
| ENSG00000204398.5 | | 2.951944623 | ENSG00000261432.1 | | 1.75207884 | ENSG00000278811.3 | LINC00624 | 1.36983475 |
| ENSG00000224219.1 | | 2.950493938 | ENSG00000234658.1 | | 1.75146443 | ENSG00000281228.1 | | 1.36979964 |
| ENSG00000279840.1 | | 2.939157816 | ENSG00000259517.2 | | 1.74584075 | ENSG00000166069.12 | TMCO5A | 1.36906087 |
| ENSG00000237137.1 | | 2.93631691 | ENSG00000271519.1 | | 1.74560735 | ENSG00000115009.10 | CCL20 | 1.36792044 |
| ENSG00000100867.13 | DHRS2 | 2.933605658 | ENSG00000261733.1 | | 1.74584569 | ENSG00000214695.3 | NPAP1P2 | 1.36629076 |
| ENSG00000250038.4 | | 2.913702317 | ENSG00000263835.4 | | 1.7377401 | ENSG00000181552.3 | EDDM3B | 1.36602367 |
| ENSG00000264400.2 | RN7SL491P | 2.917719939 | ENSG00000156006.4 | NAT2 | 1.7377384 | ENSG00000203565.2 | | 1.36355788 |
| ENSG00000277757.3 | | 2.896570382 | ENSG00000233501.1 | SRGAP2-AS1 | 1.73747912 | ENSG00000179452.2 | | 1.36309645 |
| ENSG00000225811.1 | | 2.87361214 | ENSG00000147160.8 | AWAT2 | 1.7352888 | ENSG00000233969.1 | | 1.35624906 |
| ENSG00000234054.1 | | 2.86733704 | ENSG00000206043.6 | C18orf63 | 1.73411075 | ENSG00000130513.6 | GDF15 | 1.35457424 |
| ENSG00000224470.3 | | 2.847365032 | ENSG00000267207.1 | | 1.73102272 | ENSG00000237377.2 | | 1.354187885 |
| ENSG00000250409.1 | | 2.832965023 | ENSG00000138347.14 | MYPN | 1.72739749 | ENSG00000167769.4 | ACBR1 | 1.35303596 |
| ENSG00000157005.3 | SST | 2.816090037 | ENSG00000167751.31 | KLK2 | 1.72540107 | ENSG00000277241.1 | | 1.3512652 |
| ENSG00000275238.1 | MIR4734 | 2.806053198 | ENSG00000250696.4 | | 1.72183143 | ENSG00000199963.1 | RNU6-605P | 1.34939487 |
| ENSG00000229332.2 | PGBD4P8 | 2.800673041 | ENSG00000232943.1 | | 1.72017181 | ENSG00000228918.3 | LINC01344 | 1.34523235 |
| ENSG00000269475.2 | | 2.791160028 | ENSG00000258694.1 | | 1.71575514 | ENSG00000236190.1 | | 1.34361669 |
| ENSG00000212565.1 | | 2.790192157 | ENSG00000134640.2 | MTNR1B | 1.71372043 | ENSG00000225992.1 | TRGV4 | 1.34182829 |
| ENSG00000224366.1 | | 2.783144496 | ENSG00000184544.10 | DHRS7C | 1.7095611 | ENSG00000217686.2 | NUS1P4 | 1.34134831 |
| ENSG00000256653.1 | MIR548AK | 2.760415702 | ENSG00000230573.1 | | 1.70856928 | ENSG00000258392.1 | RPA2P3 | 1.340053 |
| ENSG00000237189.1 | | 2.751402476 | ENSG00000248654.1 | | 1.70563167 | ENSG00000230516.1 | | 1.33901602 |
| ENSG00000206073.9 | SERPINB4 | 2.747483374 | ENSG00000239288.1 | | 1.7051656 | ENSG00000260125.1 | AGBL1-AS1 | 1.33852266 |
| ENSG00000144010.8 | TRIM43B | 2.726542916 | ENSG00000236366.1 | | 1.70363025 | ENSG00000231428.2 | | 1.33837178 |
| ENSG00000253465.1 | IGHV1V-44-1 | 2.700929251 | ENSG00000237532.1 | | 1.69829294 | ENSG00000226097.4 | LINC00396 | 1.33808108 |

FIG. 1 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000249425.1 | | 2.681803418 | ENSG00000199837.1 | RNA5SP71 | 1.69511628 | ENSG00000261045.2 | | 1.33763845 |
| ENSG00000225172.4 | | 2.675111104 | ENSG00000184388.5 | PABPC1L2B | 1.69389662 | ENSG00000229630.1 | LINC01264 | 1.33651349 |
| ENSG00000234700.3 | | 2.673232209 | ENSG00000158786.4 | PLA2G2F | 1.69050521 | ENSG00000186115.11 | CYP4F2 | 1.33631329 |
| ENSG00000264050.1 | | 2.671660457 | ENSG00000231839.1 | | 1.69050452 | ENSG00000249206.1 | | 1.334961151 |
| ENSG00000250488.1 | | 2.638061148 | ENSG00000100373.8 | UPK3A | 1.68858734 | ENSG00000250882.1 | | 1.33478832 |
| ENSG00000225236.1 | | 2.632964714 | ENSG00000234008.1 | LINC01441 | 1.68280226 | ENSG00000277958.1 | | 1.33471659 |
| ENSG00000222001.2 | | 2.620432941 | ENSG00000230109.1 | | 1.68228473 | ENSG00000253874.1 | IGLV1V-66-1 | 1.33468997 |
| ENSG00000251191.6 | LINC00589 | 2.610278934 | ENSG00000273580.1 | | 1.68135334 | ENSG00000275293.1 | | 1.33388085 |
| ENSG00000277367.1 | | 2.604735572 | ENSG00000275896.3 | PRSS2 | 1.67829154 | ENSG00000264515.4 | | 1.33359886 |
| ENSG00000260722.1 | VN1R67P | 2.585365662 | ENSG00000254811.4 | | 1.67673472 | ENSG00000242753.1 | | 1.331570018 |
| ENSG00000251185.1 | | 2.578747787 | ENSG00000279042.1 | | 1.67447206 | ENSG00000226693.1 | NXNP1 | 1.33041632 |
| ENSG00000224814.1 | | 2.5786847 | ENSG00000272727.1 | | 1.67421992 | ENSG00000224723.1 | GUSBP10 | 1.32936147 |
| ENSG00000249736.1 | | 2.571332889 | ENSG00000233872.1 | | 1.67230698 | ENSG00000243944.4 | | 1.32928561 |
| ENSG00000257879.1 | | 2.569942416 | ENSG00000241018.1 | RCC2P5 | 1.66937454 | ENSG00000272046.1 | | 1.32822779 |
| ENSG00000230294.4 | | 2.569279282 | ENSG00000249349.1 | | 1.66895243 | ENSG00000228543.1 | | 1.32540934 |
| ENSG00000276266.1 | | 2.568000312 | ENSG00000225289.1 | RPL29P29 | 1.66829044 | ENSG00000279708.1 | | 1.32410246 |
| ENSG00000269779.1 | | 2.567174042 | ENSG00000279304.1 | | 1.6661014 | ENSG00000248496.1 | | 1.32071472 |
| ENSG00000214754.3 | | 2.543395455 | ENSG00000242948.1 | EPS15P1 | 1.66354485 | ENSG00000253959.1 | | 1.31936803 |
| ENSG00000212659.1 | KRTAP9-6 | 2.525041392 | ENSG00000160339.14 | FCN2 | 1.6621676 | ENSG00000310901.1 | | 1.31928432 |
| ENSG00000114248.8 | LRRC31 | 2.504596901 | ENSG00000202431.1 | RNU6-438P | 1.66028648 | ENSG00000270038.1 | | 1.31845174 |
| ENSG00000253780.1 | IGHVIII-2-1 | 2.500683874 | ENSG00000251363.2 | | 1.65903941 | ENSG00000268089.2 | GABRQ | 1.31805266 |
| ENSG00000207194.3 | RNU6-1026P | 2.483360812 | ENSG00000255334.1 | | 1.65902322 | ENSG00000132681.15 | ATP1A4 | 1.31784103 |
| ENSG00000233767.1 | PSMA6P3 | 2.464991522 | ENSG00000277861.1 | | 1.65836864 | ENSG00000239211.3 | RN7SL563P | 1.31657329 |
| ENSG00000140798.14 | ABCC12 | 2.450342687 | ENSG00000214691.7 | | 1.65835221 | ENSG00000261055.1 | | 1.31550947 |
| ENSG00000279220.1 | GPR1-AS | 2.449331493 | ENSG00000201377.1 | RNY4P23 | 1.65597919 | ENSG00000276584.1 | MIR6737 | 1.31328509 |
| ENSG00000281085.1 | | 2.448739509 | ENSG00000239997.1 | FCF1P3 | 1.65190498 | ENSG00000240058.3 | ARGFXP1 | 1.31255511 |
| ENSG00000154198.13 | CYP4Z2P | 2.437522067 | ENSG00000264119.1 | MIR4795 | 1.65184934 | ENSG00000265801.1 | | 1.31241872 |
| ENSG00000204936.8 | CD177 | 2.435069042 | ENSG00000233201.1 | | 1.64798747 | ENSG00000123977.8 | DAW1 | 1.31130372 |
| ENSG00000251470.1 | ASNSP4 | 2.431769876 | ENSG00000225936.1 | | 1.64798275 | ENSG00000221793.1 | | 1.31032333 |
| ENSG00000249003.1 | CLUHP4 | 2.430139789 | ENSG00000270677.1 | | 1.64691077 | ENSG00000267443.2 | | 1.30994503 |
| ENSG00000260797.1 | | 2.416131895 | ENSG00000252183.1 | RNU6-948P | 1.64352656 | ENSG00000130385.5 | BMP15 | 1.30472367 |
| ENSG00000274959.1 | SPDYE13P | 2.415373298 | ENSG00000230533.1 | | 1.63915012 | ENSG00000253534.1 | TRBV6-8 | 1.3034419 |

FIG. 1 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000269681.1 | | 2.413296804 | ENSG00000184716.12 | SERINC4 | 1.63699638 | ENSG00000275396.1 | | 1.30238 |
| ENSG00000212176.1 | RNA5SP207 | 2.413149306 | ENSG00000213335.4 | CLNS1AP1 | 1.63676345 | ENSG00000239715.1 | | 1.30139906 |
| ENSG00000252993.1 | | 2.411678193 | ENSG00000213708.6 | SLC16A14P1 | 1.63347326 | ENSG00000266604.1 | | 1.30057853 |
| ENSG00000198535.5 | C2CD4A | 2.401182212 | ENSG00000281576.1 | | 1.63217615 | ENSG00000225882.1 | LINC01456 | 1.299441154 |
| ENSG00000261683.1 | LINC00838 | 2.394799376 | ENSG00000278895.1 | | 1.628624511 | ENSG00000254702.1 | | 1.29712011 |
| ENSG00000169704.4 | GP9 | 2.386279157 | ENSG00000264493.1 | MIR4298 | 1.62532636 | ENSG00000273516.1 | | 1.29577241 |
| ENSG00000178928.7 | TPRX1 | 2.383366687 | ENSG00000112077.14 | RHAG | 1.62386253 | ENSG00000250405.2 | | 1.29385328 |
| ENSG00000226715.1 | IYD | 2.381318714 | ENSG00000106648.12 | GALNTL5 | 1.62044378 | ENSG00000233292.1 | | 1.28991603 |
| ENSG00000218819.4 | TDRD15 | 2.373457827 | ENSG00000186458.4 | DEFB132 | 1.61487074 | ENSG00000229722.1 | | 1.28972655 |
| ENSG00000230056.1 | DDX6P3 | 2.366766143 | ENSG00000235005.1 | | 1.61479491 | ENSG00000181626.11 | | 1.28971607 |
| ENSG00000197990.6 | ZNF734P | 2.350975844 | ENSG00000199032.1 | MIR425 | 1.61351786 | ENSG00000186328.4 | ANKRD62 | 1.28959369 |
| ENSG00000009765.13 | IYD | 2.349076381 | ENSG00000263637.1 | | 1.61280809 | ENSG00000258573.4 | | 1.28935666 |
| ENSG00000249945.1 | | 2.347710739 | ENSG00000206144.5 | | 1.61278939 | ENSG00000263185.1 | | 1.28741194 |
| ENSG00000226983.2 | | 2.340284159 | ENSG00000257454.1 | | 1.61146679 | ENSG00000083622.8 | | 1.28627787 |
| ENSG00000162685.6 | LSP1P3 | 2.339966158 | ENSG00000256713.6 | PGA5 | 1.61076495 | ENSG00000232164.1 | | 1.28368853 |
| ENSG00000271564.1 | | 2.339865939 | ENSG00000225522.2 | | 1.60628475 | ENSG00000143556.7 | S100A7 | 1.28305579 |
| ENSG00000213556.3 | | 2.326042427 | ENSG00000243446.3 | RN7SL284P | 1.60176859 | ENSG00000214215.3 | C12orf74 | 1.28264743 |
| ENSG00000269466.2 | | 2.318951471 | ENSG00000225952.1 | | 1.60145896 | ENSG00000234455.1 | | 1.28143627 |
| ENSG00000186288.5 | PABPC1L2A | 2.316169682 | ENSG00000201967.1 | RN7SKP22 | 1.59959897 | ENSG00000215372.6 | ZNF705G | 1.28110222 |
| ENSG00000253376.1 | | 2.299133541 | ENSG00000224057.1 | EGFR-AS1 | 1.59871352 | ENSG00000251408.1 | | 1.28076209 |
| ENSG00000222558.1 | RNU6-1064P | 2.298859377 | ENSG00000227802.1 | DNAJB3 | 1.59572526 | ENSG00000226882.1 | UBE2V1P5 | 1.27923164 |
| ENSG00000248328.1 | | 2.297425243 | ENSG00000253182.1 | | 1.59429522 | ENSG00000238532.1 | | 1.27677945 |
| ENSG00000172238.4 | ATOH1 | 2.292723402 | ENSG00000269998.1 | | 1.59416274 | ENSG00000226838.1 | | 1.2754937 |
| ENSG00000267675.1 | | 2.276647382 | ENSG00000184029.8 | DSCR4 | 1.58999596 | ENSG00000214031.2 | | 1.27513804 |
| ENSG00000250324.2 | MRPL23P1 | 2.264653872 | ENSG00000238256.1 | MTND5P20 | 1.58824049 | ENSG00000230271.1 | | 1.27343189 |
| ENSG00000210841.1 | RNU6ATAC26P | 2.259576603 | ENSG00000254219.1 | | 1.5876478 | ENSG00000057593.12 | F7 | 1.27168635 |
| ENSG00000267116.1 | | 2.255408665 | ENSG00000253282.1 | | 1.58554594 | ENSG00000253235.1 | | 1.27016196 |
| ENSG00000255193.1 | | 2.246757039 | ENSG00000252236.1 | | 1.58472799 | ENSG00000201153.1 | RNU6-371P | 1.26960849 |
| ENSG00000247705.1 | | 2.245907821 | ENSG00000232563.1 | | 1.58266201 | ENSG00000222374.1 | | 1.26925486 |
| ENSG00000250171.1 | | 2.245315688 | ENSG00000269130.2 | CRB3P1 | 1.58116445 | ENSG00000260530.1 | | 1.2691955 |
| ENSG00000250315.2 | | 2.243463987 | ENSG00000233191.1 | | 1.58041435 | ENSG00000249183.1 | SUMO2P4 | 1.26875946 |
| ENSG00000277138.1 | MIR6509 | 2.242377246 | ENSG00000197172.9 | MAGEA6 | 1.57833832 | ENSG00000251574.5 | | 1.26833383 |

FIG. 1 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000130700.6 | GATA5 | 2.240152682 | ENSG00000265745.2 | RN7SL375P | 1.57550579 | ENSG00000224718.1 | | 1.26822015 |
| ENSG00000261210.4 | CLEC19A | 2.220571045 | ENSG00000243383.3 | RN7SL89P | 1.57399785 | ENSG00000233101.9 | HOXB-AS3 | 1.2681705 |
| ENSG00000178343.4 | SH3SA3 | 2.219632816 | ENSG00000199900.1 | RNA5SP463 | 1.57293759 | ENSG00000255972.1 | | 1.26796216 |
| ENSG00000266634.1 | MIR3972 | 2.206182964 | ENSG00000164893.7 | SLC7A13 | 1.57260126 | ENSG00000261722.1 | | 1.26686381 |
| ENSG00000229028.2 | KRT223P | 2.189554312 | ENSG00000242222.1 | | 1.56972214 | ENSG00000234228.1 | NCLP2 | 1.26652894 |
| ENSG00000227367.1 | SLC9B1P4 | 2.185693586 | ENSG00000242534.2 | IGKV2D-28 | 1.56931348 | ENSG00000253270.1 | | 1.26631362 |
| ENSG00000264764.1 | MIR4772 | 2.177221077 | ENSG00000268531.3 | | 1.56622696 | ENSG00000236733.1 | | 1.26393213 |
| ENSG00000267172.1 | | 2.17217087 | ENSG00000221174.1 | | 1.56270817 | ENSG00000259538.1 | UBE2Q2P11 | 1.26360546 |
| ENSG00000252591.1 | RNA5SP468 | 2.168623834 | ENSG00000242641.4 | LINC00971 | 1.56151209 | ENSG00000253819.1 | | 1.26027274 |
| ENSG00000230069.1 | | 2.162906731 | ENSG00000234593.1 | | 1.56148641 | ENSG00000258580.1 | LINC01151 | 1.25948156 |
| ENSG00000275373.1 | MIR6124 | 2.159967295 | ENSG00000254857.1 | | 1.56026405 | ENSG00000226434.1 | | 1.25833597 |
| ENSG00000218274.2 | | 2.158496526 | ENSG00000257835.1 | | 1.55551156 | ENSG00000184330.10 | S100A7A | 1.2579661 |
| ENSG00000221112.1 | | 2.156976203 | ENSG00000182585.8 | EPGN | 1.55083193 | ENSG00000263752.1 | MIR3133 | 1.25786495 |
| ENSG00000231866.2 | | 2.147569196 | ENSG00000207611.1 | MIR149 | 1.55075096 | ENSG00000237206.1 | IMPDH1P4 | 1.25551915 |
| ENSG00000226653.2 | OR13Z1P | 2.141191186 | ENSG00000093134.12 | VNN3 | 1.5502586 | ENSG00000258320.1 | | 1.25505569 |
| ENSG00000200113.1 | | 2.128348272 | ENSG00000268845.1 | | 1.54968711 | ENSG00000235350.1 | | 1.25466688 |
| ENSG00000105668.6 | UPK1A | 2.128018758 | ENSG00000215544.6 | BCRP7 | 1.54881956 | ENSG00000226996.4 | | 1.25445674 |
| ENSG00000169347.15 | GP2 | 2.12287273 | ENSG00000263427.1 | | 1.548622 | ENSG00000250781.1 | | 1.25243123 |
| ENSG00000260951.1 | | 2.109951007 | ENSG00000278479.1 | | 1.54849721 | ENSG00000278744.1 | | 1.25198878 |
| ENSG00000121270.14 | ABCC11 | 2.108691157 | ENSG00000169876.12 | MUC17 | 1.54781929 | ENSG00000266984.1 | POLR3GP2 | 1.25131305 |
| ENSG00000264265.1 | | 2.107972532 | ENSG00000230835.1 | | 1.54641466 | ENSG00000242019.1 | KIR3DL3 | 1.25089108 |
| ENSG00000170454.5 | KRT75 | 2.106658614 | ENSG00000234556.1 | LINC00701 | 1.54548598 | ENSG00000023044.1 | | 1.25087946 |
| ENSG00000262471.1 | | 2.101228585 | ENSG00000269502.4 | DMRTC1 | 1.54506446 | ENSG00000163220.10 | S100A9 | 1.25080967 |
| ENSG00000274400.2 | | 2.101219355 | ENSG00000227061.1 | | 1.54266078 | ENSG00000231758.2 | | 1.24914367 |
| ENSG00000261538.1 | | 2.094326401 | ENSG00000275011.1 | | 1.54029319 | ENSG00000270449.1 | | 1.24873377 |
| ENSG00000244659.2 | GAGE12J | 2.092451571 | ENSG00000274121.1 | | 1.53783684 | ENSG00000259852.2 | IGHV1OR16-2 | 1.24857444 |
| ENSG00000268847.1 | SIGLEC31P | 2.091902937 | ENSG00000228664.1 | | 1.53654853 | ENSG00000274380.1 | MIR6801 | 1.24763384 |
| ENSG00000275285.1 | | 2.083363504 | ENSG00000223189.1 | RNU6-177P | 1.5361945 | ENSG00000124490.12 | CRISP2 | 1.24387904 |
| ENSG00000264726.1 | | 2.083206028 | ENSG00000279087.1 | | 1.53067961 | ENSG00000249647.2 | C5orf66-AS2 | 1.24361733 |
| ENSG00000260963.1 | | 2.078830881 | ENSG00000272400.1 | | 1.5295104 | ENSG00000178445.8 | GLDC | 1.2433672 |
| ENSG00000244432.2 | RPL39P28 | 2.078363659 | ENSG00000224949.2 | | 1.5282028 | ENSG00000274395.1 | | 1.2432521 |
| ENSG00000254052.1 | IGHVIII-67-4 | 2.077841584 | ENSG00000230197.5 | | 1.52695942 | ENSG00000279665.1 | | 1.24254688 |

FIG. 1 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000256969.1 | | 2.076738291 | ENSG00000244122.2 | UGT1A7 | 1.52529142 | ENSG00000250575.1 | | 1.24245289 |
| ENSG00000254580.1 | KRTAP10-4 | 2.076497159 | ENSG00000171180.1 | OR2M4 | 1.52452356 | ENSG00000167346.6 | MMP26 | 1.24070898 |
| ENSG00000215454.5 | SPATA16 | 2.076322637 | ENSG00000254171.1 | | 1.51953229 | ENSG00000168333.12 | C8orf22 | 1.24039397 |
| ENSG00000144962.6 | GK2 | 2.074352934 | ENSG00000248850.1 | | 1.5177589 | ENSG00000250337.4 | LINC01021 | 1.23742914 |
| ENSG00000196475.5 | GNAI2P2 | 2.069810417 | ENSG00000280809.1 | LINC00836 | 1.51616649 | ENSG00000216675.1 | | 1.23725981 |
| ENSG00000231957.2 | ACSM1 | 2.069170328 | ENSG00000262081.2 | IL9RP4 | 1.5155559 | ENSG00000206159.9 | GYG2P1 | 1.23723558 |
| ENSG00000166743.8 | RLN3 | 2.064950248 | ENSG00000232765.5 | | 1.513484 | ENSG00000267035.1 | | 1.23690648 |
| ENSG00000171136.6 | | 2.061070222 | ENSG00000224382.1 | LINC00703 | 1.512601 | ENSG00000275620.1 | | 1.23637828 |
| ENSG00000248457.1 | PPBP | 2.0593281 | ENSG00000189001.9 | SBSN | 1.51237026 | ENSG00000254917.1 | OR7E15P | 1.2359373 |
| ENSG00000163736.3 | RPL7L1P5 | 2.052421869 | ENSG00000223436.1 | | 1.51144149 | ENSG00000276733.1 | MIR7158 | 1.23570103 |
| ENSG00000267634.1 | ANKS4B | 2.051479458 | ENSG00000221655.2 | | 1.508876 | ENSG00000259202.1 | | 1.23566654 |
| ENSG00000175311.6 | | 2.048003164 | ENSG00000233751.1 | | 1.50819548 | ENSG00000257431.1 | | 1.23562225 |
| ENSG00000221550.2 | TLR8-AS1 | 2.0432862 | ENSG00000270484.1 | | 1.50783199 | ENSG00000164399.4 | IL3 | 1.23526594 |
| ENSG00000233338.1 | | 2.041015998 | ENSG00000161031.11 | PGLYRP2 | 1.50620064 | ENSG00000236365.1 | | 1.2344719 |
| ENSG00000254957.1 | | 2.038462831 | ENSG00000204694.9 | OR11A1 | 1.50602148 | ENSG00000275978.1 | | 1.23414987 |
| ENSG00000257663.1 | | 2.027923963 | ENSG00000256927.1 | | 1.50597952 | ENSG00000237355.1 | | 1.234003 |
| ENSG00000247228.2 | CFHR4 | 2.021407377 | ENSG00000155890.3 | TRIM42 | 1.50557512 | ENSG00000205274.3 | TRBV20OR9-2 | 1.233698 |
| ENSG00000134365.11 | | 2.017301395 | ENSG00000242515.4 | UGT1A10 | 1.5049914 | ENSG00000261177.1 | | 1.23331312 |
| ENSG00000236212.1 | TRAJ26 | 2.009648257 | ENSG00000229112.1 | | 1.5032853 | ENSG00000105695.13 | MAG | 1.20085049 |
| ENSG00000203498.2 | | 2.003427554 | ENSG00000221989.2 | OR2A2 | 1.50034564 | ENSG00000228757.1 | | 1.23055228 |
| ENSG00000211863.1 | BCAN | 2.001207811 | ENSG00000230631.1 | | 1.50028784 | ENSG00000279929.1 | | 1.23045845 |
| ENSG00000243822.1 | LINC00552 | 1.989957019 | ENSG00000255093.1 | | 1.49989024 | ENSG00000224374.1 | | 1.22897363 |
| ENSG00000259164.1 | MYL1 | 1.989461135 | ENSG00000263450.1 | | 1.4982610 | ENSG00000272085.1 | | 1.22653225 |
| ENSG00000132692.17 | | 1.984516988 | ENSG00000269446.2 | | 1.49777888 | ENSG00000205649.6 | HTN3 | 1.22622958 |
| ENSG00000279770.1 | | 1.981770842 | ENSG00000276206.1 | | 1.49749669 | ENSG00000254761.1 | | 1.22538114 |
| ENSG00000168530.14 | | 1.98090785 | ENSG00000250422.1 | | 1.4957796 | ENSG00000254431.1 | | 1.22535176 |
| ENSG00000221356.1 | CD177P1 | 1.980598037 | ENSG00000275305.1 | | 1.49328949 | ENSG00000221263.1 | MIR548P | 1.22503872 |
| ENSG00000289979.1 | DNM1P34 | 1.978902596 | ENSG00000199934.1 | | 1.49322586 | ENSG00000255653.1 | | 1.22427814 |
| ENSG00000233970.1 | | 1.975049209 | ENSG00000134873.8 | CLDN10 | 1.49274759 | ENSG00000217372.2 | TUBB4BP7 | 1.22430338 |
| ENSG00000204933.3 | | 1.961481525 | ENSG00000255525.1 | | 1.49079787 | ENSG00000236689.1 | | 1.22359859 |
| ENSG00000260357.1 | | | ENSG00000233472.1 | | 1.4884828 | ENSG00000215397.3 | SCRT2 | 1.22256473 |
| ENSG00000254456.1 | | | ENSG00000256560.1 | LINC01486 | 1.48791684 | ENSG00000179817.4 | MRGPRX4 | 1.22239368 |

FIG. 1 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000226868.1 | | 1.960363882 | ENSG00000227274.1 | | 1.48761422 | ENSG00000238161.1 | OR7E117P | 1.22185453 |
| ENSG00000221601.1 | RNU4ATAC2P | 1.953315969 | ENSG00000229857.1 | | 1.48677259 | ENSG00000281721.1 | LINC01080 | 1.22162217 |
| ENSG00000198995.2 | MIR340 | 1.948294406 | ENSG00000254486.1 | | 1.48569254 | ENSG00000200527.1 | RNA5SP457 | 1.21919536 |
| ENSG00000235425.2 | RPS7P13 | 1.943507901 | ENSG00000237849.1 | NFYAP1 | 1.48566062 | ENSG00000239808.3 | RN7SL255P | 1.21646345 |
| ENSG00000278388.1 | | 1.942471711 | ENSG00000128510.9 | CPA4 | 1.48342315 | ENSG00000263356.1 | | 1.21618052 |
| ENSG00000265064.1 | MIR4692 | 1.937451338 | ENSG00000280890.1 | ELDR | 1.479572226 | ENSG00000266125.1 | | 1.21600743 |
| ENSG00000103316.9 | CRYM | 1.9367535 | ENSG00000272874.1 | | 1.475909929 | ENSG00000176728.6 | TTTY14 | 1.2154192 |
| ENSG00000269908.1 | | 1.92612688 | ENSG00000255522.1 | SNRPCP5 | 1.47587963 | ENSG00000235303.1 | | 1.21525792 |
| ENSG00000277665.1 | | 1.925666092 | ENSG00000256661.1 | A2ML1-AS1 | 1.47569956 | ENSG00000266423.1 | MIR3163 | 1.21520433 |
| ENSG00000255555.1 | | 1.922018332 | ENSG00000257281.1 | | 1.47203998 | ENSG00000233491.5 | | 1.21470447 |
| ENSG00000227713.1 | | 1.918690249 | ENSG00000262983.1 | | 1.46945056 | ENSG00000226733.1 | | 1.21433806 |
| ENSG00000198854.5 | C1orf68 | 1.904520599 | ENSG00000205396.10 | LINC00661 | 1.46641176 | ENSG00000264614.1 | MIR5588 | 1.21350322 |
| ENSG00000236556.1 | | 1.902691727 | ENSG00000261606.4 | | 1.46507093 | ENSG00000143536.7 | CRNN | 1.21276944 |
| ENSG00000267072.1 | | 1.901048964 | ENSG00000229306.1 | | 1.46397128 | ENSG00000173237.4 | C11orf86 | 1.21208084 |
| ENSG00000271099.1 | | 1.90021343 | ENSG00000230272.1 | | 1.46274169 | ENSG00000237674.1 | GSTA7P | 1.21204334 |
| ENSG00000266318.1 | MIR5692A1 | 1.895344401 | ENSG00000229941.4 | | 1.45471939 | ENSG00000224850.1 | | 1.21168816 |
| ENSG00000233036.1 | KRTAP8-2P | 1.895185239 | ENSG00000253821.1 | | 1.451737699 | ENSG00000213231.11 | TCL1B | 1.21063149 |
| ENSG00000276427.1 | IGLL4P | 1.891813246 | ENSG00000199240.1 | RNA5SP46 | 1.45153713 | ENSG00000240577.3 | RN7SL445P | 1.20999279 |
| ENSG00000279877.1 | | 1.859924161 | ENSG00000212556.1 | | 1.4513894 | ENSG00000229314.5 | ORM1 | 1.20904406 |
| ENSG00000230663.1 | FAM224B | 1.889733282 | ENSG00000255007.1 | | 1.44951016 | ENSG00000158022.6 | TRIM63 | 1.20831954 |
| ENSG00000261239.5 | ANKRD26P1 | 1.884585216 | ENSG00000242111.1 | TOPORSLP | 1.44835365 | ENSG00000203266.2 | | 1.20823025 |
| ENSG00000265416.1 | | 1.880809555 | ENSG00000251107.1 | | 1.44486905 | ENSG00000279782.1 | PPIAL4F | 1.20808746 |
| ENSG00000264357.1 | MIR4648 | 1.876745207 | ENSG00000282234.1 | | 1.448660959 | ENSG00000268863.2 | RN7SL123P | 1.20726403 |
| ENSG00000253937.1 | NATP | 1.875175142 | ENSG00000237939.1 | | 1.44829775 | ENSG00000281131.1 | SCHLAP1 | 1.2062892 |
| ENSG00000225325.1 | | 1.870770552 | ENSG00000275243.1 | TRBV16 | 1.44712824 | ENSG00000235964.1 | FXYD6P2 | 1.20583101 |
| ENSG00000225117.1 | ARSDP1 | 1.866743373 | ENSG00000227573.2 | | 1.446236 | ENSG00000185203.10 | WASIR1 | 1.2047087 |
| ENSG00000206532.2 | | 1.865532014 | ENSG00000251516.1 | | 1.44146167 | ENSG00000260239.1 | | 1.20449593 |
| ENSG00000247345.2 | | 1.860252718 | ENSG00000230226.1 | | 1.44079116 | ENSG00000233236.1 | | 1.20436939 |
| ENSG00000199566.1 | | 1.856424464 | ENSG00000134249.6 | ADAM30 | 1.43912482 | ENSG00000232889.2 | | 1.20323264 |
| | | | ENSG00000267636.1 | | 1.43627912 | ENSG00000261453.1 | | 1.20079022 |

FIG. 2

| Gene_id | Gene_name | log(FC) | Gene_id | Gene_name | log(FC) | Gene_id | Gene_name | log(FC) |
|---|---|---|---|---|---|---|---|---|
| ENSG00000135220.9 | UGT2A3 | -5.4399454 | ENSG00000231508.1 | | -1.9378319 | ENSG00000241318.3 | WDR82P2 | -1.4519411 |
| ENSG00000258244.1 | OSTFIP1 | -5.3590176 | ENSG00000229169.1 | | -1.9374211 | ENSG00000230121.1 | | -1.4519214 |
| ENSG00000265547.1 | | -5.0783608 | ENSG00000228937.1 | | -1.9372133 | ENSG00000280345.1 | | -1.4512157 |
| ENSG00000225280.5 | | -4.8679167 | ENSG00000264721.1 | | -1.9365126 | ENSG00000235325.1 | | -1.4512055 |
| ENSG00000265736.1 | | -4.776944 | ENSG00000220694.2 | | -1.9364818 | ENSG00000256739.1 | | -1.4511595 |
| ENSG00000232944.1 | | -4.7032479 | ENSG00000232638.1 | | -1.9340579 | ENSG00000243053.2 | RPL31PS8 | -1.4506976 |
| ENSG00000235224.1 | | -4.6572348 | ENSG00000223156.1 | RNU2-18P | -1.9337789 | ENSG00000263993.2 | RN7SL786P | -1.450467 |
| ENSG00000240012.1 | SLC9A9-AS1 | -4.4598768 | ENSG00000124157.6 | SEMG2 | -1.9322187 | ENSG00000234938.2 | | -1.4502171 |
| ENSG00000261020.1 | | -4.350986 | ENSG00000252972.1 | RNA5SP398 | -1.9280961 | ENSG00000232825.1 | | -1.4485686 |
| ENSG00000281472.1 | | -4.3377927 | ENSG00000199203.1 | | -1.9280172 | ENSG00000264796.1 | MIR5009 | -1.4485089 |
| ENSG00000206977.1 | | -4.2844886 | ENSG00000259361.4 | LINC00927 | -1.9274759 | ENSG00000252748.1 | | -1.4477298 |
| ENSG00000278060.1 | | -4.2287335 | ENSG00000264455.1 | | -1.9254232 | ENSG00000237596.5 | | -1.447635 |
| ENSG00000248155.1 | | -4.1908337 | ENSG00000238417.1 | RNU7-63P | -1.9245114 | ENSG00000199072.2 | MIRLET7F1 | -1.44695 |
| ENSG00000226337.3 | | -4.167719 | ENSG00000253359.1 | | -1.922808 | ENSG00000257649.1 | METTL7AP1 | -1.4461819 |
| ENSG00000273926.1 | | -4.1644946 | ENSG00000261146.1 | | -1.9206797 | ENSG00000244244.2 | RPS3AP42 | -1.445908 |
| ENSG00000238888.2 | | -4.1157808 | ENSG00000241961.1 | | -1.9201177 | ENSG00000261411.1 | | -1.4455882 |
| ENSG00000254187.1 | | -4.1097398 | ENSG00000224808.1 | SRGAP3-AS1 | -1.9195727 | ENSG00000261472.1 | | -1.4449326 |
| ENSG00000125816.4 | NKX2-4 | -4.0388455 | ENSG00000277575.1 | | -1.9194856 | ENSG00000251128.1 | HSPD1P3 | -1.4446875 |
| ENSG00000252186.1 | RNU6-781P | -4.0341986 | ENSG00000225546.4 | | -1.9187506 | ENSG00000211859.1 | TRAJ30 | -1.4446439 |
| ENSG00000238079.1 | | -4.0318507 | ENSG00000244247.1 | | -1.9158441 | ENSG00000236274.1 | | -1.4428086 |
| ENSG00000200355.1 | | -4.0083157 | ENSG00000249004.1 | PRMT5P1 | -1.9138479 | ENSG00000261179.2 | | -1.4424768 |
| ENSG00000280280.1 | | -3.9986362 | ENSG00000196772.3 | OR14A16 | -1.9131929 | ENSG00000251605.1 | | -1.4421923 |
| ENSG00000281653.1 | | -3.9910128 | ENSG00000243986.2 | ENO1P3 | -1.9109686 | ENSG00000168267.5 | PTF1A | -1.4420422 |
| ENSG00000225299.1 | | -3.9832323 | ENSG00000278698.1 | | -1.9106734 | ENSG00000228872.2 | | -1.4419241 |
| ENSG00000230871.1 | RPS6P23 | -3.9446715 | ENSG00000168824.13 | | -1.9100106 | ENSG00000273632.1 | | -1.4417137 |
| ENSG00000254878.1 | | -3.8876088 | ENSG00000248216.1 | KCTD9P5 | -1.9088342 | ENSG00000162374.15 | ELAVL4 | -1.4412774 |
| ENSG00000252210.1 | | -3.8770487 | ENSG00000081842.16 | PCDHA6 | -1.9076469 | ENSG00000277997.1 | | -1.4412169 |
| ENSG00000207963.1 | MIR569 | -3.8681605 | ENSG00000265850.1 | MIR4797 | -1.9032391 | ENSG00000273877.3 | | -1.4407581 |
| ENSG00000232827.2 | LINC01189 | -3.8551174 | ENSG00000230481.2 | IGKV1OR22-5 | -1.9013691 | ENSG00000249860.3 | MTRNR2L5 | -1.4406021 |
| ENSG00000222164.1 | RN7SKP266 | -3.8499351 | ENSG00000234503.1 | | -1.9000946 | ENSG00000279750.2 | | -1.4403904 |
| ENSG00000250884.1 | OR7E85P | -3.8385858 | ENSG00000226240.1 | LINC00381 | -1.8997943 | ENSG00000232282.1 | MTND1P32 | -1.4400982 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000266100.1 | | -3.8336607 | ENSG00000185264.10 | TEX33 | -1.899776 | ENSG00000250619.1 | | -1.4397473 |
| ENSG00000253039.1 | RNA5SP47 | -3.8221163 | ENSG00000253507.4 | | -1.8987145 | ENSG00000228725.3 | MTND2P12 | -1.4387386 |
| ENSG00000241119.1 | UGT1A9 | -3.8184975 | ENSG00000164299.6 | SPZ1 | -1.8984974 | ENSG00000230748.2 | | -1.438457 |
| ENSG00000214978.7 | | -3.8156536 | ENSG00000244666.1 | | -1.8977036 | ENSG00000171487.13 | NLRP5 | -1.4381094 |
| ENSG00000199512.1 | RNU6-212P | -3.8079443 | ENSG00000270639.1 | ECM1P1 | -1.8946173 | ENSG00000249731.1 | | -1.4378283 |
| ENSG00000248295.2 | DDX43P1 | -3.8071712 | ENSG00000229108.1 | MEOX2-AS1 | -1.8919369 | ENSG00000163202.4 | LCE3D | -1.4361656 |
| ENSG00000269509.1 | BNIP3P34 | -3.7864902 | ENSG00000212360.1 | RNU6-1177P | -1.8916268 | ENSG00000224852.1 | MTND5P24 | -1.4355719 |
| ENSG00000241546.1 | | -3.7561069 | ENSG00000280954.1 | | -1.8891136 | ENSG00000238267.1 | | -1.4351268 |
| ENSG00000181211.1 | HECW1-IT1 | -3.7528753 | ENSG00000202071.1 | | -1.8887722 | ENSG00000094796.4 | KRT31 | -1.4350225 |
| ENSG00000276031.1 | RN7SL197P | -3.7474986 | ENSG00000239504.3 | RN7SL583P | -1.8883026 | ENSG00000212329.1 | RNU6-316P | -1.4345354 |
| ENSG00000225181.1 | | -3.7466837 | ENSG00000227785.1 | | -1.888275 | ENSG00000239118.1 | MIR1972-2 | -1.434456 |
| ENSG00000219770.1 | VN1R11P | -3.688401 | ENSG00000198914.2 | POU3F3 | -1.886874 | ENSG00000274019.1 | | -1.4342726 |
| ENSG00000258928.1 | | -3.6864273 | ENSG00000264813.4 | | -1.8863402 | ENSG00000230657.5 | PRB4 | -1.4339833 |
| ENSG00000250259.1 | | -3.6836064 | ENSG00000253365.1 | IGKV1D-22 | -1.8845753 | ENSG00000207251.1 | RNU6-342P | -1.4330482 |
| ENSG00000222958.1 | MIR1913 | -3.6824086 | ENSG00000281514.1 | | -1.8838225 | ENSG00000212170.1 | RNU1-77P | -1.4329604 |
| ENSG00000279912.1 | | -3.6715241 | ENSG00000259199.1 | | -1.8837388 | ENSG00000266063.1 | MIR4771-2 | -1.4325968 |
| ENSG00000222714.1 | RN7SKP38 | -3.6426763 | ENSG00000278001.1 | | -1.8802215 | ENSG00000281727.1 | | -1.432357 |
| ENSG00000260551.1 | PWRN2 | -3.6392897 | ENSG00000211654.2 | IGLV5-37 | -1.8791338 | ENSG00000231361.1 | | -1.4319815 |
| ENSG00000278255.1 | | -3.6327143 | ENSG00000230902.1 | FAM204CP ARHGAP22-IT1 | -1.8784943 | ENSG00000182450.11 | KCNK4 | -1.4318557 |
| ENSG00000267797.1 | NRBF2P1 | -3.6272712 | ENSG00000248682.1 | | -1.8765036 | ENSG00000270421.1 | | -1.4318119 |
| ENSG00000251435.1 | C1GALT1P2 | -3.5914156 | ENSG00000250564.1 | | -1.8740048 | ENSG00000202512.1 | RN7SKP230 | -1.4306858 |
| ENSG00000257078.1 | RNU6-608P | -3.5771882 | ENSG00000265843.2 | LINC01029 | -1.8735363 | ENSG00000257094.1 | | -1.4306399 |
| ENSG00000166509.9 | CLEC3A | -3.568865 | ENSG00000243287.2 | RPS17P14 | -1.8731968 | ENSG00000279126.1 | | -1.4302727 |
| ENSG00000235390.4 | | -3.5477624 | ENSG00000259664.2 | | -1.8724706 | ENSG00000253868.3 | FER1L6-AS2 | -1.4285294 |
| ENSG00000227301.1 | | -3.5340462 | ENSG00000254031.4 | | -1.8711905 | ENSG00000256597.2 | | -1.4270421 |
| ENSG00000177144.6 | NUDT4P1 | -3.5272262 | ENSG00000211834.1 | TRAJ57 | -1.8701662 | ENSG00000222679.1 | RNU6-1267P | -1.4266775 |
| ENSG00000206654.1 | RNU6-608P | -3.5245089 | ENSG00000265636.1 | | -1.8683609 | ENSG00000252132.1 | RNU6-795P | -1.4263189 |
| ENSG00000265693.1 | | -3.5175583 | ENSG00000249807.1 | | -1.8654109 | ENSG00000257121.1 | | -1.4254809 |
| ENSG00000244422.3 | RPL38P3 | -3.5174258 | ENSG00000219384.1 | | -1.8652667 | ENSG00000279410.1 | | -1.4245731 |
| ENSG00000254939.1 | | -3.5039733 | ENSG00000267393.1 | | -1.863549 | ENSG00000248956.1 | HMGB1P44 | -1.4243443 |
| ENSG00000261696.1 | | -3.4972691 | ENSG00000237445.2 | | -1.86261 | ENSG00000235616.1 | ST13P2 | -1.424298 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000235849.1 | HS6ST2-AS1 | -3.4755795 | ENSG00000206856.1 | RNU6-427P | -1.8602748 | ENSG00000280365.1 | | -1.4238734 |
| ENSG00000250383.1 | | -3.474937 | ENSG00000250360.1 | | -1.8599333 | ENSG00000180105.13 | | -1.4235432 |
| ENSG00000202341.1 | RNU6-1051P | -3.4697025 | ENSG00000271831.1 | | -1.8592218 | ENSG00000216636.1 | RPL7P25 | -1.4229933 |
| ENSG00000275114.1 | | -3.4505061 | ENSG00000263497.2 | | -1.8538617 | ENSG00000261095.1 | | -1.4228418 |
| ENSG00000244236.3 | RN7SL604P | -3.4419731 | ENSG00000254865.1 | | -1.8584706 | ENSG00000206961.1 | | -1.4223396 |
| ENSG00000239179.1 | | -3.4351437 | ENSG00000198704.8 | GPX6 | -1.8581549 | ENSG00000222351.1 | RNY1P15 | -1.4213096 |
| ENSG00000267591.1 | | -3.4296371 | ENSG00000266196.1 | | -1.8575104 | ENSG00000261446.2 | LINC00559 | -1.4205951 |
| ENSG00000233777.1 | | -3.3690318 | ENSG00001139200.12 | PIANP | -1.8562239 | ENSG00000261786.1 | | -1.4188309 |
| ENSG00000235379.1 | RPL7P31 | -3.3684858 | ENSG00000267587.1 | | -1.8560915 | ENSG00000277118.1 | | -1.4181396 |
| ENSG00000250198.1 | | -3.3594018 | ENSG00000224363.2 | | -1.8542195 | ENSG00000240927.3 | RN7SL209P | -1.4180735 |
| ENSG00000206887.1 | RNU6-1008P | -3.3547125 | ENSG00000272967.1 | | -1.8530716 | ENSG00000225605.1 | | -1.4178847 |
| ENSG00000252636.1 | RNU6-826P | -3.352687 | ENSG00000256218.1 | | -1.8504713 | ENSG00000206683.1 | RNU6-379P | -1.4178374 |
| ENSG00000164326.4 | CARTPT | -3.3492287 | ENSG00000268659.2 | | -1.8500497 | ENSG00000233997.4 | LINC01425 | -1.4172138 |
| ENSG00000230595.1 | RSL24D1P2 | -3.3343686 | ENSG00000206925.1 | | -1.8500421 | ENSG00000232543.2 | IGHD4-11 | -1.4168889 |
| ENSG00000277759.2 | VTI1BP4 | -3.3263066 | ENSG00000121335.11 | PRB2 | -1.8500293 | ENSG00000230044.1 | | -1.4164827 |
| ENSG00000252146.1 | | -3.3261003 | ENSG00000255005.1 | | -1.8491204 | ENSG00000223238.1 | RNA5SP294 | -1.4159473 |
| ENSG00000202417.1 | | -3.3128393 | ENSG00000260029.2 | | -1.8488619 | ENSG00000211578.2 | MIR766 | -1.4154663 |
| ENSG00000253659.1 | | -3.3073874 | ENSG00000224391.1 | LINC01280 | -1.8482923 | ENSG00000229115.1 | | -1.4147399 |
| ENSG00000239923.3 | RN7SL864P | -3.2963643 | ENSG00000255344.1 | | -1.8464921 | ENSG00000251209.6 | LINC00923 | -1.4141055 |
| ENSG00000227243.3 | SLAMF6P1 | -3.2957571 | ENSG00000217514.1 | | -1.8458636 | ENSG00000264309.1 | MIR4694 | -1.4140817 |
| ENSG00000281613.1 | | -3.2858481 | ENSG00000255256.1 | | -1.8439859 | ENSG00000263302.4 | | -1.4140275 |
| ENSG00000228503.1 | | -3.2761441 | ENSG00000254143.1 | | -1.8428149 | ENSG00000255924.1 | | -1.4138143 |
| ENSG00000265992.1 | ESRG | -3.2740328 | ENSG00000207005.1 | RNU1-2 | -1.841969 | ENSG00000251579.1 | | -1.4131339 |
| ENSG00000127780.3 | OR1E2 | -3.2662667 | ENSG00000212479.2 | | -1.841449 | ENSG00000221216.1 | RNU6ATAC27P | -1.4123624 |
| ENSG00000197468.5 | | -3.2627355 | ENSG00000201867.1 | | -1.8405191 | ENSG00000207708.1 | MIR141 | -1.4120864 |
| ENSG00000271647.1 | KRT8P47 | -3.2590869 | ENSG00000273631.1 | | -1.8400086 | ENSG00000270620.1 | | -1.4114739 |
| ENSG00000229330.2 | | -3.2572355 | ENSG00000253993.1 | | -1.8388224 | ENSG00000238081.1 | | -1.4100712 |
| ENSG00000222094.1 | RNU2-65P | -3.2564861 | ENSG00000229452.1 | | -1.8384011 | ENSG00000267656.1 | | -1.4100416 |
| ENSG00000238201.1 | | -3.249215 | ENSG00000229733.1 | | -1.83767 | ENSG00000238604.1 | | -1.4098895 |
| ENSG00000214617.8 | SLC6A10P | -3.2479368 | ENSG00000234887.1 | | -1.8371812 | ENSG00000255672.1 | | -1.4098444 |
| ENSG00000222182.1 | RNA5SP156 | -3.2449975 | ENSG00000264102.1 | MIR4688 | -1.8369408 | ENSG00000238607.2 | CLDN25 | -1.4092924 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000276588.1 | RN7SL322P | -3.2427302 | ENSG00000263015.1 | | -1.8367013 | ENSG00000150244.11 | TRIM48 | -1.4089567 |
| ENSG00000284467.2 | | -3.2400341 | ENSG00000266050.2 | | -1.8332553 | ENSG00000225652.1 | KCNMA1-AS3 | -1.4082597 |
| ENSG00000211849.1 | TRAJ40 | -3.2207933 | ENSG00000226516.6 | FAM138B | -1.8323979 | ENSG00000199890.1 | | -1.4081512 |
| ENSG00000252062.1 | RNU6-469P | -3.2158155 | ENSG00000157890.16 | MEGF11 | -1.8320206 | ENSG00000222533.1 | RNU6-705P | -1.4075164 |
| ENSG00000265541.1 | H3F3BP2 | -3.2095685 | ENSG00000237063.1 | | -1.8318471 | ENSG00000274559.2 | | -1.4074458 |
| ENSG00000260115.1 | | -3.2045044 | ENSG00000227261.1 | YWHAZP7 | -1.8314685 | ENSG00000212432.3 | | -1.4070172 |
| ENSG00000252764.1 | RNU6-1092P | -3.201227 | ENSG00000241832.1 | CECR3 | -1.831379 | ENSG00000248150.1 | | -1.466788 |
| ENSG00000258742.4 | | -3.1816322 | ENSG00000239228.3 | RN7SL578P | -1.8306634 | ENSG00000258531.2 | BANF1P1 | -1.4066316 |
| ENSG00000248977.1 | | -3.1782279 | ENSG00000273214.1 | | -1.83045307 | ENSG00000273904.1 | | -1.4065506 |
| ENSG00000184735.6 | DDX53 | -3.1607758 | ENSG00000104938.15 | CLEC4M | -1.8291344 | ENSG00000225769.1 | CROCCP1 | -1.4059542 |
| ENSG00000223977.1 | | -3.151842 | ENSG00000229913.1 | | -1.8284963 | ENSG00000275803.1 | RN7SL736P | -1.4059081 |
| ENSG00000250684.4 | | -3.1514478 | ENSG00000265813.2 | RN7SL300P | -1.8270781 | ENSG00000226761.3 | TAS2R-46 | -1.4055433 |
| ENSG00000227718.1 | | -3.1514228 | ENSG00000256734.1 | | -1.82597 | ENSG00000260487.1 | | -1.4047902 |
| ENSG00000254734.1 | | -3.1506026 | ENSG00000253760.1 | | -1.8227441 | ENSG00000270082.1 | | -1.4046499 |
| ENSG00000231934.1 | LINC01598 | -3.1463539 | ENSG00000186971.3 | KRTAP13-4 | -1.8189405 | ENSG00000177414.12 | UBE2U | -1.4046367 |
| ENSG00000264741.1 | MIR4505 | -3.1362746 | ENSG00000222586.1 | | -1.8181478 | ENSG00000139223.2 | ANP32D | -1.404107 |
| ENSG00000203434.2 | | -3.1298715 | ENSG00000218749.1 | | -1.8175089 | ENSG00000153802.10 | TMPRSS11D | -1.4037298 |
| ENSG00000251452.2 | | -3.1288438 | ENSG00000215182.8 | MUC5AC | -1.8156557 | ENSG00000165970.10 | SLC6A5 | -1.4035483 |
| ENSG00000260857.2 | | -3.1284198 | ENSG00000222375.1 | RN7SKP127 | -1.815032 | ENSG00000281724.1 | | -1.4032154 |
| ENSG00000218107.1 | | -3.1274874 | ENSG00000184906.8 | | -1.8149399 | ENSG00000236693.1 | | -1.4028504 |
| ENSG00000266799.1 | | -3.1264805 | ENSG00000252940.2 | | -1.8133018 | ENSG00000251039.2 | IGKV2D-40 | -1.4025141 |
| ENSG00000279223.1 | | -3.1245974 | ENSG00000269839.1 | | -1.8111103 | ENSG00000277529.1 | NF1P10 | -1.4019294 |
| ENSG00000264135.1 | | -3.1242793 | ENSG00000279498.1 | | -1.810984 | ENSG00000165702.11 | GF1JB | -1.4017404 |
| ENSG00000239396.3 | RN7SL414P | -3.1152462 | ENSG00000248747.1 | | -1.809908 | ENSG00000274198.1 | | -1.4015908 |
| ENSG00000236672.2 | | -3.1103764 | ENSG00000236004.2 | | -1.8097237 | ENSG00000258418.1 | | -1.4010138 |
| ENSG00000201367.1 | RNU6-522P | -3.1040643 | ENSG00000199733.1 | RNA5SP307 | -1.8094529 | ENSG00000182261.3 | NLRP10 | -1.4009543 |
| ENSG00000242810.1 | MRPL42P6 | -3.0909089 | ENSG00000233420.1 | | -1.8084744 | ENSG00000148798.8 | INA | -1.4007318 |
| ENSG00000261826.1 | | -3.0896831 | ENSG00000267872.1 | | -1.8083346 | ENSG00000255608.1 | | -1.460566 |
| ENSG00000232032.1 | | -3.0867132 | ENSG00000185448.10 | FAM47A | -1.8068285 | ENSG00000248528.1 | | -1.4001483 |
| ENSG00000279646.1 | | -3.0838977 | ENSG00000251283.1 | | -1.8048652 | ENSG00000241420.3 | RN7SL505P | -1.3993232 |
| ENSG00000248172.1 | | -3.0837872 | ENSG00000243350.1 | | -1.8037768 | ENSG00000185269.10 | NOTUM | -1.399145 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000267857.2 | | -3.083352 | ENSG00000252339.1 | RNU6-1061P | -1.8036937 | ENSG00000236678.6 | LINC00347 | -1.3988799 |
| ENSG00000249057.1 | MAST4-IT1 | -3.0779517 | ENSG00000251105.1 | | -1.8034163 | ENSG00000217488.2 | | -1.3986427 |
| ENSG00000228295.1 | LINC00392 | -3.0707139 | ENSG00000186191.7 | BPIFB4 | -1.8027207 | ENSG00000230379.4 | | -1.3985106 |
| ENSG00000271167.1 | | -3.069658 | ENSG00000271477.1 | | -1.8023293 | ENSG00000223138.1 | RNA5SP450 | -1.3983278 |
| ENSG00000258672.1 | | -3.0682353 | ENSG00000207023.1 | RNU6-975P | -1.802277 | ENSG00000254547.1 | | -1.3980429 |
| ENSG00000199944.1 | RNU6-653P | -3.0623241 | ENSG00000233311.1 | | -1.8016079 | ENSG00000258480.1 | | -1.397462 |
| ENSG00000207134.1 | RNU6-106P | -3.0591306 | ENSG00000226597.1 | IFNWP9 | -1.8003757 | ENSG00000271052.1 | | -1.3972729 |
| ENSG00000252971.1 | RNU6-1057P | -3.0417332 | ENSG00000273957.1 | | -1.7986695 | ENSG00000279793.1 | | -1.3967044 |
| ENSG00000187664.8 | HAPLN4 | -3.0309876 | ENSG00000149021.5 | SCGB1A1 | -1.7980739 | ENSG00000235564.1 | | -1.3956983 |
| ENSG00000228778.1 | | -3.0300907 | ENSG00000264114.1 | | -1.7975393 | ENSG00000166589.11 | CDH16 | -1.3955226 |
| ENSG00000266888.1 | | -3.0267072 | ENSG00000279962.1 | | -1.7968324 | ENSG00000180305.4 | WFDC10A | -1.395443 |
| ENSG00000240888.1 | | -3.0249793 | ENSG00000128713.12 | HOXD11 | -1.7962165 | ENSG00000264181.1 | | -1.395439 |
| ENSG00000237658.1 | | -3.0228965 | ENSG00000223815.1 | DIAPH3-AS2 | -1.7961004 | ENSG00000250576.1 | | -1.3954008 |
| ENSG00000258271.1 | MIR181B2 | -3.0186376 | ENSG00000144820.6 | ADGRG7 | -1.7942175 | ENSG00000231163.4 | CSMD2-AS1 | -1.394667 |
| ENSG00000279325.1 | | -3.017998 | ENSG00000255745.1 | | -1.7937877 | ENSG00000225625.4 | | -1.3941918 |
| ENSG00000200665.1 | RNU6-1388P | -3.0056759 | ENSG00000279363.1 | | -1.7929068 | ENSG00000226792.5 | LINC00371 | -1.3940312 |
| ENSG00000281037.1 | | -2.994883 | ENSG00000222594.1 | RN7SKP235 | -1.79236 | ENSG00000235548.1 | | -1.3936193 |
| ENSG00000279366.1 | | -2.9899078 | ENSG00000233993.1 | | -1.7902003 | ENSG00000266043.1 | MIR3649 | -1.3930969 |
| ENSG00000207737.1 | | -2.9847311 | ENSG00000221409.1 | | -1.7899702 | ENSG00000265110.1 | MIR4731 | -1.3926927 |
| ENSG00000270969.1 | | -2.9830269 | ENSG00000252578.1 | RNU6-135P | -1.7885368 | ENSG00000277573.1 | | -1.3919361 |
| ENSG00000253992.1 | | -2.9802388 | ENSG00000267620.1 | | -1.787742 | ENSG00000261340.1 | | -1.3916546 |
| ENSG00000185053.11 | SGCZ | -2.980137 | ENSG00000253020.2 | RN7SKP40 | -1.7874534 | ENSG00000211649.3 | IGLV7-46 | -1.3916405 |
| ENSG00000233440.2 | HMGA1P6 | -2.9705277 | ENSG00000174453.8 | VWC2L | -1.7873988 | ENSG00000189030.9 | VHLL | -1.3915732 |
| ENSG00000241926.1 | | -2.9703389 | ENSG00000265804.1 | | -1.7872126 | ENSG00000254522.1 | | -1.3913345 |
| ENSG00000214823.3 | NXT1P1 | -2.9499544 | ENSG00000200261.1 | MT4 | -1.7870928 | ENSG00000187823.3 | ZCCHC16 | -1.3910839 |
| ENSG00000239825.3 | RN7SL549P | -2.9484439 | ENSG00000102891.3 | | -1.787064 | ENSG00000270682.1 | | -1.3905714 |
| ENSG00000228636.1 | | -2.9485619 | ENSG00000233548.1 | CYCSP44 | -1.7870183 | ENSG00000263537.2 | RN7SL387P | -1.3903534 |
| ENSG00000261623.1 | | -2.9476928 | ENSG00000231562.1 | | -1.7869326 | ENSG00000270474.1 | IGHV3-29 | -1.3902267 |
| ENSG00000253059.1 | | -2.9417468 | ENSG00000119698.10 | PPP4R4 | -1.7852803 | ENSG00000279567.1 | | -1.3900462 |
| ENSG00000278860.1 | | -2.9412496 | ENSG00000177354.10 | C16orf71 | -1.7835253 | ENSG00000275940.1 | | -1.3899814 |
| ENSG00000237042.1 | MICG | -2.9386177 | ENSG00000235858.1 | | -1.7822436 | ENSG00000218730.1 | | -1.3898851 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000253687.1 | | -2.9361147 | ENSG00000213180.4 | RPL36AP48 | -1.7813863 | ENSG00000230312.2 | | -1.3892115 |
| ENSG00000274455.1 | | -2.926451 | ENSG00000212226.1 | RNU6-907P | -1.78096675 | ENSG00000277588.1 | MIR6806 | -1.3889407 |
| ENSG00000248935.1 | | -2.9224921 | ENSG00000258784.1 | | -1.7794485 | ENSG00000236863.2 | RPL23AP23 | -1.3887146 |
| ENSG00000242256.3 | RN7SL57P | -2.9122955 | ENSG00000237325.3 | | -1.7780545 | ENSG00000260706.4 | | -1.3878585 |
| ENSG00000264831.1 | MIR4260 | -2.9075751 | ENSG00000145309.5 | CABS1 | -1.7774779 | ENSG00000266466.1 | | -1.387665 |
| ENSG00000186825.5 | C2orf27B | -2.8972661 | ENSG00000266058.1 | | -1.7772795 | ENSG00000202385.1 | | -1.3874665 |
| ENSG00000264475.1 | | -2.8958154 | ENSG00000263988.2 | RN7SL147P | -1.777017 | ENSG00000141431.8 | ASXL3 | -1.3870649 |
| ENSG00000249808.2 | LINC01377 | -2.894364 | ENSG00000224731.1 | | -1.7766507 | ENSG00000243144.5 | | -1.386626 |
| ENSG00000236121.1 | HAUS6P2 | -2.8934515 | ENSG00000248522.1 | SBF1P1 | -1.7752648 | ENSG00000263287.1 | | -1.3862739 |
| ENSG00000218766.1 | | -2.8917673 | ENSG00000264476.2 | | -1.775029 | ENSG00000200691.1 | RN7SKP163 | -1.3858857 |
| ENSG00000265291.1 | MIR4710 | -2.8896508 | ENSG00000255219.1 | | -1.7738867 | ENSG00000275064.1 | | -1.3858388 |
| ENSG00000205665.2 | | -2.8856979 | ENSG00000147381.10 | MAGEA4 | -1.7722719 | ENSG00000275770.1 | MIR6505 | -1.38555 |
| ENSG00000278424.1 | | -2.8846743 | ENSG00000253563.2 | NKX2-1-AS1 | -1.722151 | ENSG00000261624.1 | | -1.3853308 |
| ENSG00000264519.2 | RN7SL596P | -2.8844327 | ENSG00000237569.1 | TUBAP | -1.771965 | ENSG00000199567.1 | | -1.3849116 |
| ENSG00000240427.1 | RPS26P34 | -2.8837163 | ENSG00000275849.1 | | -1.770823 | ENSG00000227776.1 | AKR1D1P1 | -1.3830714 |
| ENSG00000145879.9 | SPINK7 | -2.8734275 | ENSG00000230818.1 | MTND2P16 | -1.770573 | ENSG00000253416.1 | | -1.3819166 |
| ENSG00000241231.1 | | -2.8761093 | ENSG00000249958.1 | CCT7P2 | -1.7700314 | ENSG00000138068.9 | SULT6B1 | -1.3815583 |
| ENSG00000196406.4 | SPANXD | -2.8703416 | ENSG00000202054.1 | RNASSP152 | -1.7692836 | ENSG00000259026.1 | | -1.3813538 |
| ENSG00000228648.1 | | -2.8696422 | ENSG00000258783.1 | KRT18P6 | -1.7671997 | ENSG00000280350.1 | | -1.3805783 |
| ENSG00000225785.1 | | -2.8668646 | ENSG00000115934.11 | | -1.7652069 | ENSG00000225530.1 | SP3P | -1.3790999 |
| ENSG00000242329.1 | | -2.8560133 | ENSG00000237162.1 | | -1.7643999 | ENSG00000279440.1 | | -1.3789284 |
| ENSG00000201511.1 | | -2.8560092 | ENSG00000265174.1 | | -1.7642591 | ENSG00000254596.1 | | -1.3788839 |
| ENSG00000259196.1 | HMBOX1-IT1 | -2.8551397 | ENSG00000206669.1 | | -1.7638167 | ENSG00000207975.1 | MIR181B1 | -1.3784147 |
| ENSG00000252383.1 | RNU6-314P | -2.850807 | ENSG00000228262.7 | LINC01320 | -1.7631472 | ENSG00000276097.1 | | -1.3777472 |
| ENSG00000276653.1 | RN7SL856P | -2.85005 | ENSG00000225214.1 | | -1.7615994 | ENSG00000279374.1 | | -1.3769977 |
| ENSG00000249970.1 | | -2.8497322 | ENSG00000239635.1 | | -1.7593617 | ENSG00000138308.5 | PLA2G12B | -1.3765649 |
| ENSG00000248995.2 | | -2.8490528 | ENSG00000275100.1 | | -1.7593494 | ENSG00000259280.1 | | -1.3761784 |
| ENSG00000229695.1 | | -2.8474851 | ENSG00000206557.5 | TRIM71 | -1.7589667 | ENSG00000249829.2 | | -1.3757232 |
| ENSG00000224551.1 | HMGB3P21 | -2.8390187 | ENSG00000262119.1 | | -1.757606 | ENSG00000245008.3 | | -1.3756975 |
| ENSG00000259208.2 | | -2.833586 | ENSG00000254697.1 | COPS8P3 | -1.7568412 | ENSG00000263860.1 | | -1.3753215 |
| ENSG00000201012.1 | | -2.8296403 | ENSG00000147596.3 | PRDM14 | -1.7563944 | ENSG00000259177.1 | | -1.375013 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000237982.1 | | -2.827153 | ENSG00000259905.4 | PWRN3 | -1.7561108 | ENSG00000251544.1 | MTND5P12 | -1.3748423 |
| ENSG00000257480.1 | MRPL2P1 | -2.8268375 | ENSG00000231504.1 | NMD3P2 | -1.7543302 | ENSG00000251598.1 | | -1.37472 |
| ENSG00000221326.1 | | -2.8235453 | ENSG00000212549.1 | RNA5SP354 | -1.7529495 | ENSG00000250308.2 | | -1.374371 |
| ENSG00000238508.1 | | -2.8231894 | ENSG00000263438.4 | | -1.7524678 | ENSG00000277740.1 | | -1.3743434 |
| ENSG00000280888.1 | | -2.8212412 | ENSG00000132446.6 | FTHL17 | -1.7524518 | ENSG00000224029.1 | | -1.3738478 |
| ENSG00000206652.1 | RNU1-1 | -2.8204214 | ENSG00000206658.1 | RNU6-1039P | -1.7512361 | ENSG00000254768.4 | SALL4P1 | -1.3727704 |
| ENSG00000225105.2 | LINC01076 | -2.8180684 | ENSG00000237675.4 | TEX36-AS1 | -1.7510037 | ENSG00000251575.2 | | -1.3726756 |
| ENSG00000273999.1 | RBM17P2 | -2.8144558 | ENSG00000270839.1 | | -1.7501613 | ENSG00000253596.1 | | -1.3726148 |
| ENSG00000280676.1 | | -2.8105784 | ENSG00000280511.1 | | -1.7488581 | ENSG00000249725.1 | | -1.3726007 |
| ENSG00000273316.1 | | -2.8056203 | ENSG00000277663.1 | | -1.7479704 | ENSG00000230572.4 | | -1.3720123 |
| ENSG00000277228.1 | | -2.8032149 | ENSG00000175497.15 | DPP10 | -1.7467534 | ENSG00000180772.6 | AGTR2 | -1.3700228 |
| ENSG00000254805.1 | SNRPCP14 | -2.7937501 | ENSG00000224194.1 | | -1.746266 | ENSG00000231699.1 | | -1.3697079 |
| ENSG00000223742.1 | | -2.7917636 | ENSG00000265641.1 | MIR3929 | -1.7458478 | ENSG00000231762.1 | | -1.3691512 |
| ENSG00000263813.1 | MIR3679 | -2.7889948 | ENSG00000231358.2 | | -1.7446369 | ENSG00000265717.1 | | -1.3681661 |
| ENSG00000232471.3 | | -2.7849968 | ENSG00000178287.16 | SPAG11A | -1.7443212 | ENSG00000266880.1 | | -1.3680585 |
| ENSG00000253093.1 | RNA5SP179 | -2.7825261 | ENSG00000257359.1 | | -1.7443101 | ENSG00000123560.12 | RNU6-1310P | -1.367726 |
| ENSG00000239263.1 | RBM43P1 | -2.7783467 | ENSG00000221641.1 | MIR1268A | -1.7437357 | ENSG00000104848.1 | PLP1 | -1.3674424 |
| ENSG00000291120.2 | CYCSP4 | -2.7739817 | ENSG00000260664.2 | | -1.7410339 | ENSG00000254381.3 | KCNA7 | -1.3666367 |
| ENSG00000265556.1 | | -2.7691264 | ENSG00000244044.3 | RN7SL735P | -1.7379652 | ENSG00000226249.1 | TUBB8P5 | -1.366476 |
| ENSG00000234418.1 | | -2.7655117 | ENSG00000253456.1 | | -1.7377965 | ENSG00000270442.1 | | -1.36647 |
| ENSG00000270764.1 | | -2.764615 | ENSG00000230649.2 | | -1.7377517 | ENSG00000249065.2 | PCNAP1 | -1.365848 |
| ENSG00000202515.1 | VTRNA1-3 | -2.7623057 | ENSG00000228222.1 | | -1.7375592 | ENSG00000248965.1 | | -1.3657729 |
| ENSG00000136352.16 | NKX2-1 | -2.7618524 | ENSG00000266202.1 | | -1.737493 | ENSG00000239373.3 | RN7SL425P | -1.3656151 |
| ENSG00000241774.3 | RN7SL438P | -2.7578728 | ENSG00000166408.4 | OR5P1P | -1.7371853 | ENSG00000250993.1 | | -1.365604 |
| ENSG00000258493.2 | | -2.750997 | ENSG00000131126.17 | TEX101 | -1.7371501 | ENSG00000281867.1 | | -1.3654134 |
| ENSG00000254044.4 | | -2.7433159 | ENSG00000224795.1 | C11orf39 | -1.7348568 | ENSG00000266513.1 | | -1.3639926 |
| ENSG00000276067.1 | | -2.7429577 | ENSG00000199865.1 | RNU6-49SP | -1.734784 | ENSG00000271338.1 | | -1.3639609 |
| ENSG00000232168.2 | P2RY10P2 | -2.7414234 | ENSG00000223676.1 | RPL34P26 | -1.7340785 | ENSG00000240097.1 | | -1.3637876 |
| ENSG00000226145.6 | KRT16P6 | -2.7364817 | ENSG00000272243.4 | | -1.7337089 | ENSG00000259691.2 | FKBP1AP2 | -1.3637746 |
| ENSG00000258232.2 | | -2.7338055 | ENSG00000250954.4 | | -1.7335482 | ENSG00000259914.1 | MACROD2-AS1 | -1.3635911 |
| ENSG00000241451.2 | RPS27P22 | -2.7254207 | ENSG00000109158.9 | GABRA4 | -1.7334079 | ENSG00000206684.1 | RNU6-157P | -1.3635105 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000198555.7 | | -2.7156947 | ENSG00000212122.3 | TSSK1B | -1.7331805 | ENSG00000233143.1 | DIRC3-AS1 | -1.3634848 |
| ENSG00000240626.3 | RN7SL150P | -2.7116889 | ENSG00000233713.2 | | -1.7330073 | ENSG00000249041.1 | | -1.3634773 |
| ENSG00000265673.1 | | -2.7061418 | ENSG00000124564.16 | SLC17A3 | -1.7329868 | ENSG00000275727.1 | | -1.3631135 |
| ENSG00000243355.1 | | -2.7051834 | ENSG00000255296.1 | | -1.7309515 | ENSG00000174930.4 | VN2R1P | -1.3630219 |
| ENSG00000275943.1 | | -2.7051688 | ENSG00000259690.1 | | -1.7308914 | ENSG00000182035.10 | ADIG | -1.3629981 |
| ENSG00000254487.2 | | -2.698658 | ENSG00000248635.1 | | -1.7301453 | ENSG00000278599.3 | TBC1D3E | -1.3622774 |
| ENSG00000267402.1 | TCF4-AS2 | -2.6976745 | ENSG00000294405.1 | | -1.7295132 | ENSG00000275355.1 | | -1.361929 |
| ENSG00000256882.1 | KNOP1P1 | -2.6960642 | ENSG00000201221.1 | RNU4-40P | -1.7292917 | ENSG00000251652.1 | | -1.3615566 |
| ENSG00000277900.1 | | -2.6898607 | ENSG00000251985.1 | RNU6-1161P | -1.7291732 | ENSG00000281318.1 | | -1.3608592 |
| ENSG00000267233.1 | HNRNPA3P16 | -2.6858126 | ENSG00000274845.1 | | -1.7289738 | ENSG00000174498.12 | IGDCC3 | -1.3601492 |
| ENSG00000238964.1 | RNU7-125P | -2.6846361 | ENSG00000258104.1 | HIGD1AP9 | -1.7289481 | ENSG00000225661.5 | RPL14P5 | -1.3600955 |
| ENSG00000229032.1 | | -2.683988 | ENSG00000277531.1 | | -1.7287631 | ENSG00000225775.1 | | -1.3599628 |
| ENSG00000254976.1 | OR8B7P | -2.6801286 | ENSG00000271697.1 | | -1.7284741 | ENSG00000233020.1 | | -1.3599372 |
| ENSG00000238224.1 | | -2.6798516 | ENSG00000264047.2 | RN7SL455P | -1.7269372 | ENSG00000263974.2 | RN7SL121P | -1.3578753 |
| ENSG00000260905.1 | | -2.6795171 | ENSG00000255079.1 | | -1.7265634 | ENSG00000196242.7 | OR2C3 | -1.3576656 |
| ENSG00000222409.1 | | -2.6789775 | ENSG00000253147.4 | | -1.7261828 | ENSG00000259602.1 | | -1.3575661 |
| ENSG00000281331.1 | | -2.6760339 | ENSG00000202047.1 | RNA5SP324 | -1.7254723 | ENSG00000264274.1 | MIR4799 | -1.3574839 |
| ENSG00000237478.2 | | -2.6723373 | ENSG00000259609.1 | | -1.7242268 | ENSG00000184423.5 | RPL23AP38 | -1.357305 |
| ENSG00000239958.3 | RN7SL51P | -2.6685045 | ENSG00000248980.1 | | -1.7238065 | ENSG00000257958.1 | | -1.3571807 |
| ENSG00000233103.1 | | -2.6645371 | ENSG00000105205.6 | CLC | -1.7236735 | ENSG00000106511.5 | MEOX2 | -1.3568713 |
| ENSG00000277586.1 | NEFL | -2.6612335 | ENSG00000224161.3 | RPS26P54 | -1.722416 | ENSG00000143171.11 | RXRG | -1.3562525 |
| ENSG00000232998.1 | VPS13A-AS1 | -2.6580434 | ENSG00000232464.1 | | -1.7220322 | ENSG00000235695.1 | | -1.3555987 |
| ENSG00000279542.1 | | -2.655025 | ENSG00000225376.4 | TMEM246-AS1 | -1.7218146 | ENSG00000254892.1 | | -1.3552129 |
| ENSG00000237016.1 | | -2.6525642 | ENSG00000224672.4 | | -1.7216443 | ENSG00000224007.1 | | -1.3549726 |
| ENSG00000278819.1 | MIR7107 | -2.6522396 | ENSG00000251011.4 | TMEM108-AS1 | -1.7216208 | ENSG00000233851.1 | LATS2-AS1 | -1.3548385 |
| ENSG00000232360.1 | | -2.6422894 | ENSG00000227351.2 | NANOGP6 | -1.7209272 | ENSG00000221387.1 | RNU6ATAC8P | -1.3541791 |
| ENSG00000231987.1 | | -2.6372724 | ENSG00000281372.1 | | -1.7193593 | ENSG00000226394.2 | | -1.3537787 |
| ENSG00000224203.2 | RPS23P10 | -2.637127 | ENSG00000243328.1 | | -1.7191349 | ENSG00000227330.1 | | -1.3515202 |
| ENSG00000254106.1 | | -2.6301528 | ENSG00000259104.2 | PTCSC3 | -1.7191124 | ENSG00000237329.2 | | -1.3514043 |
| ENSG00000214295.4 | FOXO1B | -2.6290969 | ENSG00000248550.3 | OTX2-AS1 | -1.7178208 | ENSG00000275569.1 | | -1.351298 |
| ENSG00000266190.1 | | -2.6273299 | ENSG00000203690.10 | TCP10 | -1.717525 | ENSG00000213081.3 | | -1.3511353 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000235533.1 | MKNK2P1 | -2.6271757 | ENSG00000236473.1 | KRT43P | -1.7164074 | ENSG00000221808.1 | MIR1256 | -1.3509448 |
| ENSG00000254173.1 | | -2.6230137 | ENSG00000252363.1 | RNU7-43P | -1.7163804 | ENSG00000226683.4 | | -1.3508476 |
| ENSG00000224484.1 | | -2.6205055 | ENSG00000207082.1 | RNU6-171P | -1.7162296 | ENSG00000218874.3 | CAPNS1P1 | -1.3506866 |
| ENSG00000254915.1 | | -2.6190202 | ENSG00000281708.1 | ERC2-IT1 | -1.7155105 | ENSG00000212138.1 | RNA5SP372 | -1.350512 |
| ENSG00000250306.1 | | -2.6185024 | ENSG00000229492.1 | | -1.7135826 | ENSG00000261336.1 | EIF4BP5 | -1.3503286 |
| ENSG00000264404.2 | | -2.6182045 | ENSG00000235555.6 | | -1.7104195 | ENSG00000233399.2 | | -1.3494254 |
| ENSG00000264685.1 | PRPF19P1 | -2.6176952 | ENSG00000257331.1 | | -1.7093925 | ENSG00000235274.1 | | -1.3483989 |
| ENSG00000258776.1 | | -2.6170901 | ENSG00000230988.3 | RPL23AP11 ADAMTS19-AS1 | -1.7086618 | ENSG00000267528.1 | | -1.3477675 |
| ENSG00000248878.1 | | -2.6168901 | ENSG00000249421.1 | | -1.7084045 | ENSG00000213355.3 | CNN2P8 | -1.3474549 |
| ENSG00000264171.1 | MIR4305 | -2.6159594 | ENSG00000251639.2 | | -1.708384 | ENSG00000261319.1 | | -1.3469305 |
| ENSG00000227929.3 | SRGAP3-AS3 | -2.6159033 | ENSG00000199051.2 | MIR361 | -1.7047942 | ENSG00000113100.8 | CDH9 MIR3199-1 | -1.3464934 |
| ENSG00000248803.1 | | -2.6093697 | ENSG00000224417.2 | | -1.7026985 | ENSG00000264073.1 | MIR3199-2 | -1.3456616 |
| ENSG00000259306.2 | | -2.6080638 | ENSG00000267768.1 | | -1.7025574 | ENSG00000279836.1 | | -1.3453848 |
| ENSG00000263501.1 | | -2.6073938 | ENSG00000280227.1 | | -1.70153 | ENSG00000274892.1 | | -1.3448239 |
| ENSG00000270294.1 | | -2.6058918 | ENSG00000279417.1 | | -1.7008564 | ENSG00000225497.4 | KCNMA1-AS2 | -1.3444339 |
| ENSG00000235570.1 | LINC00533 | -2.6052552 | ENSG00000206595.1 | RNU6-877P | -1.6997551 | ENSG00000259793.1 | | -1.3434414 |
| ENSG00000214124.3 | SNRPEP9 | -2.602581 | ENSG00000228015.1 | | -1.6992791 | ENSG00000252250.1 | | -1.3433234 |
| ENSG00000178358.4 | OR2D3 | -2.5993381 | ENSG00000280354.1 | | -1.6989044 | ENSG00000234683.1 | | -1.3423178 |
| ENSG00000200312.1 | RN7SKP255 | -2.5939397 | ENSG00000228191.1 | | -1.698759 | ENSG00000236667.1 | | -1.3417167 |
| ENSG00000276200.1 | RN7SL820P | -2.5920821 | ENSG00000253817.1 | | -1.6961714 | ENSG00000230251.1 | PHBP4 | -1.3414913 |
| ENSG00000132872.10 | SYT4 | -2.5915729 | ENSG00000229235.1 | | -1.695699 | ENSG00000242236.2 | RN7SL594P | -1.3414195 |
| ENSG00000111215.10 | PRR4 | -2.5880404 | ENSG00000228292.1 | | -1.6953072 | ENSG00000255928.1 | | -1.341341 |
| ENSG00000223810.2 | KRTAP28 | -2.5782333 | ENSG00000257101.1 | LRRC37A13P | -1.6947926 | ENSG00000226995.6 | LINC00658 | -1.3413264 |
| ENSG00000244065.1 | MARK2P17 | -2.5739363 | ENSG00000258763.4 | | -1.6941089 | ENSG00000240089.2 | BMS1P3 | -1.3408721 |
| ENSG00000264994.1 | SNORD92 | -2.5704351 | ENSG00000180116.14 | C12orf40 | -1.6930778 | ENSG00000170160.15 | CCDC144A | -1.3406662 |
| ENSG00000237963.1 | | -2.56908 | ENSG00000267389.1 | | -1.6918893 | ENSG00000237631.2 | | -1.3406181 |
| ENSG00000212535.1 | RNU6-808P | -2.5673296 | ENSG00000236834.1 | LINC00421 | -1.6915348 | ENSG00000234646.4 | | -1.3405123 |
| ENSG00000253156.1 | | -2.5673293 | ENSG00000227743.1 | | -1.6909777 | ENSG00000270850.1 | | -1.3401691 |
| ENSG00000233357.2 | RPL30P15 | -2.5659266 | ENSG00000243089.1 | | -1.6886215 | ENSG00000252305.1 | | -1.3401525 |
| ENSG00000231740.1 | | -2.5656481 | ENSG00000202146.1 | | -1.6873812 | ENSG00000201420.1 | RNA5SP512 | -1.3399001 |
| ENSG00000276890.1 | | -2.563398 | ENSG00000243770.3 | RN7SL65P | -1.6873127 | ENSG00000238650.2 | | -1.3394606 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000250500.1 | | -2.5612013 | ENSG00000232873.1 | RPL23AP93 | -1.6872763 | ENSG00000229988.1 | HBBP1 | -1.3392377 |
| ENSG00000234780.1 | | -2.5595811 | ENSG00000196944.3 | OR2T4 | -1.6869603 | ENSG00000201025.1 | | -1.3383066 |
| ENSG00000227722.1 | | -2.5567423 | ENSG00000227078.1 | | -1.685503 | ENSG00000224265.1 | | -1.3381745 |
| ENSG00000230240.1 | | -2.556683 | ENSG00000273513.1 | TBC1D3K | -1.6851292 | ENSG00000261310.1 | | -1.3370205 |
| ENSG00000233534.1 | | -2.5565357 | ENSG00000231189.1 | | -1.6846146 | ENSG00000239877.2 | IGSF11-AS1 | -1.3368881 |
| ENSG00000233792.3 | HDHD1P2 | -2.5532694 | ENSG00000259106.1 | | -1.683101 | ENSG00000229494.1 | | -1.3367785 |
| ENSG00000254698.1 | | -2.5507806 | ENSG00000268460.1 | | -1.6815774 | ENSG00000203729.7 | LINC00272 | -1.3360509 |
| ENSG00000125813.12 | PAX1 | -2.5469795 | ENSG00000165656.1 | RPL36P18 | -1.680859 | ENSG00000255021.1 | | -1.3360021 |
| ENSG00000228539.1 | | -2.5430062 | ENSG00000165197.4 | FIGF | -1.6796186 | ENSG00000263507.1 | | -1.3357907 |
| ENSG00000240108.1 | NCOR1P1 | -2.540125 | ENSG00000182333.13 | LIPF | -1.6751996 | ENSG00000252712.1 | SCARNA14 | -1.3355179 |
| ENSG00000134812.6 | GIF | -2.5392028 | ENSG00000265817.1 | FSBP | -1.6750778 | ENSG00000183747.10 | ACSM2A | -1.3343265 |
| ENSG00000219463.1 | RPSAP42 | -2.5385319 | ENSG00000232915.1 | | -1.6750067 | ENSG00000256226.1 | | -1.3334503 |
| ENSG00000242609.1 | | -2.5374083 | ENSG00000205494.8 | OR52A4P | -1.674991 | ENSG00000165973.16 | NELL1 | -1.3333705 |
| ENSG00000221476.1 | MIR1827 | -2.537181 | ENSG00000252779.1 | RNU6-182P | -1.674898 | ENSG00000271454.1 | | -1.3328083 |
| ENSG00000261191.1 | | -2.5321736 | ENSG00000234881.1 | PIGFP2 | -1.6736739 | ENSG00000249623.1 | | -1.3327517 |
| ENSG00000242703.1 | CCT4P1 | -2.5281905 | ENSG00000252957.1 | RNA5SP402 | -1.6722265 | ENSG00000260411.4 | | -1.3325125 |
| ENSG00000267550.1 | | -2.5264025 | ENSG00000166948.8 | TGM6 | -1.671532 | ENSG00000253015.1 | RN7SKP64 | -1.3316691 |
| ENSG00000223324.1 | RN7SKP273 | -2.5245856 | ENSG00000221602.1 | | -1.6699866 | ENSG00000244606.3 | RN7SL799P | -1.3315227 |
| ENSG00000177275.3 | OR2AJ1 | -2.5131177 | ENSG00000253429.1 | | -1.6692346 | ENSG00000182477.5 | OR2B8P | -1.3312832 |
| ENSG00000274954.1 | | -2.5123477 | ENSG00000232500.1 | | -1.6682046 | ENSG00000237303.2 | HIGD1AP8 | -1.3312595 |
| ENSG00000263399.1 | | -2.5084802 | ENSG00000260520.1 | | -1.6676357 | ENSG00000238553.1 | | -1.331049 |
| ENSG00000242668.3 | RN7SL317P | -2.5082818 | ENSG00000259281.1 | LINGO1-AS2 | -1.6674979 | ENSG00000272519.1 | | -1.3300686 |
| ENSG00000230864.1 | | -2.500498 | ENSG00000276611.1 | | -1.6641507 | ENSG00000264483.1 | MIR5008 | -1.32964 |
| ENSG00000270422.1 | | -2.5004923 | ENSG00000261555.1 | | -1.6639689 | ENSG00000275465.3 | | -1.3296327 |
| ENSG00000221325.1 | MIR1200 | -2.5004583 | ENSG00000251577.4 | | -1.6629155 | ENSG00000213527.5 | | -1.3295239 |
| ENSG00000235432.1 | | -2.4947759 | ENSG00000271621.1 | | -1.6624624 | ENSG00000235538.1 | | -1.3287297 |
| ENSG00000253579.1 | SUMO2P16 | -2.493792 | ENSG00000269546.1 | CLIC4P2 | -1.6618346 | ENSG00000202513.1 | RNU6-805P | -1.3285983 |
| ENSG00000226420.1 | IGLV3-4 | -2.4922197 | ENSG00000159409.13 | CELF3 | -1.6612487 | ENSG00000276993.1 | | -1.328237 |
| ENSG00000228504.1 | | -2.4889547 | ENSG00000222092.1 | RNU6-908P | -1.6605826 | ENSG00000241781.2 | | -1.3281862 |
| ENSG00000242021.2 | | -2.4886318 | ENSG00000227425.1 | MRPS21P2 | -1.6601526 | ENSG00000250962.1 | | -1.3281225 |
| ENSG00000263553.1 | | -2.4860775 | ENSG00000231817.6 | LINC01198 | -1.6592498 | ENSG00000253405.1 | EVX1-AS | -1.3270728 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000271156.1 | | -2.4849561 | ENSG00000206820.1 | RNU1-138P | -1.6590354 | ENSG00000223806.6 | LINC00114 | -1.3264591 |
| ENSG00000240963.1 | | -2.4837749 | ENSG00000250332.1 | | -1.6589195 | ENSG00000255015.1 | | -1.3263052 |
| ENSG00000276393.1 | | -2.4832387 | ENSG00000277136.1 | | -1.6587351 | ENSG00000252906.1 | SCARNA3 | -1.3254388 |
| ENSG00000250322.2 | | -2.4812188 | ENSG00000274430.1 | | -1.6581004 | ENSG00000216697.3 | NANOGP5 | -1.3250884 |
| ENSG00000267518.1 | | -2.4810914 | ENSG00000225542.1 | ZNF385D-AS1 | -1.657177 | ENSG00000280252.1 | | -1.3250514 |
| ENSG00000137252.8 | HCRTR2 | -2.4801424 | ENSG00000113209.8 | PCDHB5 | -1.6549509 | ENSG00000230287.3 | | -1.324839 |
| ENSG00000221464.1 | MIR1271 | -2.4770195 | ENSG00000230180.1 | | -1.6547068 | ENSG00000145808.7 | ADAMTS19 | -1.3248271 |
| ENSG00000252943.1 | RNU6-264P | -2.4700305 | ENSG00000277544.1 | | -1.6544306 | ENSG00000124159.14 | MATN4 | -1.3241975 |
| ENSG00000235196.3 | | -2.4655345 | ENSG00000267243.4 | | -1.6541219 | ENSG00000248673.1 | LINC01133 | -1.3239557 |
| ENSG00000185559.12 | DLK1 | -2.4626751 | ENSG00000276412.1 | | -1.6535778 | ENSG00000255886.1 | | -1.3239263 |
| ENSG00000242318.1 | | -2.4532026 | ENSG00000261205.2 | NIFKP4 | -1.6515626 | ENSG00000279732.1 | | -1.3237137 |
| ENSG00000252390.1 | RNU5F-4P | -2.4499831 | ENSG00000276359.1 | | -1.6508549 | ENSG00000241228.1 | | -1.3231741 |
| ENSG00000314460.2 | | -2.4478755 | ENSG00000263590.2 | | -1.6503064 | ENSG00000248125.1 | | -1.323168 |
| ENSG00000225514.1 | MTND1P34 | -2.4460693 | ENSG00000258671.2 | | -1.6496951 | ENSG00000201519.1 | RNU6-645P | -1.3217077 |
| ENSG00000270857.1 | | -2.4420948 | ENSG00000145832.11 | SLC25A48 | -1.6494459 | ENSG00000277655.1 | | -1.3215318 |
| ENSG00000253424.1 | | -2.4412758 | ENSG00000242251.3 | RN7SL20P | -1.6493155 | ENSG00000259869.1 | | -1.3210875 |
| ENSG00000270285.1 | | -2.441131 | ENSG00000215734.3 | MRPL20P1 | -1.6490549 | ENSG00000263082.1 | | -1.3208036 |
| ENSG00000271400.1 | | -2.4410415 | ENSG00000254724.1 | OR7E10P | -1.647881 | ENSG00000277045.1 | | -1.320767 |
| ENSG00000239215.1 | RPL27P12 | -2.4347093 | ENSG00000154611.13 | PSMA8 | -1.6464162 | ENSG00000242076.2 | IGKV1-33 | -1.320487 |
| ENSG00000270798.1 | | -2.4327248 | ENSG00000280166.1 | | -1.6449054 | ENSG00000255599.1 | | -1.3203639 |
| ENSG00000228680.1 | | -2.432335 | ENSG00000249745.1 | HMGB1P28 | -1.6438838 | ENSG00000223890.1 | | -1.3198711 |
| ENSG00000227427.1 | | -2.4314252 | ENSG00000225484.2 | FREM2-AS1 | -1.6438491 | ENSG00000187546.12 | AGMO | -1.3198218 |
| ENSG00000256748.1 | | -2.4298553 | ENSG00000256146.1 | | -1.6436402 | ENSG00000233955.1 | AHCYP3 | -1.3197374 |
| ENSG00000254790.1 | | -2.4290356 | ENSG00000265657.1 | MIR3151 | -1.6432225 | ENSG00000277968.1 | BUB3P1 | -1.3190102 |
| ENSG00000226216.1 | RPS12P5 | -2.4266581 | ENSG00000259303.5 | IGHV2OR16-5 | -1.6426191 | ENSG00000232835.1 | | -1.3186865 |
| ENSG00000179600.3 | GPHB5 | -2.4244097 | ENSG00000229921.5 | KIF25-AS1 | -1.6409892 | ENSG00000258856.2 | | -1.3184551 |
| ENSG00000268053.1 | | -2.4220887 | ENSG00000225350.1 | FREM2-AS1 | -1.6396848 | ENSG00000203809.5 | LINC00577 | -1.3181811 |
| ENSG00000216181.2 | | -2.4211587 | ENSG00000260158.1 | | -1.6382229 | ENSG00000281483.1 | | -1.3181457 |
| ENSG00000253542.6 | SDR16C6P | -2.4179231 | ENSG00000219249.2 | AMZ2P2 | -1.6380961 | ENSG00000261792.1 | DNM1P28 | -1.3172374 |
| ENSG00000238825.1 | RNU1-13P | -2.4172903 | ENSG00000261703.1 | | -1.6372077 | ENSG00000236062.1 | GSTM5P3 | -1.3172296 |
| ENSG00000259897.2 | | -2.4131803 | ENSG00000139767.7 | SRRM4 | -1.636739 | ENSG00000258893.1 | SETP2 | -1.316743 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000240419.1 | | -2.4118517 | ENSG00000225531.1 | | -1.6364105 | ENSG00000273407.1 | | -1.3158837 |
| ENSG00000273962.1 | IGKV2-40 | -2.4065921 | ENSG00000250343.1 | | -1.6348174 | ENSG00000269954.1 | | -1.3155628 |
| ENSG00000181072.10 | CHRM2 | -2.3949729 | ENSG00000258144.1 | | -1.6339107 | ENSG00000274096.1 | | -1.3149789 |
| ENSG00000264953.1 | | -2.3943987 | ENSG00000226072.1 | | -1.6326746 | ENSG00000270555.1 | | -1.3148824 |
| ENSG00000243883.3 | RN7SL419P | -2.3934075 | ENSG00000232337.1 | | -1.6319378 | ENSG00000267262.1 | | -1.3147226 |
| ENSG00000188909.4 | BSX | -2.3900602 | ENSG00000242595.1 | | -1.6319313 | ENSG00000207046.1 | RNU6-886P | -1.3143573 |
| ENSG00000270816.4 | LINC00221 | -2.3891961 | ENSG00000249752.1 | | -1.6312797 | ENSG00000227845.2 | | -1.3142154 |
| ENSG00000254563.1 | | -2.3855885 | ENSG00000252019.1 | RNU6ATAC9P | -1.6299326 | ENSG00000235183.3 | | -1.3142047 |
| ENSG00000263369.5 | | -2.3834808 | ENSG00000205293.3 | LINC01602 | -1.6297795 | ENSG00000259218.4 | LINC00928 | -1.3137848 |
| ENSG00000233304.4 | LINC01346 | -2.3770476 | ENSG00000229558.2 | SACS-AS1 | -1.6292147 | ENSG00000156103.14 | MMP16 | -1.3137234 |
| ENSG00000225344.1 | | -2.3769951 | ENSG00000224340.1 | | -1.6291896 | ENSG00000234293.1 | BACH1-IT3 | -1.3135609 |
| ENSG00000186190.7 | BPIFB3 | -2.3767333 | ENSG00000179577.3 | | -1.6279113 | ENSG00000268100.1 | ZNF725P | -1.3130532 |
| ENSG00000255547.1 | RPA2P3 | -2.3749851 | ENSG00000243620.1 | | -1.6273503 | ENSG00000234161.1 | PABPC5-AS1 | -1.3125485 |
| ENSG00000177596.1 | | -2.3743328 | ENSG00000221774.1 | | -1.626755 | ENSG00000274772.1 | | -1.312478 |
| ENSG00000202089.3 | RNU6-1306P | -2.3736815 | ENSG00000225056.1 | | -1.6262754 | ENSG00000224323.2 | DPRXP1 | -1.311739 |
| ENSG00000231200.1 | | -2.3700676 | ENSG00000164265.7 | SCGB3A2 | -1.6257708 | ENSG00000250348.1 | | -1.3117076 |
| ENSG00000217041.1 | | -2.3699901 | ENSG00000262038.1 | | -1.6256423 | ENSG00000267746.1 | | -1.3114759 |
| ENSG00000240874.1 | | -2.3627886 | ENSG00000232327.4 | | -1.6255252 | ENSG00000234108.1 | | -1.3114032 |
| ENSG00000251218.1 | | -2.362504 | ENSG00000231559.1 | | -1.6252907 | ENSG00000254001.4 | | -1.3106612 |
| ENSG00000222224.1 | | -2.3624554 | ENSG00000228422.3 | LINC00687 | -1.6233404 | ENSG00000237447.1 | CDC27P2 | -1.3106148 |
| ENSG00000232676.1 | ADH5P2 | -2.3623089 | ENSG00000253317.1 | | -1.6228517 | ENSG00000232982.1 | | -1.3105945 |
| ENSG00000211571.1 | | -2.3621241 | ENSG00000177103.12 | DSCAML1 | -1.6215957 | ENSG00000228965.1 | | -1.310026 |
| ENSG00000264421.1 | | -2.3593237 | ENSG00000212302.1 | | -1.6195172 | ENSG00000135298.12 | ADGRB3 | -1.3099322 |
| ENSG00000178235.7 | SLITRK1 | -2.3589373 | ENSG00000232667.8 | | -1.6187916 | ENSG00000120057.4 | SFRP5 | -1.3095268 |
| ENSG00000226134.1 | | -2.3573783 | ENSG00000225722.1 | | -1.6176009 | ENSG00000125046.13 | SSUH2 | -1.3094391 |
| ENSG00000213201.3 | FABP5P10 | -2.3480703 | ENSG00000255231.1 | MRPS36P4 | -1.6174589 | ENSG00000241211.1 | IQCJ-SCHIP1-AS1 | -1.309347 |
| ENSG00000262366.1 | NDUFA3P6 | -2.3463318 | ENSG00000254489.1 | | -1.6167878 | ENSG00000259235.1 | | -1.308912 |
| ENSG00000271010.1 | | -2.3446853 | ENSG00000255666.4 | | -1.6163661 | ENSG00000234415.1 | RPL5P7 | -1.3087371 |
| ENSG00000230250.1 | | -2.3446147 | ENSG00000209702.1 | SNORD41 | -1.6154274 | ENSG00000252671.1 | | -1.3087133 |
| ENSG00000251804.1 | RNU6-1294P | -2.3433414 | ENSG00000258448.1 | | -1.6151798 | ENSG00000264888.1 | | -1.3082077 |
| ENSG00000251170.1 | | -2.3433198 | ENSG00000249441.1 | | -1.6132862 | ENSG00000261399.1 | | -1.3071079 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000271860.4 | | -2.3407305 | ENSG00000243227.3 | RN7SL5SP | -1.6128816 | ENSG00000276933.1 | MIR7641-1 | -1.3070903 |
| ENSG00000234967.1 | | -2.340357 | ENSG00000264908.1 | | -1.6117659 | ENSG00000236674.2 | | -1.3070062 |
| ENSG00000253859.1 | IGLV1-38 | -2.3371128 | ENSG00000228901.3 | HMGN2P36 | -1.6116407 | ENSG00000213664.4 | RPS16P8 | -1.3069433 |
| ENSG00000263905.2 | RN7SL55SP | -2.3368784 | ENSG00000143552.8 | NUP210L | -1.6116085 | ENSG00000228549.3 | | -1.3068327 |
| ENSG00000223625.1 | CYCSP32 | -2.3362681 | ENSG00000159217.8 | IGF2BP1 | -1.6108118 | ENSG00000232768.1 | | -1.3061523 |
| ENSG00000201198.1 | RNU6-879P | -2.3344294 | ENSG00000249550.5 | LINC01234 | -1.6103087 | ENSG00000178130.9 | FAM27L | -1.3058624 |
| ENSG00000251206.1 | | -2.3326743 | ENSG00000275954.3 | TBC1D3F | -1.6094549 | ENSG00000279273.1 | | -1.3056717 |
| ENSG00000274611.3 | TBC1D3 | -2.3312765 | ENSG00000234206.4 | | -1.6092394 | ENSG00000281181.1 | | -1.3052896 |
| ENSG00000207954.1 | MIR138-1 | -2.3277028 | ENSG00000203573.4 | | -1.6083723 | ENSG00000207808.1 | MIR27A | -1.3052596 |
| ENSG00000253202.1 | IGKV3-25 | -2.3276761 | ENSG00000226207.1 | | -1.6083379 | ENSG00000183454.12 | GRIN2A | -1.3051321 |
| ENSG00000200895.1 | RN7SKP245 | -2.3274908 | ENSG00000225451.1 | | -1.6068132 | ENSG00000234564.1 | HSPA8P20 | -1.3051284 |
| ENSG00000253105.1 | RNU6-176P | -2.3252148 | ENSG00000187763.3 | OR2B7P | -1.6052563 | ENSG00000213487.3 | ASS1P4 | -1.3048505 |
| ENSG00000255232.1 | | -2.320315 | ENSG00000227892.1 | OR5P4P | -1.6050134 | ENSG00000232041.1 | PSMD10P3 | -1.3044133 |
| ENSG00000264916.2 | RN7SL230P | -2.3196846 | ENSG00000224643.4 | | -1.6050074 | ENSG00000234466.1 | | -1.3040351 |
| ENSG00000261185.2 | RN7SL804P | -2.3190715 | ENSG00000224933.2 | LINC01034 | -1.604624 | ENSG00000221048.1 | | -1.3036886 |
| ENSG00000276486.1 | | -2.3181827 | ENSG00000253425.2 | HSPA8P13 | -1.6036929 | ENSG00000248148.1 | | -1.3035285 |
| ENSG00000253239.1 | IGLV1-70 | -2.3179504 | ENSG00000236099.1 | | -1.603125 | ENSG00000206014.6 | OR7E161P | -1.3032023 |
| ENSG00000227497.1 | PABPC1P6 | -2.3162718 | ENSG00000150276.8 | PPIAP26 | -1.6031715 | ENSG00000184502.3 | GAST | -1.302495 |
| ENSG00000164325.7 | TMEM174 | -2.3162654 | ENSG00000230922.1 | | -1.6023214 | ENSG00000185037.9 | ZNF733P | -1.3014274 |
| ENSG00000260617.1 | | -2.3155024 | ENSG00000264763.1 | MIR4295 | -1.6017863 | ENSG00000259482.1 | RORA-AS2 | -1.3011009 |
| ENSG00000258977.1 | LINC01467 | -2.3138549 | ENSG00000212724.3 | KRTAP2-3 | -1.6000972 | ENSG00000257662.1 | EIF4A1P12 | -1.3010723 |
| ENSG00000266625.1 | | -2.3130528 | ENSG00000231158.1 | PTP4A1P1 | -1.5999101 | ENSG00000277590.1 | MIR7845 | -1.3008827 |
| ENSG00000226217.1 | RPL19P1 | -2.3116816 | ENSG00000178222.11 | RNF212 | -1.5984955 | ENSG00000270773.1 | | -1.3006561 |
| ENSG00000234696.1 | GPR50-AS1 | -2.3113632 | ENSG00000248790.1 | | -1.5981732 | ENSG00000275688.3 | CCL15-CCL14 | -1.3004506 |
| ENSG00000255588.2 | | -2.3095659 | ENSG00000250345.2 | | -1.597339 | ENSG00000248478.2 | | -1.3004365 |
| ENSG00000201227.1 | RNA5-8SP3 | -2.3077359 | ENSG00000244471.1 | | -1.5972623 | ENSG00000229184.2 | ATP5HP2 | -1.3003492 |
| ENSG00000223111.1 | | -2.3061038 | ENSG00000181291.5 | TMEM132E | -1.596762 | ENSG00000257848.1 | | -1.2988263 |
| ENSG00000205883.2 | DEFB135 | -2.3057485 | ENSG00000233056.2 | ERVH48-1 | -1.5966134 | ENSG00000207449.1 | RNU6-19P | -1.2987089 |
| ENSG00000264352.2 | RN7SL602P | -2.2992683 | ENSG00000279687.1 | | -1.5964557 | ENSG00000272027.2 | | -1.2976077 |
| ENSG00000206738.1 | | -2.2963848 | ENSG00000272887.1 | CSPG4P5 | -1.5918342 | ENSG00000251706.1 | RNU7-61P | -1.2967172 |
| ENSG00000200351.1 | | -2.2957067 | ENSG00000270002.1 | | -1.5913311 | ENSG00000223538.2 | | -1.2962757 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000279973.1 | | -2.2955741 | ENSG00000235818.3 | VN1R17P | -1.5883569 | ENSG00000225371.1 | CICP8 | -1.2946912 |
| ENSG00000230794.1 | | -2.2950389 | ENSG00000240905.3 | RN7SL798P | -1.5875391 | ENSG00000274342.1 | | -1.293696 |
| ENSG00000200389.1 | RNU6-509P | -2.2941229 | ENSG00000253553.4 | | -1.5869909 | ENSG00000182747.4 | SLC35D3 | -1.2934572 |
| ENSG00000273119.1 | | -2.2925937 | ENSG00000222086.1 | | -1.5862481 | ENSG00000270926.1 | | -1.2934353 |
| ENSG00000279516.1 | FAM230C | -2.2922367 | ENSG00000253631.1 | IGLV7-35 | -1.5859616 | ENSG00000265056.1 | MIR548S | -1.29319 |
| ENSG00000277013.3 | OR7E96P | -2.2918375 | ENSG00000271045.1 | | -1.5835355 | ENSG00000107187.14 | LHX3 | -1.2922937 |
| ENSG00000255786.1 | | -2.2902761 | ENSG00000265049.1 | | -1.5850224 | ENSG00000225533.1 | PAWRP1 | -1.2919386 |
| ENSG00000258637.1 | | -2.2892979 | ENSG00000230497.2 | EEF1B2P8 | -1.5848105 | ENSG00000254113.1 | | -1.2915208 |
| ENSG00000181984.11 | GOLGA8CP | -2.2891126 | ENSG00000266097.1 | MIR5192 | -1.5847958 | ENSG00000279735.1 | | -1.2902725 |
| ENSG00000254897.1 | | -2.2869217 | ENSG00000254241.1 | | -1.5838717 | ENSG00000250674.1 | | -1.2902623 |
| ENSG00000202119.1 | RNU6-302P | -2.2860603 | ENSG00000231208.4 | ZBTB46-AS1 | -1.5837567 | ENSG00000233377.1 | MTND4P20 | -1.2901415 |
| ENSG00000235120.1 | BSN-AS1 | -2.2827763 | ENSG00000230686.1 | | -1.5801006 | ENSG00000235532.4 | LINC00460 | -1.2901265 |
| ENSG00000241223.3 | RN7SL39P | -2.2818753 | ENSG00000124915.9 | | -1.5798142 | ENSG00000251478.1 | | -1.2897663 |
| ENSG00000253181.1 | | -2.281868 | ENSG00000206090.4 | | -1.5792594 | ENSG00000216642.1 | | -1.2894753 |
| ENSG00000261818.1 | | -2.2808904 | ENSG00000238423.1 | SNORD42B | -1.5790932 | ENSG00000273986.1 | | -1.2890795 |
| ENSG00000221261.1 | MIR1208 | -2.2792453 | ENSG00000177938.4 | CAPZA3 | -1.5759978 | ENSG00000277054.1 | FDX1P2 | -1.2889805 |
| ENSG00000237104.1 | | -2.2764327 | ENSG00000236053.1 | LINC01067 | -1.5751016 | ENSG00000279756.1 | | -1.2886665 |
| ENSG00000221468.1 | RNU6ATAC11P | -2.2763498 | ENSG00000227454.2 | MTND4P30 | -1.5750209 | ENSG00000278941.1 | SMG6-IT1 | -1.288804 |
| ENSG00000259601.2 | | -2.2757012 | ENSG00000253932.1 | | -1.5749685 | ENSG00000265002.1 | | -1.2878274 |
| ENSG00000257253.2 | | -2.2729829 | ENSG00000249451.1 | | -1.574948 | ENSG00000194297.2 | RNU1-75P | -1.2859683 |
| ENSG00000261288.1 | | -2.2716888 | ENSG00000171819.4 | ANGPTL7 | -1.5740515 | ENSG00000275026.1 | GXYLT1P4 | -1.2859411 |
| ENSG00000258499.1 | | -2.2692629 | ENSG00000256640.1 | | -1.5734932 | ENSG00000254019.1 | | -1.2850147 |
| ENSG00000258739.1 | ENO1P2 | -2.2687983 | ENSG00000271143.1 | | -1.5734438 | ENSG00000240666.2 | MME-AS1 | -1.2849777 |
| ENSG00000253205.4 | | -2.2676773 | ENSG00000224214.1 | RNU2-59P | -1.5734231 | ENSG00000207460.1 | SNORD116-19 | -1.2848955 |
| ENSG00000255372.1 | | -2.2642698 | ENSG00000207440.1 | RNU6-541P | -1.5724008 | ENSG00000232109.1 | | -1.2848099 |
| ENSG00000237479.1 | | -2.2617959 | ENSG00000268055.1 | | -1.572244 | ENSG00000182600.8 | C2orf82 | -1.2845997 |
| ENSG00000154975.12 | CA10 | -2.2608365 | ENSG00000280220.1 | | -1.5716731 | ENSG00000279790.1 | | -1.2841023 |
| ENSG00000277705.1 | | -2.2590871 | ENSG00000224435.2 | NF1P6 | -1.5713912 | ENSG00000248903.1 | | -1.2834167 |
| ENSG00000236449.1 | | -2.2564864 | ENSG00000244155.1 | CYP4F34P | -1.5711469 | ENSG00000188933.13 | USP32P1 | -1.2830733 |
| ENSG00000232305.1 | CLCP1 | -2.2531392 | ENSG00000212391.1 | | -1.5700024 | ENSG00000261701.5 | HPR | -1.2830301 |
| ENSG00000206852.1 | RNU6-895P | -2.2509204 | ENSG00000272121.1 | | -1.5696212 | ENSG00000267057.4 | | -1.2826819 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000207071.1 | RNU6-1207P | -2.2479572 | ENSG00000165556.9 | CDX2 | -1.5692863 | ENSG00000258980.1 | EIF1AXP2 | -1.2821529 |
| ENSG00000238220.1 | | -2.2471858 | ENSG00000256237.1 | | -1.5692334 | ENSG00000225843.1 | NIPA2P1 | -1.2817214 |
| ENSG00000279983.1 | | -2.2468973 | ENSG00000206013.2 | IFITM5 | -1.5685385 | ENSG00000206145.7 | P2RX6P | -1.2815009 |
| ENSG00000275115.1 | | -2.2465653 | ENSG00000221555.1 | | -1.5666193 | ENSG00000237469.2 | TUBB8P10 | -1.2814462 |
| ENSG00000259173.2 | | -2.2458867 | ENSG00000280250.1 | | -1.5663902 | ENSG00000211514.1 | MIR454 | -1.2810952 |
| ENSG00000264160.1 | MIR4762 | -2.2426708 | ENSG00000204003.7 | | -1.5656917 | ENSG00000163497.2 | FEV | -1.2808591 |
| ENSG00000253199.1 | | -2.2424234 | ENSG00000279888.1 | !? | -1.5652696 | ENSG00000279581.1 | | -1.2804167 |
| ENSG00000239910.3 | RN7SL530P | -2.2415784 | ENSG00000241098.1 | | -1.5650879 | ENSG00000230039.1 | MTND5P30 | -1.2802358 |
| ENSG00000248955.1 | | -2.2368815 | ENSG00000269419.1 | | -1.5646825 | ENSG00000201078.1 | RN7SKP214 | -1.2799031 |
| ENSG00000253339.1 | | -2.2384672 | ENSG00000216998.1 | CYP2AC1P | -1.563612 | ENSG00000124557.11 | BTN1A1 | -1.2794409 |
| ENSG00000236687.1 | | -2.2370756 | ENSG00000271272.1 | | -1.5632988 | ENSG00000215096.3 | IFITM8P | -1.2789284 |
| ENSG00000225574.1 | DRAXINP1 | -2.2365572 | ENSG00000253925.1 | | -1.5624816 | ENSG00000200560.1 | RNU6-288P | -1.2789208 |
| ENSG00000231906.1 | | -2.232114 | ENSG00000252658.1 | RNU6-786P | -1.5623875 | ENSG00000270071.1 | | -1.2786067 |
| ENSG00000272439.1 | RNU6-91P | -2.2306009 | ENSG00000228976.1 | SUMO2P8 | -1.5620982 | ENSG00000237268.2 | | -1.2782786 |
| ENSG00000277011.1 | | -2.2301858 | ENSG00000264673.1 | | -1.5609116 | ENSG00000189212.11 | DPY19L2P1 | -1.2778558 |
| ENSG00000266348.1 | PSMC1P10 | -2.2296076 | ENSG00000229327.1 | | -1.5603937 | ENSG00000279872.1 | | -1.2778532 |
| ENSG00000252951.1 | RNA5SP165 | -2.2240152 | ENSG00000254384.1 | MTND6P19 | -1.559886 | ENSG00000264464.1 | | -1.2774098 |
| ENSG00000199638.1 | RNA5SP319 | -2.223142 | ENSG00000260049.1 | | -1.5596911 | ENSG00000150051.12 | MKX | -1.2761179 |
| ENSG00000204669.8 | C9orf57 | -2.221841 | ENSG00000206682.1 | | -1.558298 | ENSG00000277223.1 | | -1.276117 |
| ENSG00000201668.1 | | -2.2193119 | ENSG00000232211.1 | | -1.5580869 | ENSG00000196408.10 | NOXO1 | -1.2756445 |
| ENSG00000252050.1 | | -2.2191062 | ENSG00000233115.4 | FAM90A11P | -1.5579379 | ENSG00000275607.1 | | -1.2756443 |
| ENSG00000231082.1 | | -2.2189089 | ENSG00000271239.1 | | -1.5568556 | ENSG00000279839.1 | | -1.2754427 |
| ENSG00000265964.1 | | -2.2175267 | ENSG00000221563.1 | MIR1269A | -1.5566434 | ENSG00000258068.1 | | -1.2750049 |
| ENSG00000250603.1 | | -2.2152314 | ENSG00000105131.6 | EPHX3 | -1.5562679 | ENSG00000257110.2 | | -1.2749094 |
| ENSG00000255325.2 | | -2.2140746 | ENSG00000139874.5 | SSTR1 | -1.5623382 | ENSG00000213218.8 | CSH2 | -1.2736298 |
| ENSG00000176774.5 | MAGEB18 | -2.2122316 | ENSG00000277387.1 | MIR8058 | -1.5551133 | ENSG00000218363.1 | SLC25A20P1 | -1.2734737 |
| ENSG00000225632.1 | | -2.2122302 | ENSG00000266875.2 | RN7SLA08P | -1.5548582 | ENSG00000239739.1 | | -1.2724846 |
| ENSG00000241084.1 | | -2.2107794 | ENSG00000230166.1 | | -1.554488 | ENSG00000243296.1 | | -1.2723801 |
| ENSG00000234056.1 | LINC00463 | -2.2063953 | ENSG00000231846.1 | | -1.5541925 | ENSG00000199306.1 | RNU6-858P | -1.2720177 |
| ENSG00000229770.1 | | -2.2030451 | ENSG00000223432.1 | | -1.5541454 | ENSG00000242140.1 | | -1.2713597 |
| ENSG00000210181.1 | RNU6ATAC4P | -2.2030114 | ENSG00000276606.2 | | -1.5535314 | ENSG00000213752.3 | | -1.2708448 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000207467.1 | | -2.2027977 | ENSG00000253008.2 | MIR2355 | -1.5529922 | ENSG00000242152.1 | | -1.2706083 |
| ENSG00000235549.1 | EIF1P2 | -2.2010289 | ENSG00000211854.1 | TRAJ35 | -1.5528322 | ENSG00000199630.1 | | -1.2705657 |
| ENSG00000270491.1 | | -2.200375 | ENSG00000268673.3 | | -1.551776 | ENSG00000201048.1 | | -1.2701458 |
| ENSG00000265881.1 | PDLIM1P2 | -2.2000952 | ENSG00000248228.1 | SLIT2-IT1 | -1.5507137 | ENSG00000280176.1 | | -1.2699972 |
| ENSG00000204571.5 | KRTAP5-11 | -2.1972028 | ENSG00000248684.1 | BIN2P2 | -1.5506234 | ENSG00000230520.1 | | -1.2694912 |
| ENSG00000230035.2 | | -2.1937026 | ENSG00000216070.1 | | -1.5501709 | ENSG00000139219.16 | COL2A1 | -1.2690954 |
| ENSG00000260970.1 | | -2.1926944 | ENSG00000221424.1 | | -1.5499045 | ENSG00000236115.1 | | -1.268956 |
| ENSG00000234784.2 | | -2.1924532 | ENSG00000240237.1 | | -1.5496607 | ENSG00000211574.1 | MIR770 | -1.2687798 |
| ENSG00000236639.4 | LINC01158 | -2.1910046 | ENSG00000218872.1 | | -1.5492703 | ENSG00000244399.3 | RN7SL251P | -1.2686273 |
| ENSG00000179420.11 | OR6W1P | -2.1901734 | ENSG00000234597.1 | | -1.549223 | ENSG00000263201.1 | | -1.2683452 |
| ENSG00000224162.1 | UQCRHP3 | -2.189321 | ENSG00000267328.1 | | -1.5482447 | ENSG00000224849.2 | | -1.2681855 |
| ENSG00000280600.1 | | -2.1827116 | ENSG00000253621.1 | | -1.548174 | ENSG00000226626.2 | NOP56P2 | -1.2679545 |
| ENSG00000253467.1 | IGHV7-40 | -2.1815483 | ENSG00000201104.1 | RNU6-11P | -1.5479191 | ENSG00000250266.1 | | -1.2678668 |
| ENSG00000251128.1 | WWC2-AS1 | -2.1798481 | ENSG00000187806.6 | TMEM202 | -1.5473281 | ENSG00000270864.1 | IGHV3OR16-6 | -1.2674467 |
| ENSG00000844453.15 | SLCO1A2 | -2.1796421 | ENSG00000278077.1 | | -1.5472124 | ENSG00000228771.1 | | -1.2674192 |
| ENSG00000256315.1 | | -2.1782367 | ENSG00000252659.1 | RNU6-1088P | -1.5469164 | ENSG00000251655.5 | PRB1 | -1.2672976 |
| ENSG00000229206.3 | | -2.1778436 | ENSG00000278435.1 | | -1.546529 | ENSG00000234386.4 | OR7E162P | -1.266033 |
| ENSG00000223838.1 | | -2.175765 | ENSG00000207302.1 | | -1.5458627 | ENSG00000234592.1 | | -1.2659977 |
| ENSG00000200652.1 | | -2.1739912 | ENSG00000263159.1 | | -1.5457403 | ENSG00000246448.2 | | -1.2656183 |
| ENSG00000260962.1 | LINC00557 | -2.1739361 | ENSG00000199444.1 | | -1.5451903 | ENSG00000233358.1 | | -1.2654404 |
| ENSG00000273846.1 | | -2.1693062 | ENSG00000244234.1 | GMCL1P1 | -1.5450253 | ENSG00000227960.1 | | -1.2636299 |
| ENSG00000255451.1 | | -2.1636628 | ENSG00000261010.1 | RARRES2P6 | -1.5449519 | ENSG00000224895.1 | VPS26BP1 | -1.2635388 |
| ENSG00000630015.18 | SEZ6 | -2.1633453 | ENSG00000243886.1 | | -1.5435641 | ENSG00000259384.5 | GH1 | -1.2634808 |
| ENSG00000257517.1 | | -2.1631049 | ENSG00000279925.1 | | -1.541769 | ENSG00000232599.1 | | -1.2628873 |
| ENSG00000265461.1 | | -2.1593732 | ENSG00000264041.2 | RN7SL670P | -1.5411804 | ENSG00000236077.2 | | -1.262508 |
| ENSG00000258517.1 | | -2.1536568 | ENSG00000206779.1 | | -1.5410413 | ENSG00000169297.7 | NR0B1 | -1.2624138 |
| ENSG00000198650.9 | TAT | -2.1482234 | ENSG00000270745.1 | | -1.5409719 | ENSG00000259350.2 | | -1.2615318 |
| ENSG00000212181.1 | | -2.1459947 | ENSG00000278433.1 | MIR6070 | -1.5408983 | ENSG00000231302.1 | RPL36P2 | -1.2608127 |
| ENSG00000267726.1 | TMEM256P2 | -2.1456632 | ENSG00000164532.10 | TBX20 | -1.5406767 | ENSG00000268985.1 | | -1.2604961 |
| ENSG00000253088.1 | | -2.1455359 | ENSG00000214998.2 | CCNB2P1 | -1.5395394 | ENSG00000136487.16 | GH2 | -1.26038 |
| ENSG00000240870.2 | RPL19P14 | -2.1442273 | ENSG00000146453.11 | PNLDC1 | -1.5393854 | ENSG00000230350.1 | RPL35AP3 | -1.2595398 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000212410.1 | RNU6-932P | -2.1419691 | ENSG00000229316.1 | HMGB1P45 | -1.5393616 | ENSG00000269524.1 | | -1.2591372 |
| ENSG00000258262.1 | | -2.1403597 | ENSG00000236611.1 | | -1.5385304 | ENSG00000232549.1 | SRD5A1P1 | -1.2589073 |
| ENSG00000250020.1 | | -2.1398196 | ENSG00000169906.5 | S100G | -1.5375948 | ENSG00000268981.4 | | -1.2567965 |
| ENSG00000274190.1 | | -2.1384068 | ENSG00000246095.2 | LINC01096 | -1.5374496 | ENSG00000264490.3 | | -1.2562532 |
| ENSG00000207448.1 | RNU6-520P | -2.1379972 | ENSG00000213187.3 | COPS5P1 | -1.537443 | ENSG00000235024.1 | | -1.2558466 |
| ENSG00000244020.2 | MT1HL1 | -2.1379831 | ENSG00000125571.8 | IL37 | -1.5369048 | ENSG00000066382.15 | MPPED2 | -1.2557887 |
| ENSG00000236940.1 | | -2.1374383 | ENSG00000242473.1 | KIR2DP1 | -1.5363894 | ENSG00000206975.1 | RNU6-13P | -1.2557025 |
| ENSG00000260024.1 | MRPS21P7 | -2.1367245 | ENSG00000211923.1 | IGHD3-10 | -1.5362757 | ENSG00000258331.1 | | -1.2549844 |
| ENSG00000254946.1 | | -2.1366353 | ENSG00000178403.3 | NEUROG2 | -1.5357761 | ENSG00000265510.1 | MIR4436A | -1.2542713 |
| ENSG00000253260.1 | | -2.1355217 | ENSG00000280180.1 | | -1.5356121 | ENSG00000242024.1 | UGT1A5 | -1.2541816 |
| ENSG00000235661.2 | MIR670HG | -2.1351168 | ENSG00000253056.1 | RNU7-128P | -1.5355573 | ENSG00000280904.1 | | -1.254105 |
| ENSG00000236117.1 | | -2.1335285 | ENSG00000222509.1 | CACNA1C-AS2 | -1.5344479 | ENSG00000171505.5 | OR3N1 | -1.2538026 |
| ENSG00000180150.5 | HMGN2P9 | -2.1327847 | ENSG00000256271.1 | | -1.5343935 | ENSG00000205922.4 | ONECUT3 | -1.2534324 |
| ENSG00000231198.1 | | -2.1313625 | ENSG00000254306.1 | | -1.5340318 | ENSG00000170835.13 | CEL | -1.2533218 |
| ENSG00000273725.1 | | -2.1283835 | ENSG00000246820.2 | | -1.5339914 | ENSG00000268789.1 | VN1R87P | -1.2532031 |
| ENSG00000263765.4 | | -2.1274541 | ENSG00000222044.1 | | -1.5339688 | ENSG00000272541.1 | | -1.2520997 |
| ENSG00000239888.3 | RN7SL792P | -2.1264374 | ENSG00000253793.1 | | -1.5337699 | ENSG00000204065.2 | TCEAL5 | -1.2520595 |
| ENSG00000258055.1 | | -2.1252102 | ENSG00000181514.6 | | -1.5334249 | ENSG00000233663.2 | | -1.2518663 |
| ENSG00000200003.1 | RNU6-986P | -2.122729 | ENSG00000261666.1 | LINC00560 | -1.5323846 | ENSG00000176115.9 | AQP7P4 | -1.2518404 |
| ENSG00000239197.1 | | -2.1208485 | ENSG00000250561.2 | OR7E59P | -1.5314321 | ENSG00000171403.8 | KRT9 | -1.2510948 |
| ENSG00000259356.1 | | -2.1207243 | ENSG00000252135.1 | RNVU1-2 | -1.5311818 | ENSG00000281108.1 | | -1.2504981 |
| ENSG00000253117.4 | OC90 | -2.119698 | ENSG00000222511.2 | | -1.530289 | ENSG00000256101.4 | | -1.250153 |
| ENSG00000274977.1 | | -2.1193919 | ENSG00000253810.1 | PSAT1P1 | -1.5296792 | ENSG00000252409.1 | | -1.249588 |
| ENSG00000270989.1 | | -2.1192886 | ENSG00000263946.1 | | -1.5289481 | ENSG00000265257.4 | | -1.2495853 |
| ENSG00000168884.2 | OR4D6 | -2.1163074 | ENSG00000279706.1 | | -1.5285636 | ENSG00000262470.2 | TVP23CP2 | -1.2490636 |
| ENSG00000234864.1 | | -2.1158314 | ENSG00000264899.1 | | -1.5285008 | ENSG00000179046.7 | TRIML2 | -1.2483045 |
| ENSG00000213630.3 | BOLA3P3 | -2.1157418 | ENSG00000231383.2 | FGF12-AS1 | -1.5284734 | ENSG00000281664.1 | LINC00538 | -1.2472556 |
| ENSG00000267686.1 | | -2.1149108 | ENSG00000257904.1 | | -1.5280333 | ENSG00000172362.2 | OR5B12 | -1.2471414 |
| ENSG00000183463.5 | URAD | -2.1140917 | ENSG00000204949.7 | FAM83A-AS1 | -1.5280231 | ENSG00000280435.1 | | -1.2469881 |
| ENSG00000275519.1 | MIR6804 | -2.1135205 | ENSG00000234661.1 | | -1.5277995 | ENSG00000257599.1 | OVCH1-AS1 | -1.246602 |
| ENSG00000199762.1 | | -2.1122168 | ENSG00000171450.5 | CDK5R2 | -1.5272236 | ENSG00000229019.1 | | -1.2457347 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000234713.3 | | -2.1115264 | ENSG00000255107.1 | | -1.5270583 | ENSG00000234809.2 | BEND3P2 | -1.2456672 |
| ENSG00000238966.1 | | -2.1108049 | ENSG00000216136.2 | | -1.5269401 | ENSG00000207627.1 | MIR581 | -1.2456433 |
| ENSG00000250708.1 | | -2.1096787 | ENSG00000224679.1 | MED15P4 | -1.5261676 | ENSG00000229009.6 | TMPRSS11GP | -1.2454964 |
| ENSG00000265654.1 | | -2.1088854 | ENSG00000255027.2 | | -1.5254756 | ENSG00000270934.1 | | -1.2449998 |
| ENSG00000276745.1 | | -2.1083229 | ENSG00000270321.1 | | -1.5254346 | ENSG00000179826.6 | MRGPRX3 | -1.2448964 |
| ENSG00000258375.2 | | -2.10741 | ENSG00000112038.16 | OPRM1 | -1.5235731 | ENSG00000280162.1 | | -1.2442973 |
| ENSG00000252744.1 | | -2.1059583 | ENSG00000207701.1 | MIR597 | -1.5228958 | ENSG00000250803.4 | | -1.2439056 |
| ENSG00000229086.3 | LINC01548 | -2.1058978 | ENSG00000233216.1 | | -1.522812 | ENSG00000259964.5 | THSD4-AS1 | -1.2436996 |
| ENSG00000248625.1 | | -2.1047921 | ENSG00000251117.5 | LINC00588 | -1.5224294 | ENSG00000223944.1 | | -1.2436264 |
| ENSG00000250496.2 | ABT1P1 | -2.1046327 | ENSG00000252474.1 | RNU6-539P | -1.5223228 | ENSG00000253811.1 | | -1.2435019 |
| ENSG00000251807.1 | RNU6-202P | -2.1033502 | ENSG00000258566.2 | | -1.5219766 | ENSG00000267069.1 | | -1.2433102 |
| ENSG00000212303.1 | RNU6-1154P | -2.1021992 | ENSG00000184276.2 | DEFB108B | -1.5219262 | ENSG00000216687.2 | | -1.24304 |
| ENSG00000225203.2 | | -2.0992638 | ENSG00000240791.1 | | -1.5212863 | ENSG00000109832.11 | DDX25 | -1.2428493 |
| ENSG00000280989.1 | LINC00581 | -2.0972013 | ENSG00000206875.1 | RNU6-761P | -1.5201144 | ENSG00000252289.1 | | -1.2427871 |
| ENSG00000101812.11 | H2BFM | -2.0920637 | ENSG00000233828.3 | | -1.5198225 | ENSG00000232778.1 | RPL23AP50 | -1.2424691 |
| ENSG00000145920.13 | CPLX2 | -2.09086 | ENSG00000231398.1 | | -1.5178579 | ENSG00000253698.1 | | -1.2421836 |
| ENSG00000163586.8 | FABP1 | -2.0875128 | ENSG00000215148.6 | PRSS41 | -1.5167321 | ENSG00000228453.1 | RPS15AP9 | -1.2420547 |
| ENSG00000207109.1 | | -2.0867157 | ENSG00000225988.1 | LAMP5-AS1 | -1.5166198 | ENSG00000233664.1 | NDUFS5P3 | -1.2420102 |
| ENSG00000197322.3 | C17orf102 | -2.0865956 | ENSG00000171804.8 | WDR87 | -1.5158712 | ENSG00000235284.1 | SNORD62A | -1.2419256 |
| ENSG00000251216.1 | | -2.0862624 | ENSG00000230969.2 | | -1.5153643 | ENSG00000239281.2 | RPS29P2 | -1.241711 |
| ENSG00000213035.4 | RPL23AP80 | -2.0859915 | ENSG00000235833.1 | | -1.5152757 | ENSG00000258654.1 | | -1.2415126 |
| ENSG00000224698.1 | | -2.0843385 | ENSG00000213423.4 | RBMX2P2 | -1.5145285 | ENSG00000019186.8 | CYP24A1 | -1.2413674 |
| ENSG00000243150.4 | | -2.0786366 | ENSG00000279932.1 | | -1.5144147 | ENSG00000232496.2 | RPL3P12 | -1.2411312 |
| ENSG00000251407.1 | MIND1P22 | -2.0784662 | ENSG00000244453.1 | RPL34P21 | -1.5137128 | ENSG00000227982.1 | RPL7P30 | -1.2406996 |
| ENSG00000277109.1 | | -2.0782112 | ENSG00000242894.3 | RN7SL634P | -1.5127893 | ENSG00000259764.1 | PCSK6-AS1 | -1.240504 |
| ENSG00000245729.2 | | -2.0772185 | ENSG00000061192.7 | ANKRD20A9P | -1.5124179 | ENSG00000223665.1 | | -1.2397199 |
| ENSG00000268067.1 | OR5AH1P | -2.0726684 | ENSG00000233995.1 | | -1.5120947 | ENSG00000228386.2 | | -0.238976 |
| ENSG00000258417.3 | | -2.0723937 | ENSG00000243333.3 | RN7SL174P | -1.511759 | ENSG00000222177.1 | RNU4-30P | -1.238777 |
| ENSG00000259389.2 | H3F3AP1 | -2.0717051 | ENSG00000223928.1 | | -1.5115219 | ENSG00000253273.2 | | -1.2366028 |
| ENSG00000222419.1 | RNA5SP511 | -2.0712765 | ENSG00000281639.1 | | -1.5113614 | ENSG00000228035.1 | | -1.2365339 |
| ENSG00000250801.1 | | -2.0711506 | ENSG00000254824.1 | | -1.5112098 | ENSG00000264113.2 | RN7SL784P | -1.2365239 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000229679.1 | | -2.0694147 | ENSG00000261292.2 | | -1.5108502 | ENSG00000258026.1 | | -1.2363734 |
| ENSG00000260211.2 | | -2.0687243 | ENSG00000236417.2 | CTSLP1 | -1.5105645 | ENSG00000270988.1 | | -1.2359711 |
| ENSG00000239988.1 | RPL31P60 | -2.0623278 | ENSG00000264217.2 | RPL35AP25 | -1.5099413 | ENSG00000124939.5 | SCGB2A1 | -1.2354316 |
| ENSG00000277935.1 | | -2.0602189 | ENSG00000258808.1 | | -1.5097369 | ENSG00000221163.1 | | -1.2350317 |
| ENSG00000231924.8 | PSG1 | -2.0537791 | ENSG00000239702.3 | RN7SL507P | -1.509648 | ENSG00000243499.1 | RPS6P21 | -1.2348213 |
| ENSG00000274551.1 | | -2.0532969 | ENSG00000248820.2 | DYNLL1P6 | -1.5091341 | ENSG00000224458.3 | GUSBP6 | -1.2347682 |
| ENSG00000206790.1 | | -2.0507328 | ENSG00000267766.1 | | -1.5086571 | ENSG00000271063.1 | SNRPGP17 | -1.2345946 |
| ENSG00000236900.1 | TIMM9P1 | -2.0493985 | ENSG00000251573.2 | | -1.5090078 | ENSG00000252722.1 | | -1.2344161 |
| ENSG00000189181.4 | OR14I1 | -2.0489776 | ENSG00000227109.1 | CRIP1P3 | -1.5077723 | ENSG00000277105.1 | | -1.2340916 |
| ENSG00000259722.2 | | -2.0487946 | ENSG00000257666.1 | CBX3P5 | -1.5075418 | ENSG00000279924.1 | | -1.23378 |
| ENSG00000269707.1 | | -2.0482829 | ENSG00000228933.6 | | -1.5055647 | ENSG00000249787.1 | | -1.2333104 |
| ENSG00000199398.1 | | -2.0474093 | ENSG00000253502.1 | ATP6V1G1P2 | -1.5054203 | ENSG00000216713.1 | MTND4P13 | -1.2330645 |
| ENSG00000255492.1 | | -2.0467725 | ENSG00000271699.1 | | -1.5043249 | ENSG00000270975.1 | MAGOH3P | -1.2320513 |
| ENSG00000248498.3 | ASNSP1 | -2.0466308 | ENSG00000254567.1 | | -1.503418 | ENSG00000259555.1 | | -1.2320494 |
| ENSG00000249870.1 | | -2.0433809 | ENSG00000244493.1 | SLC9A9-AS2 | -1.5032528 | ENSG00000252496.1 | RNA5SP33 | -1.2318643 |
| ENSG00000239516.1 | FLYWCH1P1 | -2.0424074 | ENSG00000280016.1 | | -1.5021841 | ENSG00000233771.2 | CICP5 | -1.2317085 |
| ENSG00000270994.1 | | -2.0409574 | ENSG00001491124.9 | GLYAT | -1.5020584 | ENSG00000225128.1 | LINC00972 | -1.2313786 |
| ENSG00000201662.1 | RNU6-60P | -2.0408838 | ENSG00000183166.9 | CALN1 | -1.5011542 | ENSG00000279795.1 | | -1.2311386 |
| ENSG00000233848.1 | | -2.0388554 | ENSG00000278683.1 | | -1.5009613 | ENSG00000169393.7 | | -1.2310132 |
| ENSG00000241942.2 | RPS20P20 | -2.0378494 | ENSG00000154898.14 | CCDC144CP | -1.5007776 | ENSG00000270776.1 | ELSPBP1 | -1.2306682 |
| ENSG00000263729.1 | | -2.0372525 | ENSG00000332987.1 | LINC01219 | -1.5005498 | ENSG00000261219.1 | | -1.2303891 |
| ENSG00000131864.9 | USP29 | -2.0353275 | ENSG00000104313.16 | EYA1 | -1.4998575 | ENSG00000169856.8 | ONECUT1 | -1.230276 |
| ENSG00000279966.1 | | -2.0336555 | ENSG00000281675.1 | | -1.499468 | ENSG00000265583.1 | | -1.2301165 |
| ENSG00000259527.2 | LINC00052 | -2.0335629 | ENSG00000183654.8 | 11-Mar | -1.498683 | ENSG00000180723.6 | OR51A9P | -1.2298188 |
| ENSG00000331123.1 | LINC01007 | -2.0332906 | ENSG00000201699.1 | RNU1-59P | -1.4985453 | ENSG00000236321.5 | CROCC2 | -1.2296683 |
| ENSG00000236744.2 | | -2.031241 | ENSG00000253427.1 | | -1.4982085 | ENSG00000251286.2 | | -1.2291958 |
| ENSG00000245482.2 | | -2.0311919 | ENSG00000264226.1 | MIR3168 | -1.4958843 | ENSG00000279681.1 | | -1.2291692 |
| ENSG00000333007.1 | UBTFL11 | -2.0278217 | ENSG00000015592.15 | STMN4 | -1.4949323 | ENSG00000204092.2 | LINC00951 | -1.2291623 |
| ENSG00000254048.1 | | -2.0262445 | ENSG00000227779.1 | | -1.494379 | ENSG00000267146.1 | | -1.2285491 |
| ENSG00000253897.1 | | -2.0256064 | ENSG00000221234.1 | | -1.4943448 | ENSG00000279849.1 | | -1.2265661 |
| ENSG00000154438.6 | ASZ1 | -2.0254416 | ENSG00000253479.4 | LINC01603 | -1.493701 | ENSG00000274537.1 | | -1.2262958 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000168930.12 | TRIM49 | -2.0243862 | ENSG00000213225.7 | | -1.4933344 | ENSG00000164418.18 | GRIK2 | -1.2262898 |
| ENSG00000274664.1 | | -2.0225364 | ENSG00000281196.1 | LINC00934 | -1.4933101 | ENSG00000268660.1 | LETM1P2 | -1.2260597 |
| ENSG00000181867.2 | FTMT | -2.02121 | ENSG00000203648.3 | | -1.4925847 | ENSG00000272167.2 | | -1.225983 |
| ENSG00000242893.3 | RN7SL413P | -2.0186239 | ENSG00000252441.1 | | -1.4913984 | ENSG00000241250.1 | RPL17P20 | -1.2254226 |
| ENSG00000199730.1 | RN7SKP95 | -2.0182279 | ENSG00000256995.5 | | -1.4895477 | ENSG00000280780.1 | JAKMIP2-AS1 | -1.2248646 |
| ENSG00000144285.14 | SCN1A | -2.016492 | ENSG00000227704.1 | | -1.4892587 | ENSG00000279524.1 | | -1.2247028 |
| ENSG00000261043.3 | | -2.0162505 | ENSG00000229000.1 | SEPT7P8 | -1.4885408 | ENSG00000225623.1 | AGBL4-IT1 | -1.2246903 |
| ENSG00000226196.1 | GAPDHP75 | -2.015931 | ENSG00000259791.1 | | -1.4881541 | ENSG00000263667.1 | | -1.2246502 |
| ENSG00000200537.1 | RNY4P6 | -2.015295 | ENSG00000280362.1 | | -1.4880196 | ENSG00000254260.1 | | -1.2239341 |
| ENSG00000227019.2 | OR7E101P | -2.0152703 | ENSG00000202100.1 | | -1.4879121 | ENSG00000223965.2 | ZNF587P1 | -1.2239089 |
| ENSG00000228309.5 | LINC01350 | -2.0144365 | ENSG00000253963.1 | IGLV3-2 | -1.4871723 | ENSG00000215398.10 | | -1.2236659 |
| ENSG00000268080.2 | | -2.0141842 | ENSG00000206808.1 | | -1.4861657 | ENSG00000270171.1 | | -1.2226186 |
| ENSG00000234502.2 | FYTTD1P1 | -2.0109062 | ENSG00000253639.1 | SUMO2P18 | -1.4860975 | ENSG00000277413.1 | | -1.2225576 |
| ENSG00000248843.1 | | -2.0099474 | ENSG00000250577.1 | | -1.4847912 | ENSG00000120563.7 | LYZL1 | -1.222322 |
| ENSG00000270992.1 | | -2.0096264 | ENSG00000207347.1 | RNU6-306P | -1.4847827 | ENSG00000250329.1 | KDELC1P1 | -1.2221338 |
| ENSG00000231712.1 | | -2.0096256 | ENSG00000231301.1 | RPL13AP | -1.4845947 | ENSG00000189423.10 | USP32P3 | -1.2219775 |
| ENSG00000229667.1 | | -2.0088625 | ENSG00000254927.1 | | -1.4839745 | ENSG00000271919.1 | | -1.2216749 |
| ENSG00000253297.1 | | -2.00738 | ENSG00000243902.5 | | -1.4821449 | ENSG00000240056.2 | | -1.2216656 |
| ENSG00000236917.1 | DNAJA1P2 | -2.0059525 | ENSG00000248587.5 | GDNF-AS1 | -1.4820985 | ENSG00000273925.1 | | -1.2209486 |
| ENSG00000248930.1 | | -2.0052429 | ENSG00000237442.3 | HNRNPA1P57 | -1.4820951 | ENSG00000231937.1 | | -1.2201579 |
| ENSG00000222078.1 | RN7SKP110 | -2.0045152 | ENSG00000229623.1 | METTL21AP1 | -1.4778158 | ENSG00000225755.2 | | -1.2195662 |
| ENSG00000246655.3 | OR7E155P | -2.0042299 | ENSG00000281551.1 | | -1.4774147 | ENSG00000229758.4 | VN1R10P | -1.2193377 |
| ENSG00000255458.1 | | -2.0015184 | ENSG00000138829.9 | FBN2 | -1.477208 | ENSG00000213393.5 | | -1.2190777 |
| ENSG00000237896.5 | | -1.9987321 | ENSG00000250710.3 | OR7E99P | -1.4771443 | ENSG00000266240.1 | MIR5091 | -1.2190144 |
| ENSG00000253646.1 | | -1.9964974 | ENSG00000225239.1 | RPL21P107 | -1.4749389 | ENSG00000251724.1 | RNU7-175P | -1.2185941 |
| ENSG00000238040.1 | SALL4P2 | -1.9927433 | ENSG00000224706.1 | RPS17P13 | -1.4740596 | ENSG00000249128.1 | | -1.2183818 |
| ENSG00000255317.1 | | -1.9918431 | ENSG00000170743.15 | SYT9 | -1.4737182 | ENSG00000244232.3 | RN7SL698P | -1.2181572 |
| ENSG00000346601.1 | CHRM3-AS1 | -1.9902825 | ENSG00000201957.1 | | -1.4734506 | ENSG00000275467.1 | | -1.2178498 |
| ENSG00000183432.6 | ZBTB8OSP1 | -1.9899359 | ENSG00000217776.1 | | -1.4730026 | ENSG00000235429.1 | | -1.2178472 |
| ENSG00000226766.1 | FABP7P1 | -1.9884049 | ENSG00000219681.2 | | -1.4723155 | ENSG00000212447.1 | SNORD90 | -1.2175248 |
| ENSG00000277233.1 | | -1.9865474 | ENSG00000189299.6 | FOXR2 | -1.4713111 | ENSG00000236676.1 | | -1.2147575 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000222386.1 | RN7SKP86 | -1.9862277 | ENSG00000241406.3 | RN7SL515P | -1.4706838 | ENSG00000279358.1 | | -1.2145393 |
| ENSG00000231929.2 | HMGB3P31 | -1.9850403 | ENSG00000240299.3 | RN7SL187P | -1.4706241 | ENSG00000075673.10 | ATP12A | -1.2141188 |
| ENSG00000280743.1 | | -1.9833087 | ENSG00000280397.1 | | -1.4701923 | ENSG00000257075.1 | RPEP6 | -1.2140424 |
| ENSG00000191147.8 | C2orf40 | -1.9827394 | ENSG00000237941.2 | KCNQ1DN | -1.4698922 | ENSG00000207029.1 | RNU6-43P | -1.213768 |
| ENSG00000258805.1 | ADIPOR1P2 | -1.9825607 | ENSG00000212257.1 | RNU6-1176P | -1.4696545 | ENSG00000242209.1 | | -1.2131033 |
| ENSG00000253323.4 | LINC01495 | -1.9782662 | ENSG00000232922.1 | | -1.4692833 | ENSG00000185149.5 | NPY2R | -1.212704 |
| ENSG00000276029.1 | MIR4477A | -1.9763376 | ENSG00000281608.1 | | -1.4692534 | ENSG00000264169.2 | RN7SL665P | -1.2114702 |
| ENSG00000242042.1 | | -1.9757482 | ENSG00000228814.4 | | -1.4683942 | ENSG00000214980.4 | | -1.2109204 |
| ENSG00000251360.2 | KHDC1P1 | -1.9755363 | ENSG00000278957.1 | | -1.46616 | ENSG00000200873.1 | RNA5SP399 | -1.210903 |
| ENSG00000265106.1 | | -1.9726284 | ENSG00000259639.4 | | -1.4659133 | ENSG00000184571.12 | PIWIL3 | -1.2106315 |
| ENSG00000253523.1 | | -1.9719401 | ENSG00000221118.1 | | -1.4656338 | ENSG00000232379.1 | | -1.2096301 |
| ENSG00000238032.1 | | -1.9699203 | ENSG00000227538.1 | HNRNPFP1 | -1.4653358 | ENSG00000242162.1 | | -1.2091861 |
| ENSG00000234067.1 | RPL5P10 | -1.9693936 | ENSG00000270313.1 | COX6CP16 | -1.4642495 | ENSG00000201368.2 | | -1.2087722 |
| ENSG00000248704.1 | MTND4P2 | -1.9678641 | ENSG00000253184.1 | | -1.4639902 | ENSG00000267604.1 | | -1.2083488 |
| ENSG00000229105.1 | ASTN2-AS1 | -1.9666995 | ENSG00000214626.2 | POLR3DP1 | -1.4636452 | ENSG00000259461.1 | ANP32BP3 | -1.2080204 |
| ENSG00000231328.1 | TPT1P7 | -1.9650196 | ENSG00000106631.7 | MYL7 | -1.4632348 | ENSG00000237425.1 | RPSAP2 | -1.2079264 |
| ENSG00000243469.1 | RPL7P51 | -1.9648007 | ENSG00000214628.3 | | -1.4628603 | ENSG00000244280.1 | ECEL1P2 | -1.2079186 |
| ENSG00000252181.1 | | -1.9642535 | ENSG00000254090.1 | MTND2P32 | -1.4618486 | ENSG00000215165.3 | TCEA1P3 | -1.207755 |
| ENSG00000270505.1 | IGHV1OR15-1 | -1.960664 | ENSG00000240194.5 | CYMP | -1.461484 | ENSG00000236107.6 | | -1.2075272 |
| ENSG00000207174.1 | SNORD116-15 | -1.9588034 | ENSG00000226331.1 | RPL23AP28 | -1.4612967 | ENSG00000221855.3 | TAS2R41 | -1.2073689 |
| ENSG00000204352.2 | C9orf129 | -1.9585626 | ENSG00000121351.6 | IAPP | -1.4611615 | ENSG00000251490.1 | | -1.2070783 |
| ENSG00000247381.2 | PDX1-AS1 | -1.9576648 | ENSG00000263510.1 | MIR4497 | -1.4611468 | ENSG00000200021.1 | RNA5SP448 | -1.2069769 |
| ENSG00000277979.1 | | -1.9564923 | ENSG00000278658.1 | MIR6826 | -1.4606524 | ENSG00000260733.1 | | -1.2068863 |
| ENSG00000235026.4 | DPP10-AS1 | -1.9547765 | ENSG00000261665.2 | TUBAP4 | -1.4604885 | ENSG00000216307.2 | | -1.2060621 |
| ENSG00000178457.3 | LINC00314 | -1.9547278 | ENSG00000251563.1 | IARS2P1 | -1.4601051 | ENSG00000278483.1 | ECEL1P2 | -1.2058224 |
| ENSG00000266203.1 | MIR5585 | -1.9521919 | ENSG00000259203.1 | | -1.4599384 | ENSG00000254542.1 | NAV2-AS3 | -1.205542 |
| ENSG00000199740.1 | | -1.9518038 | ENSG00000260902.1 | | -1.4577344 | ENSG00000254163.1 | | -1.2052735 |
| ENSG00000271507.1 | | -1.9508539 | ENSG00000259290.1 | MIR4497 | -1.4576936 | ENSG00000230528.6 | NOS2P3 | -1.2051807 |
| ENSG00000253855.1 | | -1.9492576 | ENSG00000201496.1 | RN7SKP275 | -1.4576725 | ENSG00000222732.1 | | -1.2051764 |
| ENSG00000268541.1 | VN1R88P | -1.9490801 | ENSG00000267235.2 | ZNF861P | -1.4554089 | ENSG00000173805.14 | HAP1 | -1.2048494 |
| ENSG00000201725.1 | RNU6-304P | -1.9484671 | ENSG00000228961.1 | | -1.4553871 | ENSG00000233595.2 | MTND2P29 | -1.2048108 |

FIG. 2 (cont.)

| Gene_id | Gene_name | log(FC) | Gene_id | Gene_name | log(FC) | Gene_id | Gene_name | log(FC) |
|---|---|---|---|---|---|---|---|---|
| ENSG00000242545.1 | | -1.9478337 | ENSG00000258437.1 | | -1.4552481 | ENSG00000221333.1 | MIR548K | -1.2045796 |
| ENSG00000251679.1 | | -1.947742 | ENSG00000223918.1 | | -1.4552186 | ENSG00000266543.1 | HSPB6 | -1.204461 |
| ENSG00000270066.3 | | -1.9469685 | ENSG00000254438.1 | | -1.4552052 | ENSG00000004776.10 | | -1.2043165 |
| ENSG00000281247.1 | | -1.9467968 | ENSG00000243715.1 | CACNA2D3-AS1 | -1.4544866 | ENSG00000183643.4 | C15orf32 | -1.2040196 |
| ENSG00000256341.1 | | -1.9467401 | ENSG00000236264.4 | RPL26P30 | -1.4543399 | ENSG00000235097.1 | LINC00330 | -1.2033584 |
| ENSG00000249737.1 | | -1.9462469 | ENSG00000247416.2 | | -1.454231 | ENSG00000243658.1 | MTND5P16 | -1.2031887 |
| ENSG00000276743.1 | | -1.9451548 | ENSG00000232192.1 | | -1.4528994 | ENSG00000280423.1 | | -1.2023338 |
| ENSG00000248103.1 | | -1.9443415 | ENSG00000254404.1 | | -1.4528072 | ENSG00000185940.10 | KRTAP5-5 | -1.2020206 |
| ENSG00000264378.1 | | -1.9431354 | ENSG00000234315.1 | OSTCP5 | -1.4522314 | ENSG00000265121.1 | | -1.2018547 |
| ENSG00000258556.1 | | -1.9412954 | ENSG00000130035.5 | GALNT8 | -1.4522116 | ENSG00000252469.1 | RNU7-160P | -1.2005628 |
| | | | | | | ENSG00000213854.3 | CNN2P6 | -1.2004838 |

FIG. 3

| Name | log (FC) | Name | log (FC) | Name | log (FC) | Name | log (FC) | Name | log (FC) | Name | log (FC) |
|---|---|---|---|---|---|---|---|---|---|---|---|
| 2810454H06Rik | 1.82 | Col5a2 | 1.75 | Gli2 | 1.91 | Kctd11 | 1.37 | Nkd1 | 2.14 | Snai2 | 2.04 |
| AA413626 | 2.39 | Col6a2 | 1.84 | Gm1141 | 1.83 | Khdrbs3 | 2.11 | Nos3 | 2.35 | Snhg18 | 1.62 |
| Abca4 | 2.56 | Col6a3 | 2.17 | Gpc4 | 1.67 | Klhl30 | 2.18 | Nrep | 2.10 | Sobp | 2.05 |
| Abcb4 | 3.20 | Col7a1 | 1.59 | Gpihbp1 | 1.85 | Krt42 | 2.66 | Oacyl | 1.68 | Sox17 | 3.86 |
| Adam12 | 1.53 | Cplx2 | 2.38 | Grem2 | 1.87 | Lama1 | 2.26 | P4ha3 | 1.55 | Sparc | 1.68 |
| Adamts9 | 1.86 | Crabp1 | 1.73 | Gria3 | 2.12 | Lmo7 | 1.55 | Palm2 | 3.80 | Srpx2 | 1.91 |
| Akap12 | 1.96 | Creb3l1 | 1.59 | Gucy1a2 | 2.88 | LOC100504703 | 1.51 | Pcdh12 | 2.56 | St8sia2 | 3.19 |
| Antxr1 | 1.55 | Cspg4 | 2.65 | Hey1 | 2.41 | Lpar4 | 1.77 | Pcdhga10 | 1.53 | Stra6 | 2.27 |
| Atp8b1 | 1.97 | Cthrc1 | 1.76 | Heyl | 2.42 | Lrch2 | 1.89 | Pcsk9 | 2.42 | Syt5 | 2.29 |
| Bgn | 1.66 | Cttnbp2 | 1.57 | Hmx2 | 2.03 | Lrrc15 | 2.33 | Plet1os | 2.87 | Tacr1 | 3.46 |
| Brinp3 | 1.71 | Dmd | 2.00 | Hoxb2 | 2.03 | Lrrc55 | 2.60 | Pnpla3 | 2.10 | Tagln | 2.41 |
| C030037D09Rik | 1.67 | Dysf | 2.02 | Hoxb7 | 2.89 | Mcam | 2.11 | Ppbp | 3.34 | Tbx3 | 1.81 |
| Ccdc80 | 1.70 | Egfl7 | 1.61 | Hoxb8 | 2.97 | Mecom | 1.68 | Prkd1 | 1.73 | Tll1 | 2.28 |
| Cdh2 | 1.72 | Ehd3 | 2.05 | Hoxc8 | 2.01 | Meox1 | 2.42 | Prr9 | 2.40 | Tmem200a | 2.38 |
| Cdkn2b | 2.23 | Emcn | 2.38 | Hs6st2 | 1.89 | Mest | 2.83 | Prss23 | 1.80 | Tmem204 | 1.99 |
| Chsy3 | 1.92 | Emx2 | 1.69 | Htr1b | 4.19 | Mmp15 | 2.34 | Ptprn | 2.48 | Tmem252 | 2.87 |
| Clca1 | 3.71 | Enho | 3.41 | Htr2a | 1.80 | Mmp9 | 1.85 | Rbp1 | 1.89 | Tmem47 | 2.16 |
| Cldn5 | 2.37 | Epha3 | 2.02 | Igfbp3 | 2.08 | Mmrn1 | 1.81 | Rnf223 | 1.99 | Tnc | 2.14 |
| Clec11a | 1.98 | Erg | 2.46 | Igfbp7 | 1.95 | Msx1 | 1.98 | Ror2 | 2.03 | Tspan6 | 1.92 |
| Clhc1 | 3.97 | Fam198b | 1.90 | Itgb3 | 1.57 | Mxra7 | 1.88 | Serp2 | 1.75 | Ttc41 | 1.57 |
| Cnih2 | 1.88 | Fam46b | 1.79 | Jph2 | 2.13 | Myh11 | 3.10 | She | 1.79 | Unc5c | 2.42 |
| Col11a1 | 2.70 | Fhl1 | 2.12 | Kcnb1 | 1.53 | Myl9 | 2.23 | Slc12a3 | 2.45 | Usp13 | 2.18 |
| Col12a1 | 1.72 | Fjx1 | 1.94 | Kcne3 | 3.51 | Ncam1 | 1.88 | Slc3a1 | 2.00 | Wnt11 | 2.32 |
| Col15a1 | 2.27 | Fmod | 3.11 | Kcnip4 | 1.99 | Ndst3 | 1.54 | Slc5a5 | 2.64 | | |
| Col4a2 | 1.56 | Gata6 | 2.03 | Kcnmb1 | 2.26 | Nexn | 1.76 | Slc8a3 | 3.63 | | |
| Col5a1 | 1.63 | Gcnt4 | 2.13 | Kcnq3 | 1.74 | Nid2 | 1.79 | Slit2 | 1.60 | | |

FIG. 4

| Name | log (FC) |
|---|---|
| Glyctk | -1.50 |
| Sesn1 | -1.53 |
| Gm4013 | -1.56 |
| C1qa | -1.79 |
| Nr3c2 | -1.84 |
| Cd200r4 | -1.97 |
| Mag | -1.99 |
| Slc15a2 | -2.03 |
| Lrfn1 | -2.05 |
| Lefty1 | -2.06 |
| Crym | -2.24 |
| Gm13710 | -2.31 |
| Gpr82 | -2.33 |
| Ccl12 | -2.47 |
| Aoah | -2.62 |
| Omp | -2.63 |
| Cd226 | -2.67 |
| Epor | -2.94 |
| Rab39 | -3.02 |
| Gzma | -3.24 |
| Sectm1a | -3.44 |
| Gm13154 | -3.51 |
| Rnase6 | -3.71 |
| Cxcl13 | -5.76 |

LEFT-RIGHT GENE EXPRESSION SIGNATURE FOR TRIPLE NEGATIVE BREAST CANCER

CROSS REFERENCE TO RELATED APPLICATION

This application claims filing benefit of U.S. Provisional Patent Application Ser. No. 62/461,262 having a filing date of Feb. 21, 2017, which is incorporated herein by reference in its entirety.

BACKGROUND

The heterogeneity of breast cancer poses a formidable challenge for effective treatment, risk management, and disease prevention, especially for patients whose tumors lack targeted therapies. This problem is particularly acute for patients diagnosed with triple negative breast cancer (TNBC), a highly aggressive clinical subtype that is refractory to currently available targeted therapies due to lack of ER/PR/HER2 expression. The molecular diversity of TNBC, present even within genomically defined 'intrinsic' tumor subtypes, confounds discovery of biomarkers and cognate drug targets.

What are needed in the art are materials and methods for improved diagnosis and treatment of TNBC. For instance, materials and methods that can improve determination of the risk of malignancy in TNBC would be highly beneficial. Moreover, materials that can lead to improved outcomes for patients diagnosed with cancer (e.g., enable new drug discovery, recognition of significant biomarkers, etc.) would be of great benefit.

SUMMARY

According to one embodiment, disclosed are binding arrays, e.g., hybridization or other specific binding arrays such as genomic or proteomic microarrays, that can be used for diagnostic, therapeutic, and research purposes, among others. The binding arrays include binding agents developed based upon the recognition of heterogeneity between left-arising and right-arising breast cancer tumors.

In one embodiment, the binding arrays can include binding agents (e.g., DNA or RNA segments, proteins or fragments thereof, natural or synthetic small molecule binding agents, etc.) that specifically bind materials related to genes that are expressed to a significantly different level in left TNBC tumors as compared to right TNBC tumors. For instance, the binding agents can bind complete or partial sequences of the genes themselves, complete or partial RNA transcription sequences, proteinaceous expression products or fragments thereof, down-stream proteinaceous and/or non-proteinaceous products related to the overexpressed genes, etc. For instance, a binding array can include a first portion that includes binding agents designed to specifically bind materials representative of genes that are significantly over-expressed in right TNBC tumors as compared to their expression levels in left TNBC tumors. A binding array can also include a second portion that includes binding agents designed to specifically bind materials representative of genes that are significantly over expressed in left TNBC tumors as compared to their expression levels in right TNBC tumors.

In another embodiment an array can include as binding agents the materials related to genes that are expressed in TNBC to a significantly different level in left TNBC tumors as compared to right TNBC tumors. For instance, the binding agents of the array can include a plurality of genes or expression products thereof (or a portion thereof) that are over-expressed in left and/or right TNBC tumors. In one embodiment, an array can be a hybridization array that includes a plurality of complete or partial RNA transcripts that are over-expressed in left and/or right TNBC tumors. In another embodiment, an array can be a peptide array that includes binding epitopes of proteinaceous products of over-expressed genes in left and/or right TNBC tumors. Downstream proteinaceous and/or non-proteinaceous products related to the overexpressed genes can likewise be included as binding agents of a binding array.

According to another embodiment, a method is disclosed for determination of the risk of malignant TNBC in a subject. This method can include obtaining a sample from a subject and determining that the sample includes expression products (or related products) of a plurality of genes at levels that are significantly different from control levels. In addition, the plurality of genes can be genes that are known to be expressed at significantly different levels (e.g., higher levels) in right TNBC tumors as compared to their expression levels in left TNBC tumors. Upon this determination, the subject can be determined to be at high risk for malignant TNBC and can be monitored or treated appropriately.

BRIEF DESCRIPTION OF THE FIGURES

A full and enabling description of the present disclosure, including the best mode thereof to one skilled in the art, is set forth more particularly in the remainder of the specification, which includes reference to the accompanying figures, in which:

FIG. 1 is a table presenting human genes that are upregulated by 2-fold or more in left TNBC tumors as compared to their expression levels in right TNBC tumors.

FIG. 2 is a table presenting human genes that are upregulated by 2-fold or more in right TNBC tumors as compared to their expression levels in left TNBC tumors.

FIG. 3 is a table presenting mouse genes that are upregulated by 2-fold or more in right TNBC tumors as compared to their expression levels in left TNBC tumors.

FIG. 4 is a table presenting mouse genes that are upregulated by 2-fold or more in left TNBC tumors as compared to their expression levels in right TNBC tumors.

DETAILED DESCRIPTION

Figure 5:
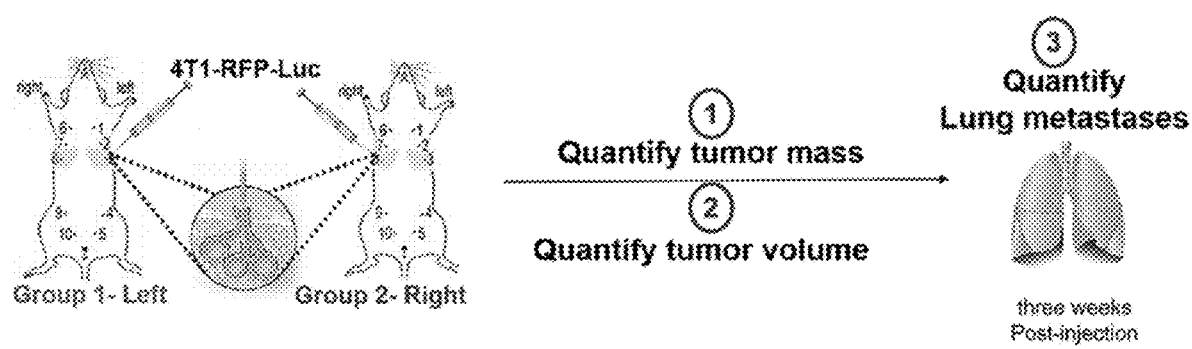
FIG. 5 schematically illustrates an experimental procedure followed for left/right intraductal injection of mammary carcinoma cells into experimental groups as described herein.

Reference now will be made to embodiments of the disclosure, examples of which are set forth below. Each example is provided by way of an explanation of the disclosure, not as a limitation of the disclosure. In fact, it will be apparent to those skilled in the art that various modifications and variations can be made in the disclosure without departing from the scope or spirit of the disclosure. For instance, features illustrated or described as one embodiment can be used on another embodiment to yield still a further embodiment. It is to be understood by one of ordinary skill in the art that the present discussion is a description of exemplary embodiments only, and is not intended as limiting the broader aspects of the present disclosure, which broader aspects are embodied in exemplary constructions.

In general, disclosed are methods and materials that can be used for clinical and research applications directed to cancers, and in one particular embodiment directed to TNBC. The disclosed methods and materials are based upon a previously unappreciated source of tumor heterogeneity: left right (LR) positional differences. More specifically, distinct expression signatures have been discovered between TNBC tumors originating in the left breast as compared to tumors originating in the right breast, suggesting differential tumor cell regulation occurs in left versus right breasts. As described further herein, findings indicate that the right mammary microenvironment promotes tumor metastasis, while, surprisingly, the left microenvironment attenuates metastatic activity. Without wishing to be bound to any particular theory, is believed that tumors develop distinct L-R genomic signatures as a consequence of L-R asymmetric interactions, and that this outcome in turn shapes malignant potential, for instance through altering a gene expression program that optimizes tumor cell survival/proliferation upon reaching the metastatic niche.

The unique expression signatures described herein can be used in development of beneficial diagnostic devices, e.g., DNA/RNA microarrays, protein microarrays, small molecule microarrays, etc., that can be based upon the significant difference in expression for a number of genes between left and right tumors. Moreover, disclosed devices are not limited to utilization in conjunction with TNBC, and are believed to be useful in conjunction with other breast cancer, particularly with other breast cancer research.

The unique expression signatures as well as devices developed therefrom can be utilized in both clinical and research applications. For instance, in one embodiment, a method can be utilized for risk assessment of a cancer. In this embodiment, a method can include analysis of a test sample with focus on the expression signature of genes known to exhibit significantly higher expression levels in right TNBC tumors as compared to left TNBC tumors. Such methods can determine that an individual is at higher risk for more aggressive tumor growth and malignancy. For instance, a binding array can be designed such that the binding agents of the array specifically bind expression products of genes that are significantly over-expressed in right TNBC tumors, which can be indicative of more aggressive and malignant cancers. Such methods can be utilized as a diagnostic tool for high risk TNBC and can be utilized in conjunction with other traditional diagnostic and treatment procedures The unique expression signatures can also be utilized as a development tool for providing additional understanding of breast cancer in general and TNBC in particular as well as in development of new therapies for cancer treatment. For instance, a binding array can be designed such that the binding agents of the array include the genes themselves (or portions thereof) or expression products (or portions thereof) of the genes that are over-expressed in left TNBC tumors, in right TNBC tumors, or in both. In some embodiments, the binding array can include as binding agents materials that specifically bind to the genes themselves or expression products of the genes (e.g. complementary nucleic acid sequences, antibodies, etc.). The materials and methods can be utilized to uncover new mechanistic information on TNBC metastasis and in turn, to identify candidate biomarkers and therapeutic targets for breast cancers that are otherwise being missed in more traditional analyses. The information can be utilized in determination of the molecular and cellular basis of the L-R differences, with the rationale that asymmetrically active pathways that suppress vs. support TNBC metastasis represent untapped, left vs. right breast-specific biomarkers and therapeutic targets for TNBC as well as other breast cancers that are otherwise being missed in L-R aggregate analyses.

The arrays may be used in drug discovery and research methods. For example, the arrays may be used to determine responses of one or more of the genes/RNA transcripts/protein expression products/etc. of the differently expressed genes to experimental therapeutic agents, newly synthesized compounds and other agents of interest. The agents may be known to have therapeutic use or may be newly created candidate therapeutic agents.

As such, the binding arrays can be useful for screening one or a large number of candidate agents for the ability to modulate target cell or tissue function. In accordance with one embodiment of the method, a binding pattern on one or more of the arrays for a sample that includes or that has been treated with the therapeutic agent candidate can be compared with a binding pattern for a control sample. A difference between binding of elements of the treated sample and the control sample can be indicative of the ability of the candidate agent to bind to the target (e.g., directly bind a genetic expression product on the array) or to modulate a target of a treated sample.

FIG. 1-FIG. 4 provide exemplary lists of genes that are expressed in TNBC tumors to a significantly different degree in right and left tumors. Included in the figures are a listing of genes that are significantly upregulated in humans diagnosed with left TNBC tumors as compared to human right TNBC tumors (FIG. 1), and genes that are significantly upregulated in humans diagnosed with right TNBC tumors as compared to left TNBC tumors (FIG. 2). FIG. 3 includes a listing of genes that are upregulated in mice having right TNBC tumors as compared to left TNBC tumors, and FIG. 4 includes a listing of genes that are upregulated in mouse left TNBC tumors as compared to right TNBC tumors. Information on the figures include the Gene Symbol GENCODE Gene Identification number (Gene ID), the common name for the gene (if known) and the $\log_2$ of the fold change in expression level as compared to the opposite breast. As utilized herein a significant difference in gene expression can generally refer to a fold change in expression of about 2 or more. As shown, FIG. 1-4 provide genes having a two-fold or greater increase in expression as compared to the expression of the same gene in the opposite breast (i.e., $\log_2$ (FC) is 1 or greater).

As can be seen by reference to FIG. 1-FIG. 4, genes that are expressed to a significantly different degree in LR tumors can be found in a large number of different pathways. Accordingly, binding arrays can be designed to examine one or more pathways as indicated by the genes. For instance, a binding array can include only those genes that are in one (or more) particular pathways of interest.

In one embodiment, a binding array can include a plurality of polynucleotides as the binding agents. For example, a binding array can include a plurality of polymeric nucleic acid elements arranged to produce a single transcriptome array e.g., a single array including only transcriptomes that are upregulated in right TNBC tumors or a single array including only transcriptomes that are upregulated in left TNBC tumors. In other embodiments an array can include nucleic acid elements corresponding to both left and right TNBC tumors, for instance as different portions (e.g., different panels or areas) of a single binding array. For a given array, each nucleic acid element may be a whole sequence or a sequence fragment, with different elements having the same or different lengths. In addition, an array can include multiple fragments of a whole sequence, and each fragment can be present any number of individual times, though it is not necessary that all fragments constituting a whole sequence be present on the array.

In general, binding elements representative of the genes of interest can be immobilized on an array at a plurality of physically distinct locations using immobilization or binding techniques well known in the art. For instance, fragments at several physically distinct locations may together compose an entire transcript or discreet portions of a transcript. Fragments may be complementary to contiguous portions of a transcript or noncontiguous portions of a transcript. Hybridization of a nucleic acid molecule from a target sample to the fragments on the array is indicative of the presence of the target transcript in the sample. Hybridization and detection of hybridization can be performed by routine detection methods well known to those skilled in the art.

In one embodiment, multiple binding agents can be used in order to distinguish a target sequence from other nucleic acid sequences in a sample. In one embodiment, 2% or more of a target sequence is represented by (e.g., complementary to) one or more binding agents on an array. In further embodiments, at least 5%, at least 10%, at least 20%, at least 30%, at least 40%, at least 50%, at least 60%, at least 70%, at least 80%, or at least 90% of a target sequence is represented by one or more binding agents on an array. Hybridization of nucleic acid sequences (i.e., either whole transcripts or fragments) in a sample to nucleic acid binding agents on an array can be representative of the presence of the full transcript in a sample.

In another embodiment, a nucleic acid element corresponding to a whole transcript or a fragment of a whole transcript can be immobilized on an array at only one physically distinct location in a "spotted array" format. Multiple copies of the specific nucleic acid element may be bound to the array substrate at the discreet location.

One of skill in the art will appreciate that nucleic acid elements on a given array are complementary to the targeted sequences in a given sample. Arrays containing the native sequences may also be designed to identify the presence of antisense molecules in a target sample. Endogenous antisense RNA transcripts can be of interest at least due to the implication of endogenous antisense in cancer.

When considering nucleic acid-based binding arrays, elements from a sample can be hybridized to the array under conditions selected to provide a suitable degree of stringency. The skilled person is well aware of techniques for varying hybridization conditions in order to select the most appropriate degree of stringency for a particular sample. For example, using a non-stringent wash buffer (such as 6×SSPE, 0.01% Tween-20) and a stringent buffer (such as 100 mM MES, 0.1M [Na$^+$], 0.01% Tween-20) a person or ordinary skill in the art can alter the number of respective washes (typically 0-20), the wash temperature (typically 15-50° C.) and hybridization temperature (typically 15-50° C.) to achieve optimal hybridization.

In one embodiment, protein-based binding arrays can be designed and constructed. As used herein, the terms "protein" and "polypeptide" are interchangeable. Binding agent elements in these arrays may include proteins, peptides, antibodies, peptide-nucleic acid conjugates and the like. In one embodiment, a protein array can include polypeptide molecules encoded by the disclosed genes immobilized in discreet locations. In another embodiment, antibodies generated to polypeptide molecules encoded by disclosed genes may be immobilized on an array in discreet locations. Antibodies of a binding array can be polyclonal or monoclonal. A complete antibody or a fragment thereof (e.g., Fab or F(ab')2) including a binding epitope can be used.

In another embodiment a binding array can include as binding agents materials that are either polymeric or non-polymeric in nature and that are not necessarily polynucleotides or proteinaceous. For instance, specific binding agents that are synthetic and non-proteinaceous designed to bind an expression product of a gene as disclosed herein can be included in a binding array.

Binding agents of an array can be labeled to include a detectable substance. The term "labeled", with regard to either a binding agent of an array or a component of a sample is intended to encompass direct labeling by direct coupling (i.e., physically linking) a detectable substance to the material (e.g., a binding agent or a component of a sample to be tested), as well as indirect labeling by coupling a binding agent or a component of a sample with another reagent that is directly labeled. Examples of indirect labeling include detection of a primary antibody using a fluorescently labeled secondary antibody and end-labeling of a DNA probe with biotin such that it can be detected with fluorescently-labeled streptavidin. By way of example, polypeptides of a system can be conjugated with detectable labels, e.g., through conjugation of an antibody with another labeled polypeptide. A sample may be contacted with the labeled array and displacement of the label (e.g., a labeled protein) from an immobilized antibody can be visible by a loss of the detectable label in that discreet location on the array. Profiles of protein displacement on an array can be, for example, correlated with the responsiveness or unresponsiveness of an individual affected with a cancer, e.g., TNBC, to a therapeutic agent. Other examples of labeling approaches are known and well within the capabilities of one of skill in the art.

Labels may be incorporated before, during or after binding of a binding agent to a substrate during formation of an array or before, during, or after binding of a component of interest to a binding agent during use of an array by any suitable means of attaching labels known in the art. Suitable means may include addition of a label directly to an agent, e.g., an original transcript element (e.g., mRNA, polyA mRNA, cDNA, etc.) or to an amplification product during or after amplification of a transcript-specific element of a sample, e.g. using labeled primers or labeled nucleotides.

Labels suitable for use in the methods described herein include, but are not limited to, biotin for staining with labelled streptavidin conjugate, magnetic beads (e.g., Dynabeads™), fluorescent dyes (e.g., fluorescein, Texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Depending on the choice of label, the skilled person will be able to choose suitable means for detection of the label well known in the art.

Any suitable substrate can be used as the solid phase to which the binding agent elements are immobilized or bound. For example, the substrate can be glass, plastics, metal, a metal-coated substrate or a filter of any material. The substrate surface may be of any suitable configuration. For example the surface may be planar or may have ridges or grooves to separate the elements immobilized on the substrate. In one embodiment, the binding agents can be attached to particles, e.g., beads, that can be separately identifiable. The binding elements can be attached to a substrate in any suitable manner that makes them available for use in the binding array, including covalent or non-covalent binding.

One of ordinary skill will appreciate that several methods are available for attaching molecular binding agents to a substrate of an array. Attachment methods may include, without limitation, covalent bonding, ionic bonding, UV crosslinking, and attachment via pairs of affinity molecules. Non-limiting examples of affinity pairs include, but are not limited to, biotin and avidin, biotin and streptavidin, receptor and ligand, antibody and ligand, antibody and antigen, and a polynucleotide sequence and its complement. In certain embodiments, pairs of affinity molecules that are bound may be unbound. For example, a polynucleotide sequences that are hybridized may be denatured, and biotin bound to streptavidin may be heated and become unbound.

In one embodiment, the binding agents may be grouped on an array by function, e.g., according to level of upregulation in TNBC tumors, according to biochemical pathway, etc. In one embodiment, such groupings can provide regions on an array where binding results are indicative of responsiveness to a therapeutic agent of interest.

Methods of arraying macromolecules are well-known in the art. Typically, arrays comprise micrometer-scale, two-dimensional patterns of patches of macromolecules (i.e., binding agents) immobilized on an organic thin-film coating on the surface of the substrate. Examples of arrayed macromolecule chips, including array pattern and density, substrates, coatings and organic thin-films are described in the art, for example, U.S. Pat. Nos. 6,329,209; and 6,365,418, each of which is incorporated by reference herein.

In one embodiment, an array can include a substrate, at least one organic thin-film covering some or all of the surface of the substrate, and a plurality of patches arranged in discrete, known regions on the portions of the substrate surface covered by organic thin-film, wherein each patch includes binding agents immobilized on the organic thin-film, and wherein each of the binding agents of a given patch binds a particular cognate binding partner in a collection. In general, an array can include between about 10 and about 10,000 binding agents that can be the same or different from each other. For instance, each binding agent can bind a different cognate binding partner in a collection or an array can include a plurality of each of several different binding agents.

Binding agents of an array are generally covalently immobilized on patches or areas of the array, either directly or indirectly. For example, protein A may be used to orient an antibody with the binding region above the substrate surface so as to be available for binding a material of interest in a sample.

Disclosed arrays can be used to test a sample for the presence and/or quantity of materials of interest in a test sample. As used herein, the term "test sample" generally refers to a material that contains or is suspected of containing a material of interest (e.g., a biomarker, or a potential drug of interest). The test sample may be a synthetically derived solution (e.g., a research solution) or may be derived from any biological source, such as a physiological fluid, including, blood, plasma, serum, interstitial fluid, saliva, cerebrospinal fluid, sweat, urine, ascites fluid, mucous, nasal fluid, sputum, peritoneal fluid, and so forth. A test sample may be used directly as obtained from a subject or following a pretreatment to modify the character of the sample. For example, such pretreatment may include isolating plasma from blood, collection and drying of blood on filter paper (dry blood spots) diluting viscous fluids, and so forth. Methods of pretreatment may also involve elution, filtration, precipitation, dilution, distillation, mixing, concentration, inactivation of interfering components, the addition of reagents, lysing, etc. Moreover, it may also be beneficial to modify a solid test sample to form a liquid medium or to release the material of interest (the analyte).

Any suitable target tissue or cell may be examined by use of disclosed binding arrays. It will be understood by those skilled in the art that the term "diseased tissue sample" includes abnormal samples, samples suspected of being diseased, and normal samples that are analyzed as part of a routine screening examination.

A sample can be processed to obtain one or more specific elements, which are then combined with the array to allow binding/hybridization and detection of the elements bound to the array. The term specific element as used herein can include transcript-specific elements, which include any suitable nucleic acid derived from an RNA transcript in a sample, such as DNA or RNA. A nucleic acid derived from an RNA transcript may be a cDNA reverse-transcribed from an mRNA, an RNA transcribed from such cDNA, a DNA amplified from the cDNA, an RNA transcribed from the amplified DNA, etc. Where it is of interest to determine alterations in the copy number of a gene, genomic DNA can be utilized. Alternatively, where expression levels of a transcript or transcripts are of interest, RNA or cDNA can generally (though not exclusively) be used. For example, in order to quantify expression, a transcript-specific element may be any type of transcribed RNA molecule such as messenger RNA (mRNA), alternatively spliced mRNA, ribosomal RNA (rRNA), transfer RNA (tRNA), and a large range of other transcripts which are not translated into protein, such as small nuclear RNA (snRNA), and antisense molecules such as siRNA and microRNA. The transcript-specific element may also be a nucleic acid derived from RNA.

Depending on the sample size and method of isolation, transcript-specific elements may be used with or without amplification. Suitable amplification methods include, but are not limited to, polymerase chain reaction (PCR), ligase chain reaction (LCR), transcription amplification, and self-sustained sequence replication.

In certain embodiments, only the presence or absence of a particular element of a sample is of interest. In such cases, the detection of a binding/hybridization signal is indicative of the presence of the elements in the sample. In other embodiments, it may be desired to quantify the expression of one or more specific elements in a sample. In such cases, an array can be designed such that the concentration of specific elements in the sample is directly or indirectly proportional to the detected signal. The skilled person will understand that the proportionality need not be strict (e.g., a doubling in transcription rate resulting in a doubling in mRNA transcript and a doubling in hybridization signal). A more relaxed proportionality, for example, where a 10-fold difference in concentration of the target results in a 5 to 15-fold difference in signal intensity may be acceptable. Where more precise quantification is required appropriate controls can be run to correct for variations introduced in sample preparation and binding, according to known practice.

In one embodiment, a binding array can include all of the genes exhibiting about a 2-fold change in expression or greater in either the left or right TNBC tumor as compared to the other. For instance, a binding array can include binding agents related to all of the genes of FIG. 1 and FIG. 2. In other embodiments, a binding array can include materials related to only a portion of genes exhibit a significantly different expression level in left vs. right TNBC tumors. For instance, a binding array can include materials related to only those genes involved in a particular pathway or a particular set of pathways. In another embodiment a binding array can include only materials related to genes that are overexpressed in right TNBC tumors or only genes that are overexpressed in left TNBC tumors. A binding array can include materials that are overexpressed to a greater or lesser degree. For instance, a binding array can be limited to only those materials related to genes that are over-expressed by a 3-fold change or greater, by a 4-fold change or greater, or by a 5-fold change or greater in some embodiments.

In one embodiment, a binding array can be utilized to assess the risk for a particular TNBC to be malignant. As discussed further herein, it has been determined that right TNBC tumors are at higher risk for aggressiveness and malignancy. Accordingly, determination that a TNBC-derived sample is upregulated in expression for a plurality of genes known to be overexpressed in right TNBC tumors (e.g., a plurality of genes of FIG. 2), the subject can be determined to be at high risk for malignant TNBC and appropriate monitoring and treatment can be carried out (e.g., aggressive chemotherapy, surgery, additional testing, etc.).

A test sample need not be upregulated in expression for all of the genes of Table 2 in order for the high risk determination to be made. For instance, a test sample that is upregulated in expression to a significant degree (e.g., 2-fold or more, 3-fold or more, or 4-fold or more over a normal physiological expression level) for 10% or more, 20% or more, 30% or more, 40% or more, 50% or more, 60% or more, 70% or more, 80% or more, or 90% or more of the genes of Table 2 can be indicative of a high risk cancer The present disclosure may be better understood with reference to the Examples, below.

Example 1

Figure 6:
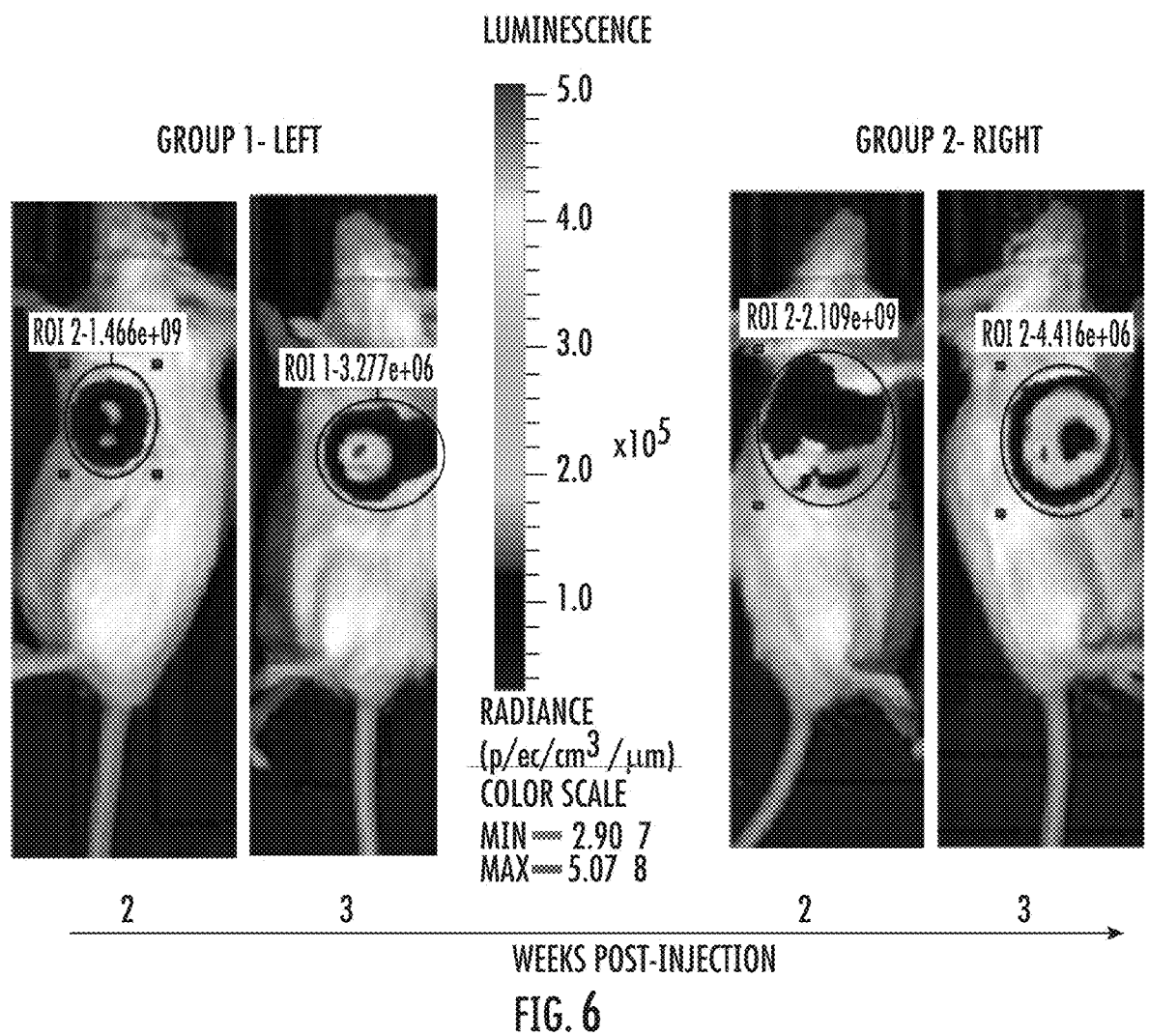
FIG. 6 illustrates representative tumors from each of the left tumor and right tumor groups.
Figure 7:
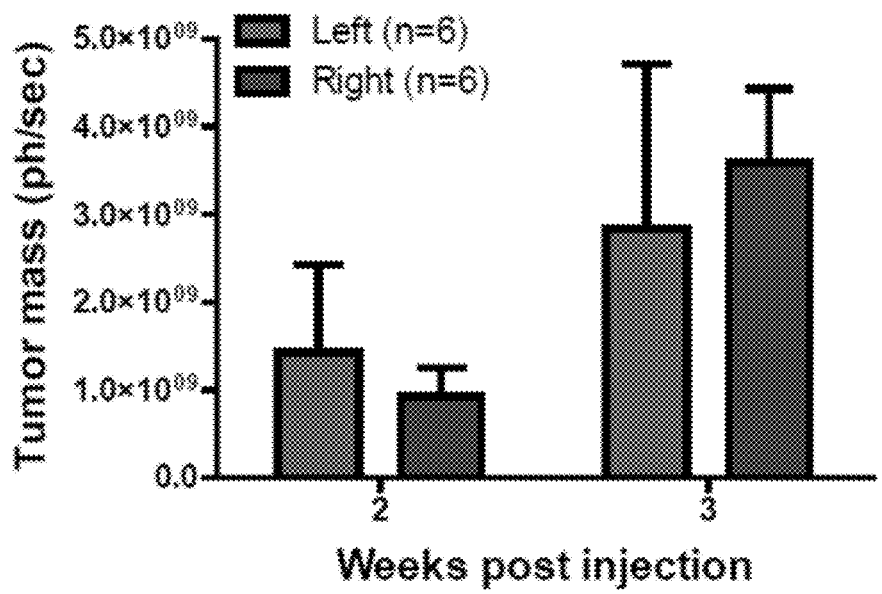
FIG. 7 compares the tumor mass for left and right TNBC tumors in the different tumor groups.
Figure 8:
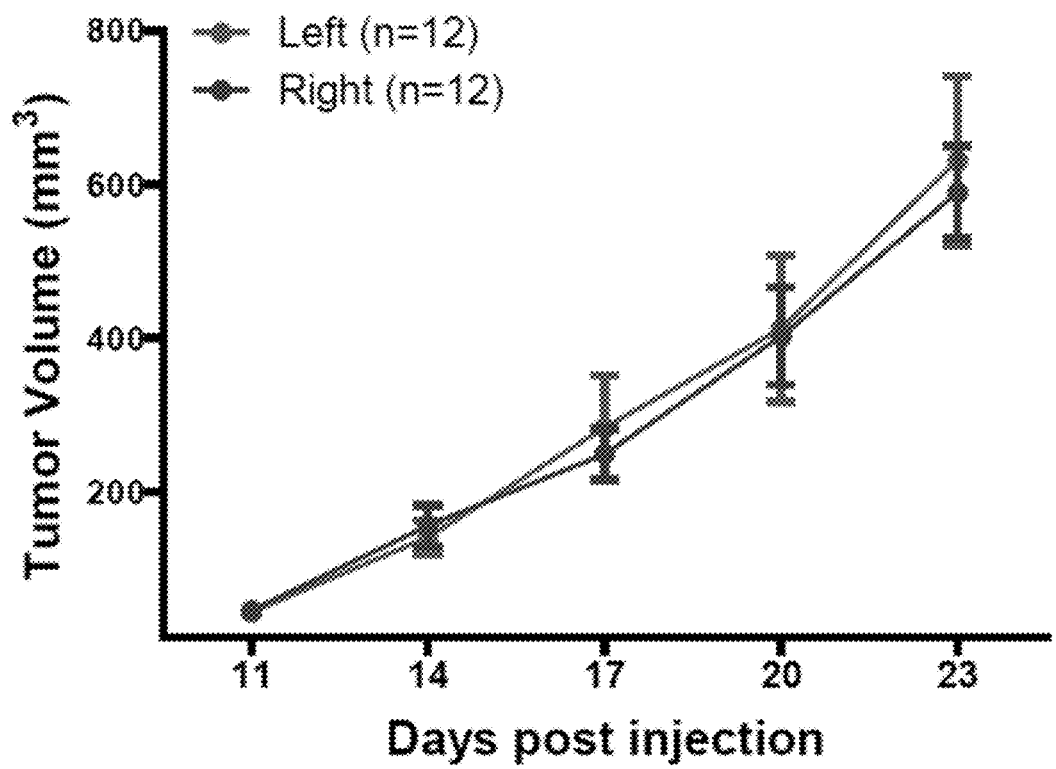
FIG. 8 compares the tumor volume for left and right TNBC tumors in the different tumor groups.
Figure 9:
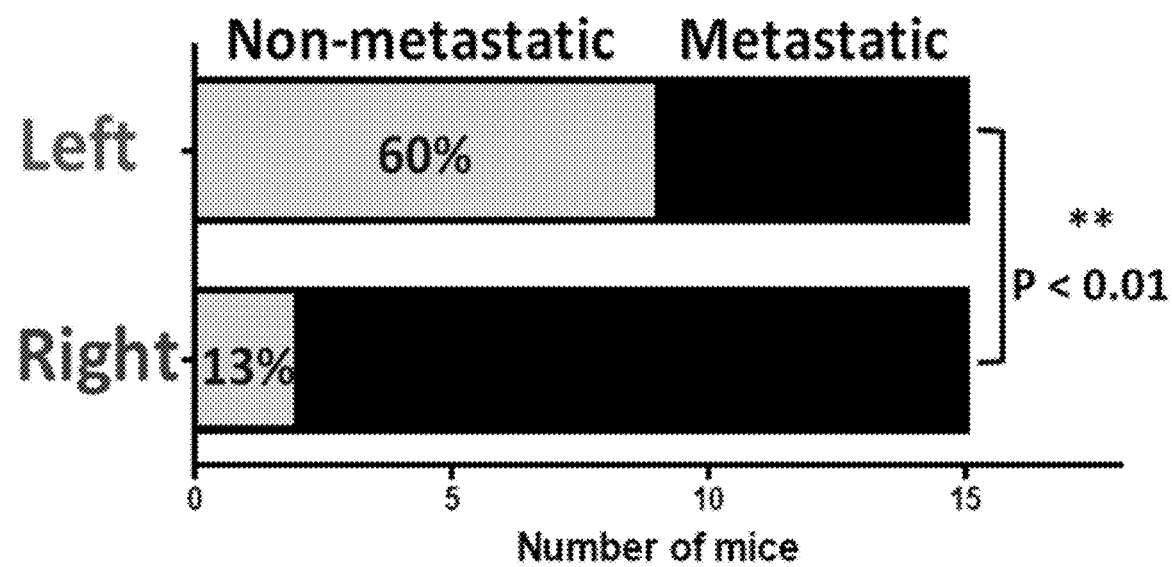
FIG. 9 presents the variation in the left/right groups with regard to macrometastases quantification.
Figure 10:
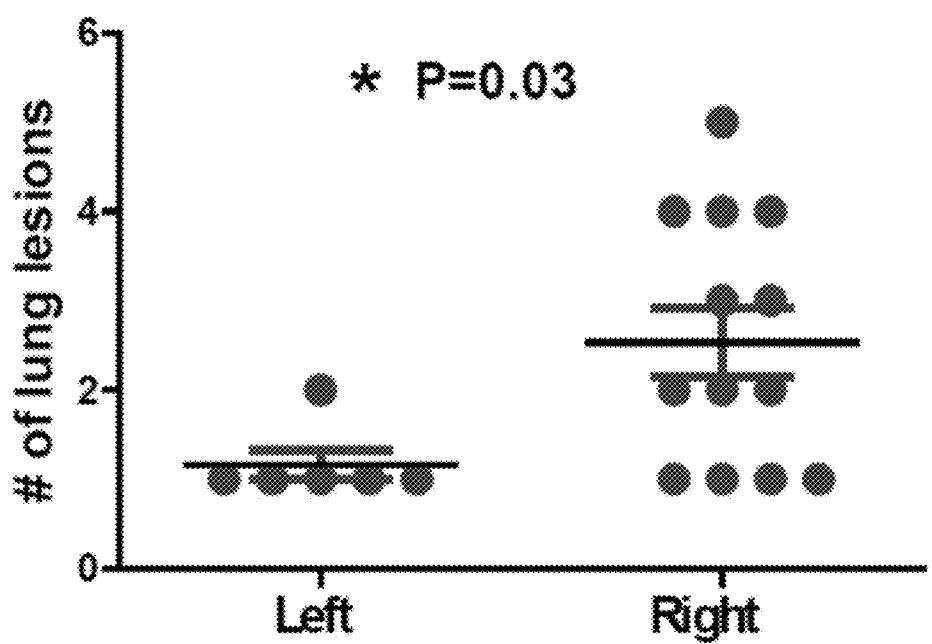
FIG. 10 presents the variation in the left/right groups with regard to lung lesion presence.

To determine if there are L-R differences in microenvironmental support of TNBC tumors, functional studies using the 4T1 TNBC mouse model were carried out. Metastatic 4T1-RFP-luc (Red Fluorescent Protein; luciferase) mammary carcinoma cells were intraductally injected into the left or right thoracic mammary glands of adult female mice (FIG. 5). Tumor take and growth were equivalent in the left and right groups as quantified by bioluminescent imaging (see representative mice in FIG. 6). Tumor mass (FIG. 7) and tumor volume (FIG. 8) were roughly equivalent between left and right groups. Histologically detectable lung metastases were present in all but two mice in the right tumor group (87%). By contrast, only 40% of mice in the left tumor group had lung lesions (FIG. 9). Moreover, when quantifying the macrometastases present in mice from both groups, right tumors gave rise to larger (not shown) and higher numbers of lesions (FIG. 10).

Figure 11:
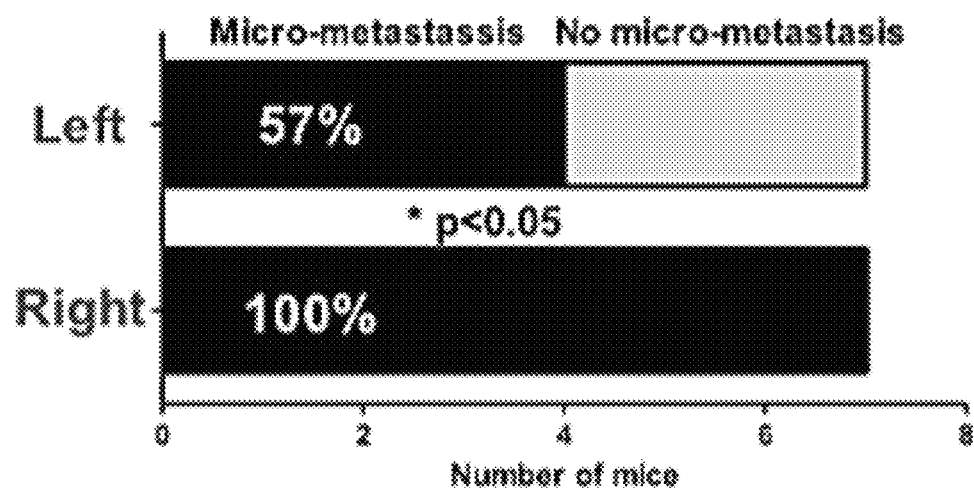
FIG. 11 presents the variation in the left/right groups with regard to micrometastases quantification.

To determine if L-R differences were due to differential tumor cell dissemination, a 6-thioguanine assay was used to quantitatively detect lung micrometastases. Significantly higher numbers of mice with right-side tumors (100%) had micro-metastases compared to mice bearing left-side tumors (57%) (FIG. 11). Thus the feature of tumor cell dissemination is more aggressive in right-side tumors compared to left-side tumors.

To determine if left-side tumors remain non-metastatic, experiments were repeated with later endpoint analysis. It was found that most left-side tumors eventually did metastasize with incidence comparable to right-side tumors (83% left group versus 100% right group; N=12, P=0.24), but the size and number of lung nodules nevertheless were decreased compared to those arising from right-side tumors.

Example 2

Using assembled RNA-Seq transcriptomes deposited in The Cancer Genome Atlas (TCGA) left (N=55) and right (N=54) human TNBC tumors were profiled for significant L-R differences based on >5.5-fold differential gene expression ($P<0.05$).

Out of 42,335 total transcripts, the analysis identified 39 up-regulated transcripts with common gene names in left tumors (FIG. 1) and 136 transcripts with common gene names upregulated in right tumors (FIG. 2), indicating the existence of distinct L-R signatures in human TNBC.

Figure 12:
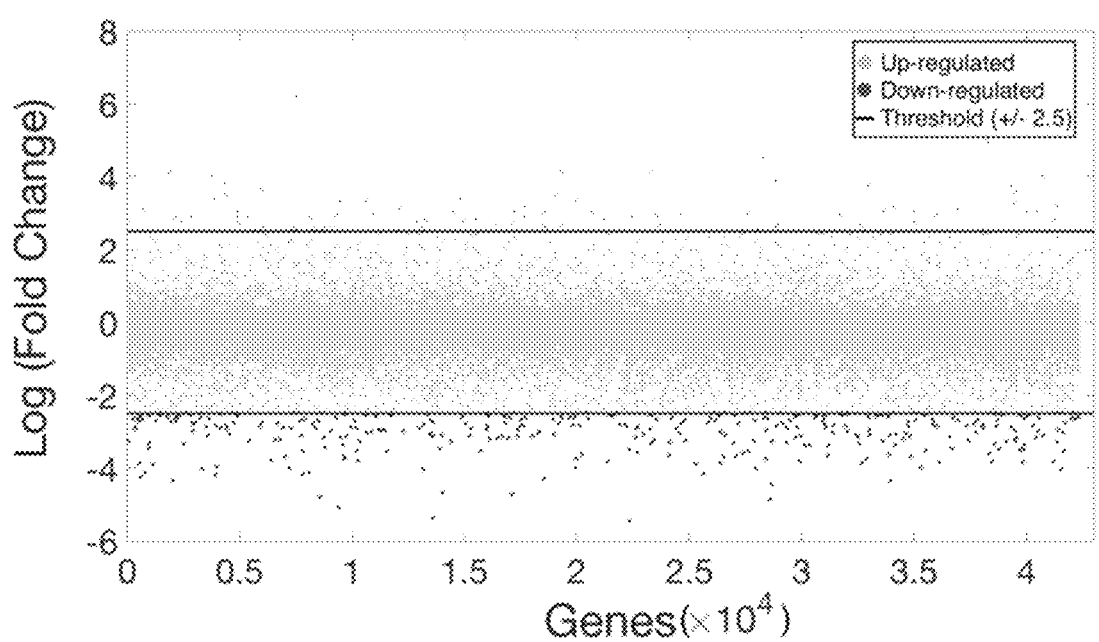
FIG. 12 is an MA plot of RNA-Seq analysis of left vs. right human TNBC tumors formed in development of the tables of FIG. 1 and FIG. 2.

Patient gene counts were processed and normalized by converting them to equivalent FPKM (Fragments Per Kilobase of transcript per Million mapped reads) values. Results are provided in FIG. 1 and FIG. 2 for all genes having a differential expression level of 2-fold or greater. Results are graphically illustrated in FIG. 12. Genes with differential expression levels of less than about 5.5-fold [$\log_{2n}$] are indicated between the threshold lines of FIG. 12. Genes up-regulated by more than a 5.5 fold change in left tumors are indicated above the upper threshold line; genes down regulated in left tumors (i.e., up regulated in right tumors) are indicated below the lower threshold line.

While certain embodiments of the disclosed subject matter have been described using specific terms, such description is for illustrative purposes only, and it is to be understood that changes and variations may be made without departing from the spirit or scope of the subject matter.

What is claimed is:

1. A binding array comprising a plurality of binding agents adhered to a substrate, wherein the binding agents consist of polynucleotides that specifically hybridize to genes, or transcripts or cDNAs thereof, consisting of Abca4, Col6a2, Cspg4, Cthrc1, Dysf, Enho, Kcne3, Mmp9, Myh11, Nid2, Slc3a1, Stra6, Tmem47, and Usp13, and optionally include polynucleotides that specifically hybridize to genes, or transcripts or cDNA thereof, selected from the group consisting of: 2810454H06Rik, AA413626, Abcb4, Adam12, Adamts9, Akap12, Antxr1, Atp8b1, Bgn, Brinp3, C030037D09Rik, Ccdc80, Cdh2, Cdkn2b, Chsy3, Clca1, Cldn5, Clec11a, Clhc1, Cnih2, Col11a1, Col12a1, Col15a1, Col4a2, Col5a1, Col5a2, Col6a3, Col7a1, Cplx2, Crabp1, Creb3l1, Cttnbp2, Dmd, Egfl7, Ehd3, Emcn, Emx2, Epha3, Erg, Fam198b, Fam46b, Fhl1, Fjx1, Fmod, Gata6, Gcnt4, Gli2, Gm1141, Gpc4, Gpihbp1, Grem2, Gria3, Gucy1a2, Hey1, Heyl, Hmx2, Hoxb2, Hoxb7, Hoxb8, Hoxc8, Hs6st2, Htr1b, Htr2a, Igfbp3, Igfbp7, Itgb3, Jph2, Kcnb1, Kcnip4, Kcnmb1, Kcnq3, Kctd11, Khdrbs3, Klhl30, Krt42, Lama1, Lmo7, LOC100504703, Lpar4, Lrch2, Lrrc15, Lrrc55, Mcam, Mecom, Meox1, Mest, Mmp15, Mmrn1, Msx1, Mxra7, My19, Ncam1, Ndst3, Nexn, Nkd1, Nos3, Nrep, Oacyl, P4ha3, Palm2, Pcdh12, Pcdhga10, Pcsk9, Plet1os, Pnpla3, Ppbp, Prkd1, Prr9, Prss23, Ptprn, Rbp1, Rnf223, Ror2, Serp2, She, Slc12a3, Slc5a5, Slc8a3, Slit2, Snai2, Snhg18, Sobp, Sox17, Sparc, Srpx2, St8sia2, Syt5, Tacr1, Tagln, Tbx3, TIII, Tmem200a, Tmem204, Tmem252, Tnc, Tspan6, Ttc41, Unc5c, Wnt11, Glyctk, Sesn1, Gm4013, C1Gqa, Nr3c2, Cd200r4, Mag, Sc15a2, Lrfn1, Lefty1, Crym, Gm13710, Gpr82, Ccl12, Aoah, Omp, Cd226, Epor, Rab39, Gzma, Sectm1a, Gm13154, Rnase6, and Cxcl13.

2. The binding array of claim 1, wherein the binding agents are polynucleotides that specifically hybridize to the transcripts of the genes.

3. The binding array of claim 1, wherein the binding array comprises a plurality of physically distinct locations, wherein each distinct location has a distinct set of the binding agents.

4. The binding array of claim 1, wherein the array comprises a plurality of physically distinct locations each with multiple copies of a particular binding agent.

5. The binding array of claim 1, wherein each of the binding agents comprises a detectable label.

6. The binding array of claim 1, wherein the binding agents are polynucleotides that specifically hybridize to cDNAs of transcripts of the genes.

7. The binding array of claim 1, wherein the binding agents are polynucleotides that specifically hybridize to genomic DNA sequences of the genes.

* * * * *